United States Patent
Mendez Ferrer et al.

(10) Patent No.: US 10,335,380 B2
(45) Date of Patent: Jul. 2, 2019

(54) COMPOUNDS SUITABLE FOR THE TREATMENT OF MYELOPROLIFERATIVE NEOPLASMS AS WELL AS METHODS FOR THE DIAGNOSIS/PROGNOSIS OF MYELOPROLIFERATIVE NEOPLASMS

(71) Applicant: CNIC Fundacion Centro Nacional De investigaciones Cardiovasculares Carlos III, Madrid (ES)

(72) Inventors: Simon Mendez Ferrer, Madrid (ES); Lorena Arranz Salas, Madrid (ES); Joan Isern Marin, Madrid (ES)

(73) Assignee: CNIC Fundacion Centro Nacional De Investigaciones Cardiovasculares Carlos III (ES)

( * ) Notice: Subject to any disclaimer, the term of this patent is extended or adjusted under 35 U.S.C. 154(b) by 0 days.

(21) Appl. No.: 14/890,292

(22) PCT Filed: May 12, 2014

(86) PCT No.: PCT/EP2014/059678
§ 371 (c)(1),
(2) Date: Nov. 10, 2015

(87) PCT Pub. No.: WO2014/181001
PCT Pub. Date: Nov. 13, 2014

(65) Prior Publication Data
US 2016/0250163 A1    Sep. 1, 2016

(30) Foreign Application Priority Data

May 10, 2013  (ES) .................................. 201330677

(51) Int. Cl.
| | |
|---|---|
| *A61K 31/137* | (2006.01) |
| *A61K 38/18* | (2006.01) |
| *A61K 38/30* | (2006.01) |
| *A61K 38/20* | (2006.01) |
| *A61K 31/05* | (2006.01) |
| *A61K 31/138* | (2006.01) |
| *A61K 31/198* | (2006.01) |
| *A61K 31/221* | (2006.01) |
| *A61K 31/355* | (2006.01) |
| *A61K 31/36* | (2006.01) |
| *A61K 31/40* | (2006.01) |
| *A61K 31/426* | (2006.01) |
| *A61K 31/4412* | (2006.01) |

(Continued)

(52) U.S. Cl.
CPC ............ *A61K 31/137* (2013.01); *A61K 31/05* (2013.01); *A61K 31/138* (2013.01); *A61K 31/19* (2013.01); *A61K 31/195* (2013.01); *A61K 31/196* (2013.01); *A61K 31/198* (2013.01); *A61K 31/216* (2013.01); *A61K 31/221* (2013.01); *A61K 31/355* (2013.01); *A61K 31/357* (2013.01); *A61K 31/36* (2013.01); *A61K 31/40* (2013.01); *A61K 31/403* (2013.01); *A61K 31/426* (2013.01); *A61K 31/4412* (2013.01); *A61K 31/452* (2013.01); *A61K 31/4545* (2013.01); *A61K 31/4985* (2013.01); *A61K 31/513* (2013.01); *A61K 31/519* (2013.01); *A61K 31/522* (2013.01); *A61K 31/5517* (2013.01); *A61K 31/63* (2013.01); *A61K 31/66* (2013.01); *A61K 31/661* (2013.01); *A61K 38/185* (2013.01); *A61K 38/204* (2013.01); *A61K 38/2093* (2013.01); *A61K 38/30* (2013.01); *C12Q 1/6886* (2013.01); *G01N 33/57426* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 2004/0002495 A1* | 1/2004 | Sher ..................... | A61K 31/496 514/228.2 |
| 2006/0084637 A1* | 4/2006 | Alemany ............... | A61K 31/05 514/182 |

(Continued)

OTHER PUBLICATIONS

Tyagi 2011 "mirabegron: a safety review" expert opin drug safety 10(2):287-294.*

(Continued)

*Primary Examiner* — Adam Weidner
(74) *Attorney, Agent, or Firm* — Timothy J. Monahan; Monahan & Company, LLC

(57) ABSTRACT

The present findings point to mutant HSCs as the cause of BM neuroglial damage that compromises MSC survival and function, critically contributing to MPN pathogenesis. In this sense, the present invention shows that the niche damage triggered by the mutant HSC is essential for the development of a haematopoietic malignancy previously considered to be caused by the HSC alone. Targeting HSC niche-forming MSCs and their neural regulation paves the way to more efficient therapeutic strategies in MPN. For this purpose, the present invention shows that an efficient therapeutic strategy for the treatment of MPN lies on the administration of neuroprotective compounds, such as 4-methylcatechol, capable of protecting BM sympathetic nerve fibers. Additionally, another efficient therapeutic strategy is shown herein as the administration of selective β3-adrenergic agonists such as BRL37344 or Mirabegron, since this strategy will compensate for deficient sympathetic stimulation of nestin+ MSCs.

5 Claims, 39 Drawing Sheets
(37 of 39 Drawing Sheet(s) Filed in Color)
Specification includes a Sequence Listing.

(51) Int. Cl.
*A61K 31/452* (2006.01)
*A61K 31/4545* (2006.01)
*A61K 31/4985* (2006.01)
*A61K 31/513* (2006.01)
*A61K 31/522* (2006.01)
*A61K 31/63* (2006.01)
*A61K 31/66* (2006.01)
*G01N 33/574* (2006.01)
*C12Q 1/6886* (2018.01)
*A61K 31/19* (2006.01)
*A61K 31/195* (2006.01)
*A61K 31/196* (2006.01)
*A61K 31/216* (2006.01)
*A61K 31/357* (2006.01)
*A61K 31/403* (2006.01)
*A61K 31/519* (2006.01)
*A61K 31/5517* (2006.01)
*A61K 31/661* (2006.01)
*G01N 33/00* (2006.01)
*C12Q 1/68* (2018.01)

(56) References Cited

U.S. PATENT DOCUMENTS

2010/0240542 A1* 9/2010 Soper ................ G01N 33/5011
506/8
2011/0262566 A1* 10/2011 Goto ................... A61K 31/517
424/725
2012/0214825 A1* 8/2012 Vannucchi ........... A61K 31/436
514/262.1
2013/0065902 A1* 3/2013 Aissaoui ............... C07D 209/88
514/249
2013/0102614 A1* 4/2013 Liu ...................... A61K 31/496
514/254.07
2013/0143797 A1 6/2013 Tisdale et al.
2014/0113919 A1 4/2014 Baffert et al.

OTHER PUBLICATIONS

Iinternational Searching Authority, PCT International Search Report, dated Sep. 19, 2014.
Iinternational Searching Authority, Written Opinion, dated Sep. 19, 2014.
Marty, C., et al., A role for reactive oxygen species in JAK2 (V617F) myeloproliferative neoplasm progression, Leukemia, Apr. 26, 2013, pp. 2187-2195, 27(11), Macmillan Publishers Ltd.
Gao, X-Z., et al., The effects of amifostfine (AM) on myelodysplastic and myeloid leukemia progenitor cells, Proceedings of the Annual Meeting of the American Association for Cancer Research, Mar. 1, 1997, p. 323, 38, US.
Kiao, W., et al., Lyn- and PLC-beta 3-dependent regulation of SHP-1 phosphororylation controls Stat5 activity and myelomonocytic leukemia-like disease, Blood, Dec. 23, 2010, pp. 6003-6013, 116(26).
Arraz, L., et al., Sympathetic Neuropathy of the Hematopoietic Stem Cell Niche is Essential for Myeloproliferative Neoplasms, Blood, Nov. 1, 2013, p. 268, 122(21).

* cited by examiner a  Peripheral blood

Bone marrow

COMPOUNDS SUITABLE FOR THE TREATMENT OF MYELOPROLIFERATIVE NEOPLASMS AS WELL AS METHODS FOR THE DIAGNOSIS/PROGNOSIS OF MYELOPROLIFERATIVE NEOPLASMS

REFERENCE TO AN ELECTRONIC SEQUENCE LISTING

The contents of the electronic sequence listing (sequence listing 2nd amended 2016 02 11.txt; Size: 15,992 bytes; and Date of Creation: Feb. 11, 2016) is herein incorporated by reference in its entirety.

FIELD OF THE INVENTION

The present invention relates to the medical field, in particular to compounds suitable for the treatment of MPN (myeloprofilerative neoplasms) as well as methods for the diagnosis/prognosis of MPN:

BACKGROUND OF THE INVENTION

Myelodysplastic/myeloproliferative neoplasms (MPN) are a group of diseases that affect normal blood cell production in the bone marrow. In this case the bone marrow causes an overproduction of one or more blood cell types (red cells, white cells or platelets). Complications arise over time due to the abnormally high number of blood cells that accumulate in the bone marrow aidnd in the circulating blood.

There are different types of MPN. They are generally distinguished from each other by the type of cell which is most affected, such as for example:
  Polycythemia vera—an overproduction of red blood cells.
  Essential thrombocythemia—overproduction of platelets
  Chronic myelomonocytic leukaemia (CMML)—overproduction of white cells (granulocytes)
  Chronic neutrophilic leukaemia—overproduction of neutrophils (a type of white cell)
  Chronic eosinophilic leukaemia—overproduction of eosinophils (a type of white cell)
  Idiopathic myelofibrosis—a condition in which bone marrow tissue is gradually replaced by fibrous scar-like tissue, disrupting normal blood cell production.

In many cases, these diseases develop slowly and get worse gradually. In some cases myeloproliferative neoplasms can progress to leukaemia.

Compounds capable of preventing and treating these types of diseases are urgently needed.

BRIEF DESCRIPTION OF THE INVENTION

A first aspect of the invention refers to:
  TrK or RET receptor agonists, preferably to 3-3 adrenergic receptor agonist compounds; or to
  neuroprotective compounds capable of protecting bone marrow sympathetic nerve fibres,
for use in treating and/or preventing MPN (myeloproliferative neoplasms).

In a preferred embodiment of the first aspect of the invention, the MPN are selected from the list consisting of chronic myeloid leukaemia (CML), Chronic myelomonocytic leukaemia (CMML), polycythaemia vera, essential thrombocythaemia, primary myelofibrosis, Idiopathic myelofibrosis, agnogenic myeloid metaplasia, chronic neutrophilic leukaemia, chronic eosinophilic leukaemia and mastocytosis.

In a preferred embodiment of the first aspect of the invention or of any of its other preferred embodiments, the beta-3 adrenergic receptor agonist compound is a selective beta-3 adrenergic receptor agonist compound. More preferably, said selective agonist is selected from the following list consisting of:
  BRL 37344;
  CL 316243;
  AZ 002;
  BMS 187257;
  L-755507;
  L-750355;
  FR-149175;
  GW427353 (Solabegron);
  YM178 (Mirabegron/myrbetriq);
  CR 58611;
  SR 58611A (Amibegron);
  SR 59104A;
  SR 59119A;
  SAR150640;
  L-796568; and
  CL-316243
and their pharmaceutically acceptable salts.

In a preferred embodiment of the first aspect of the invention or of any of its other preferred embodiments, said selective agonist is a phenylethanolamine. Preferably said selective beta-3 adrenergic receptor agonist compound is a compound with the following general formula:

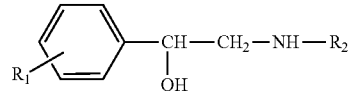

Formula I wherein R1 is selected from hydrogen and halogen; and wherein R2 is an aralkyl, being able to be substituted in the aryl part and/or in the alkyl part, or a radical selected from:

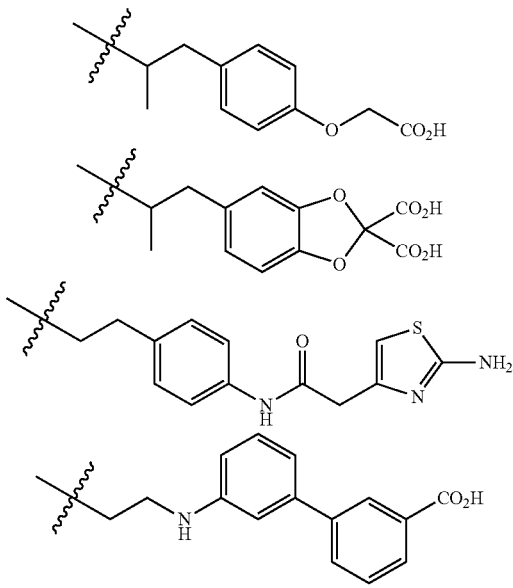

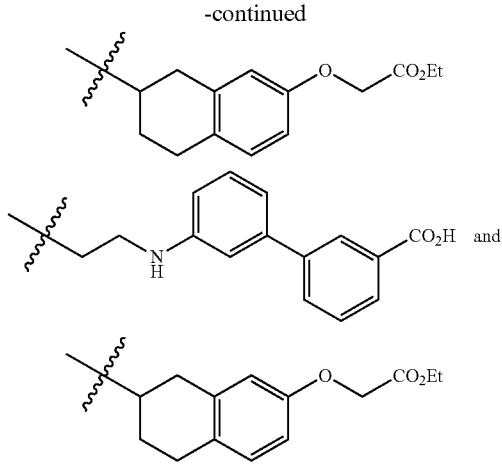

Preferably, the compound of formula I is selected from the list of compounds consisting of:

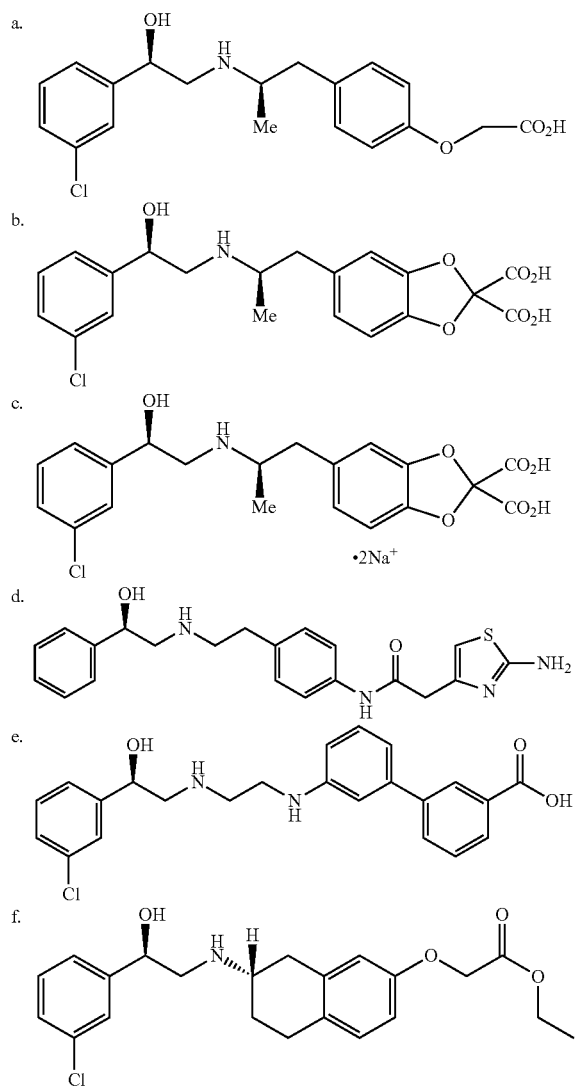

and their pharmaceutically acceptable salts.

A second aspect of the invention refers to a neuroprotective compound capable of protecting bone marrow sympathetic nerve fibres for use in treating and/or preventing MPN (myeloprofilerative neoplasms).

Preferably said compound can be selected from the list consisting of 4-methylcatechol; NGF (neuron growth factors); glial cell line-derived neurotrophic factors (GDNF) pertaining to the Neurturin (NRTN), artemin (ARTN) or persephin (PSPN) families; Neurotrophin-3 and Neurotrophin 4/5; interleukin-6 (IL-6); Insulin-like growth factor 1 (IGF-1); vitamin E, in particular the α-tocopherol form of vitamin E; Acetylcysteine also known as N-acetylcysteine or N-acetyl-L-cysteine (abbreviated NAC); Acetyl-L-carnitine or ALCAR; amifostine and Leukemia inhibitory factor (LIF).

More preferably said neuroprotective compound can be selected from the list consisting of sitagliptin, saxagliptin/Onglyza, linagliptin, dutogliptin, gemigliptin, alogliptin and vildagliptin/Galvus.

A third aspect of the invention refers to a medicinal product or a pharmaceutical composition comprising a compound as defined in any of the first or second aspects of the invention, for use in treating and/or preventing MPN (myeloprofilerative neoplasms).

A fourth aspect of the invention refers to a method of diagnosis or prognosis of a MPN in a human subject, wherein the method comprises using as an indicator the estimation of the sympathetic nervous system fibers in the bone marrow of the subject by:
  a. immunostaining the tyrosine hydroxylase present in bone marrow biopsies, optionally taken over time, from the subject; and
  b. comparing if the sympathetic nervous system fibers present in the biopsies of step a) are reduced in comparison to the sympathetic nervous system fibers present in the bone marrow of a normal subject or in comparison to a reference or control value;
wherein if the sympathetic nervous system fibers are reduced in comparison to the sympathetic nervous system fibers present in a normal subject or in comparison to a reference or control value then bone marrow neural damage which preceeds nestin+ mesenchymal stem cell reduction is progressing in the subject; and
wherein if the subject shows at least a 3-fold reduction in the bone marrrow area occupied by tyrosine hydroxylase fibers in comparison to the sympathetic nervous system fibers present in a normal subject or in comparison to a reference or control value then the subject suffers from a MPN.

Preferably, the reference or control value of the bone marrow area occupied by sympathetic fibers is 0.15±0.09% of the total bone marrow area in the section.

A fifth aspect of the invention refers to a method of diagnosis or prognosis of a MPN in a subject, which comprises the following steps:
  a. obtaining a biological sample from the bone marrow of a subject;
  b. comparing the mRNA expression of the glial fibrillary acidic protein in the sample of step a) with a reference or control value of the mRNA expression of the glial fibrillary acidic protein in a normal subject or with the mRNA expression of the glial fibrillary acidic protein in a biological sample obtained from a normal subject;
wherein if the mRNA expression of the glial fibrillary acidic protein in the sample of step a) is reduced in comparison to the reference or control value or to the mRNA expression of the glial fibrillary acidic protein in the biological sample obtained from a normal subject, then BM neural damage which preceeds nestin+ MSC reduction is progressing in the subject; and
wherein if the subject shows at least a 160 fold reduction of the value of the mRNA expression of the glial fibrillary acidic protein normalised to the mRNA expression of the housekeeping gene GAPDH in controls then the subject suffers from a MPN.

Preferably, the reference or control value of the mRNA expression of the glial fibrillary acidic protein is 0.48±0.03 normalised to the mRNA expression of the housekeeping gene Glyceraldehyde-3-phosphate dehydrogenase (GAPDH).

A sixth aspect of the invention refers to a method of diagnosis or prognosis of a MPN in a subject, which comprises the following steps:
  a. Obtaining a biological sample from the bone marrow of a subject over time;
  b. using as an indicator the total number of BM nestin+ MSCs in the sample of step a), measuring this indicator by the immunostaining of nestin followed by scoring taking into account the number of NESTIN+ perivascular niches (either single cells or clusters of up to 3 cells) in the bone marrow samples (on average 7.2 mm$^2$ of BM should be evaluated and results extrapolated to 1 mm$^2$);
  c. comparing the total number of BM nestin+ MSCs in the biological sample of step a) with a reference or control value of the total number of BM nestin+ MSC in a normal subject or with the total number of BM nestin+ MSCs in a biological sample obtained from a normal subject;

wherein if the number of cells is reduced in comparison to the reference or control value or to the number of BM nestin+ MSCs in the biological sample obtained from a normal subject, then damage of the niche that preceeds myelofibrosis is present in the subject; and
wherein if the subject shows at least a 6-fold reduction of the number BM nestin+ MSC in a normal subject then the subject suffers from a MPN.

Preferably, the reference or control value of the total number of BM nestin+ cells in a normal subject is 1.15±0.3 niches per mm$^2$ (each one containing at least one positive cell). A seventh aspect of the invention refers to a method of diagnosis or prognosis of a MPN in a subject, which comprises the following steps:
  a. obtaining a biological sample from the bone marrow of a subject;
  b. using as an indicator the total number of nestin+ MSC in the sample of step a) by measuring the mRNA expression of NESTIN by qRT-PCR in the sample of step a);
  d. comparing the mRNA expression of NESTIN in the sample of step a) with a reference or control value of the mRNA expression of NESTIN in a normal subject or with the mRNA expression of NESTIN in a biological sample obtained from a normal subject, wherein if the mRNA expression of NESTIN in the sample of step a) is reduced in comparison to the reference or control value or to the mRNA expression of NESTIN in the biological sample obtained from a normal subject, then damage of the niche that preceeds myelofibrosis is present in the patient, and
wherein if the subject shows at least a 13-fold reduction of the value of the mRNA expression of NESTIN normalised to the mRNA expression of the housekeeping gene GAPDH in controls.

Preferably, the reference or control value of the mRNA expression of NESTIN is 4.86±4.55 normalised to the mRNA expression of the housekeeping gene Glyceraldehyde-3-phosphate dehydrogenase (GAPDH).

An eight aspect of the invention refers to a kit suitable for implementing any of the precedent methods.

A ninth aspect of the invention refers to a method for screening or producing a compound suitable for the treatment of a MPN, which method comprises the steps of:
  a. Selecting a compound;
  b. Determining whether said compound shows a selectivity towards the beta-3 receptor that is about ≥10 times higher, more preferably about ≥100 times higher, and still more preferably about ≥1000 times higher, with respect to other beta adrenergic receptors and whether it increases the basal activity of the beta-3 receptor when it comes into contact with the receptor;
  c. Recovering said compound if it complies with the criteria set in step b); and
  d. Producing said compound.

BRIEF DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION OF THE INVENTION

The stem cell niche has recently emerged as an oncogenic unit and an important element in regulating cancer stem cells, including HSCs (hematopoietic stem cells). Most MPN (myeloprofilerative neoplasms) patients who do not carry the BCR-ABL fusion have an acquired mutation in Janus kinase 2 (JAK2V617F) in HSCs that results in constitutive kinase activity, leading to uncontrolled expansion of HSCs and erythroid, megakaryocytic and myeloid progenitors. Somatic mutations in thrombopoietin receptor or calreticulin genes are found in some MPN patients and additional HSC mutations also affect disease progression. Changes in the HSC microenvironment might also contribute to MPN development, and expansion of BM fibroblasts and bone-forming cells suggests the participation of MSCs.

The authors of the present invention previously reported that mouse BM (bone marrow) nestin+ MSCs are required to maintain HSCs and that human BM nestin+ cells can expand HSCs. Here they found that, despite elevated BM blood-vessel density in MPN patients, nestin+ cell number and NESTIN mRNA expression were markedly reduced (FIG. 1a-b). This was reproduced in Mx1-cre;JAK2V617F mice that developed MPN upon plpC treatment (FIG. 1c). MPN mice were intercrossed with a Nes-gfp line to label MSCs. Both compound mutant mice and Nes-gfp animals transplanted with mutant BM cells developed MPN and had less BM MSCs defined by GFP, surface marker expression and functional assays (FIG. 1d-g and FIG. 5a-f). Since MSC loss was concomitant with incipient BM fibrosis, the authors of the present invention conducted long-term in vivo lineage-tracing studies to determine whether nestin+ MSCs differentiate into fibroblasts or osteoblasts in MPN, thereby contributing to the stromal changes in these mice (FIG. 5g-j).

Figure 6:
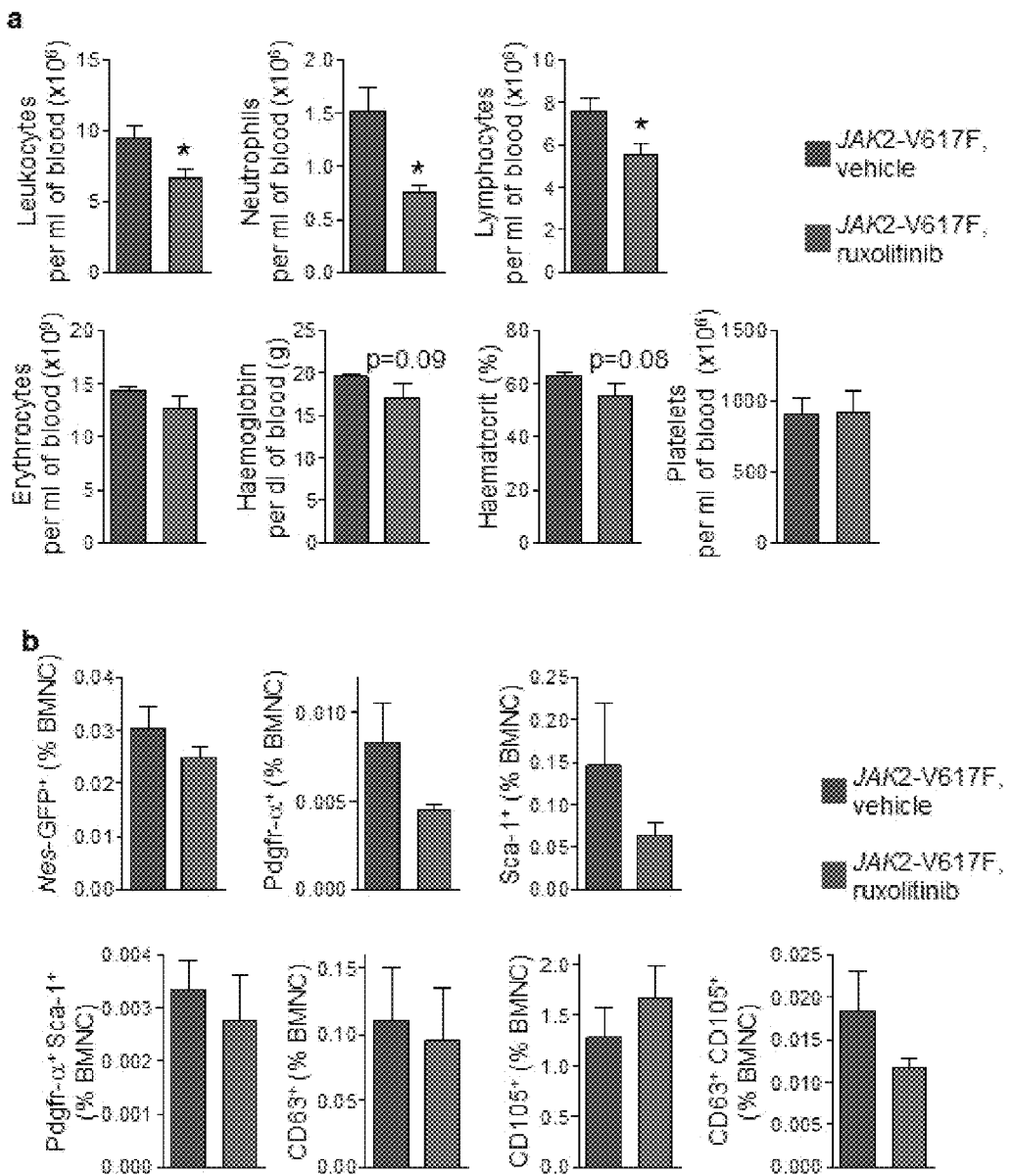
FIG. 6. Treatment with the JAK1/2 inhibitor ruxolitinib reduces haematopoietic cell expansion in MPN but does not rescue BM MSCs. Nes-gfp mice were transplanted with BM cells from plpC-induced Mx1-cre;JAK2-V617F mice and treated with ruxolitinib or vehicle over 8 weeks, starting 2 weeks after transplantation (n=4-6). a, Peripheral blood counts. b, Frequency of immunophenotypically-defined BM CD45− CD31− Ter119− cells. Mean±SEM. * p<0.05 (unpaired two-tailed t test).
Figure 7:
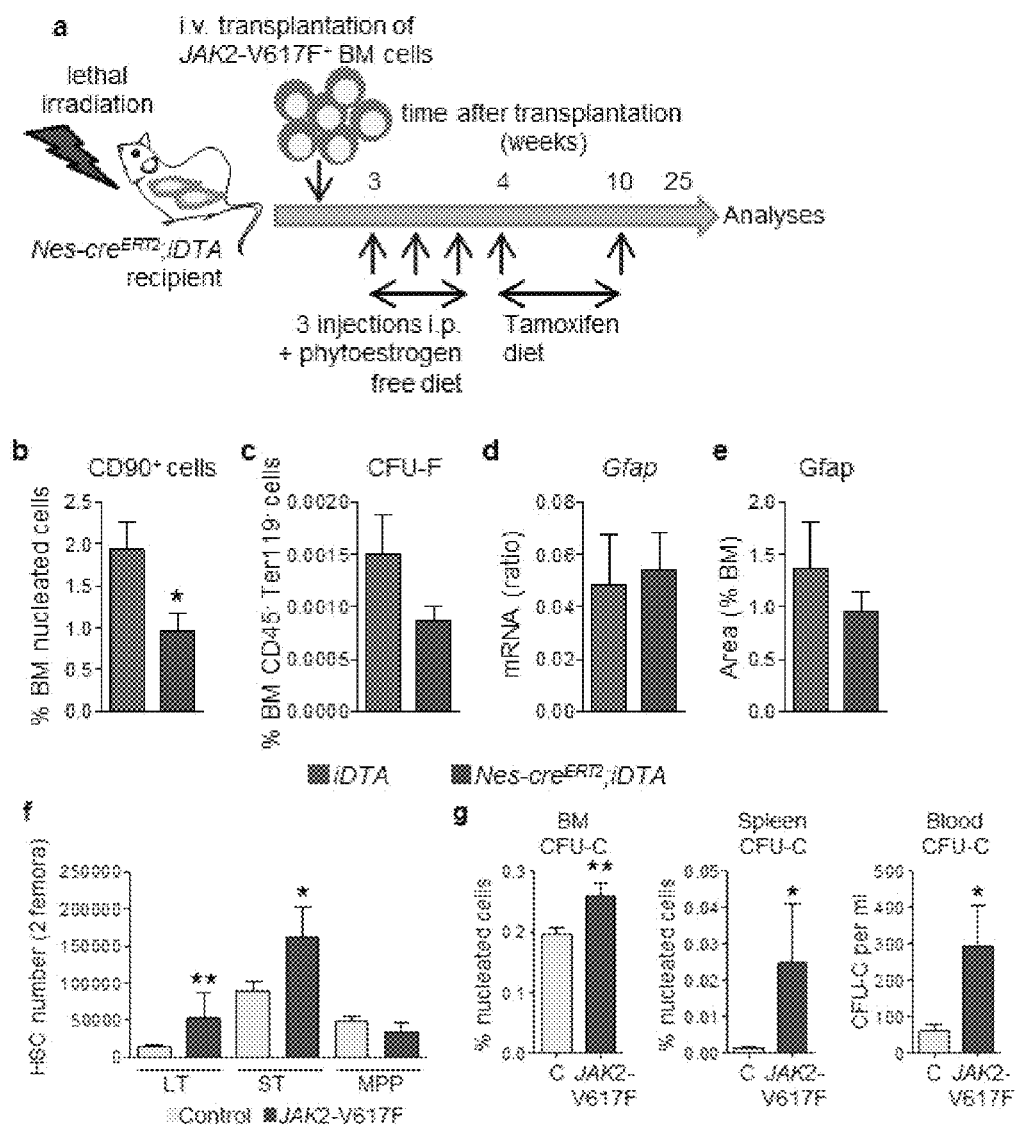
FIG. 7. Depletion of nestin+ cells or their Cxcl12 production accelerates MPN. a, Experimental design for in vivo nestin+ cell depletion. NescreERT2;iDTA and control iDTA mice were transplanted with BM cells from plpC-treated Mx1-cre;JAK2-V617F and control mice and treated with tamoxifen (n=4-5). b-e, Unlike Schwann cells, MSCs are reduced in Nes-creERT2;iDTA BM. b-c, Frequency of (b) BM CD45−CD31−Ter119−CD90+ cells and (c) fibroblastic colony-forming units (CFU-F) in BM CD45−Ter119− cells from Nes-creERT2;iDTA and control mice after 4-week tamoxifen treatment. d, Expression of glial fibrillary acidic protein (Gfap) mRNA (normalised to Gapdh) in the BM of mice in (a). e, Quantification of Gfap immunostaining of femoral BM from mice in (b-c). f-k, Early mutant HSC expansion and mobilisation correlates with reduced Cxcl12 expression in BM nestin+ cells. f-g, BM lin-sca-1+c-kit+ (f) CD34−Flt3− long-term (LT) and CD34+Flt3− short-term (ST) HSCs, and CD34−Flt3− multipotent progenitors (MPP) and (g) frequency of haematopoietic colony-forming units in culture (CFU-C) from BM nucleated cells, spleen or peripheral blood from Nes-Gfp;Mx1-cre;JAK2-V617F and control mice 6 weeks after plpC treatment (n=3-11). h, Appearance (inset; scale bar, 1 cm) and hematoxylin and eosin stainings of spleens (magnification 100×). i-k, Cxcl12 (i) protein and (j-k) mRNA levels in BM (i) extracellular fluid, (j) nucleated cells and (k) stromal Nes-GFP+ cells of (i-j) Mx1-cre;JAK2-V617F and control mice 6 weeks after plpC treatment or (k) Nes-gfp mice 10 weeks after transplantation with mutant BM or control cells (n=4-7). l, Circulating platelets in Nes-creERT2;Cxcl12fl/fl and control Cxcl12fl/fl littermates 18 weeks after transplantation with BM cells from MPN mice and 12 weeks after tamoxifen treatment (n=11-14). Mean±SEM. * $p<0.05$, ** $p<0.01$ (unpaired two-tailed t test).
Figure 7:
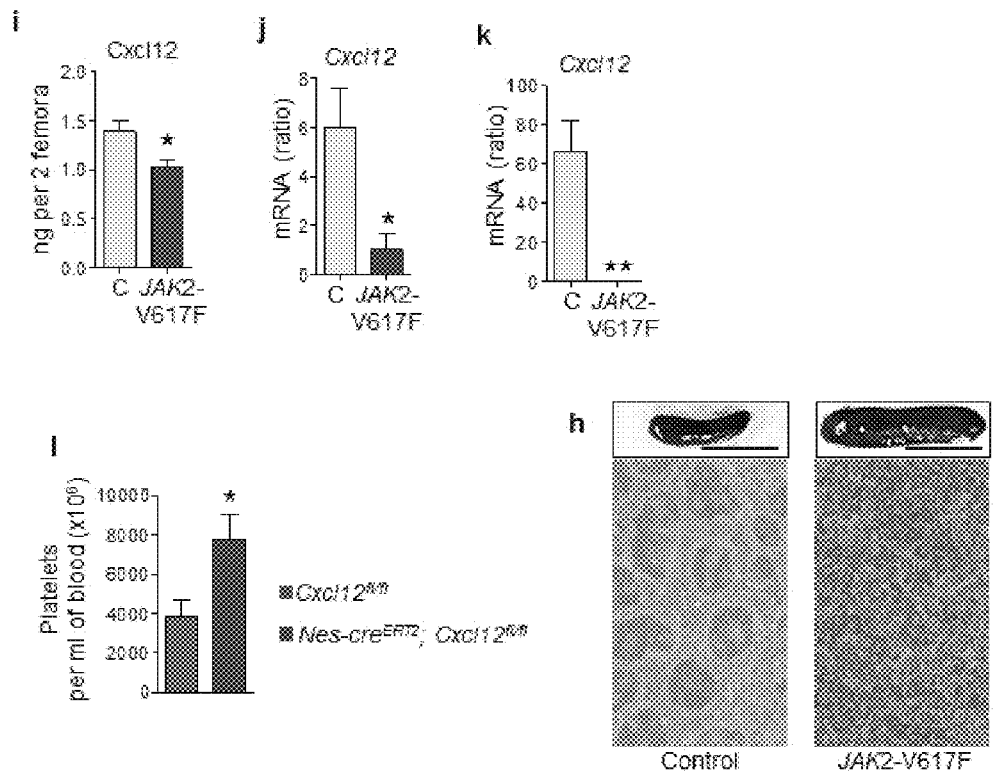
Figure 8:
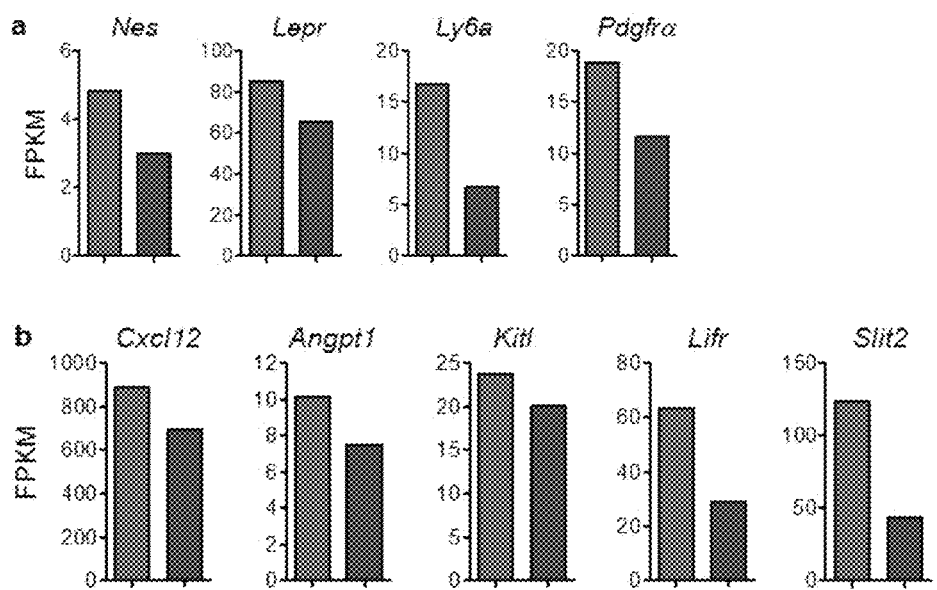
FIG. 8. Neuroglial damage in MPN-affected BM stroma. a-d, Expression of neuroglial gene sets in MPN BM Nes-GFP+ cells. a-c, Selected transcript expression in fragments per kilobase of exon per million fragments mapped (FPKM) of (a) mesenchymal genes, (b) HSC-niche related genes and (c) neural-related genes. RNAseq in CD45−CD31−Ter119−GFP+ cells isolated from compound MPN and control mice 6 weeks after plpC treatment (samples pooled from 3 mice). d, Gene set enrichment analyses (GSEA) of RNAseq data. e-f, Enrichment plot of coordinated changes in (e) neuroactive ligand-receptor interactions and (f) the transcriptome of neurons, astrocytes and olygodendrocytes. g-h, BM Nes-GFP+ cells are different from sympathetic nerve fibres and mature Schwann cells. Immunostaining of (g) tyrosine hydroxylase (TH) to visualize sympathetic nerve fibres and (h) glial fibrillary acidic protein (GFAP) for mature Schwann cells in Nes-gfp BM. Note the close association of Nes-GFP+ cells to distinctive TH+ or GFAP+ cells. i, BM biopsies from (left and middle) control or (right) MPN patients immunostained with (left) secondary Ab as negative control or (middle and right) anti-TH antibodies. Nuclei were counterstained with DAPI. Scale bar, (g) 75 μm, (h) 50 μm, (i) 100 μm.
Figure 8:
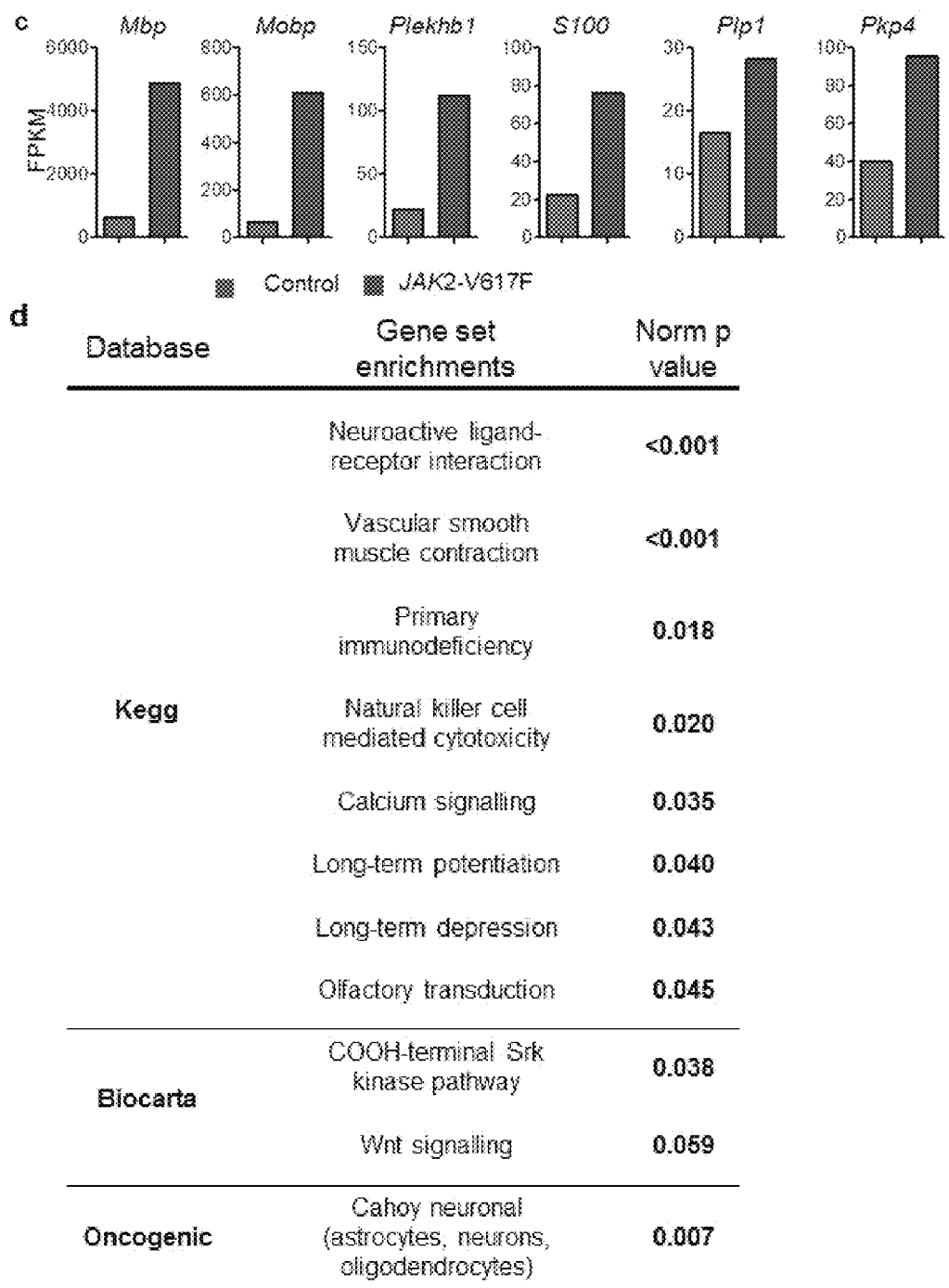
Figure 8:
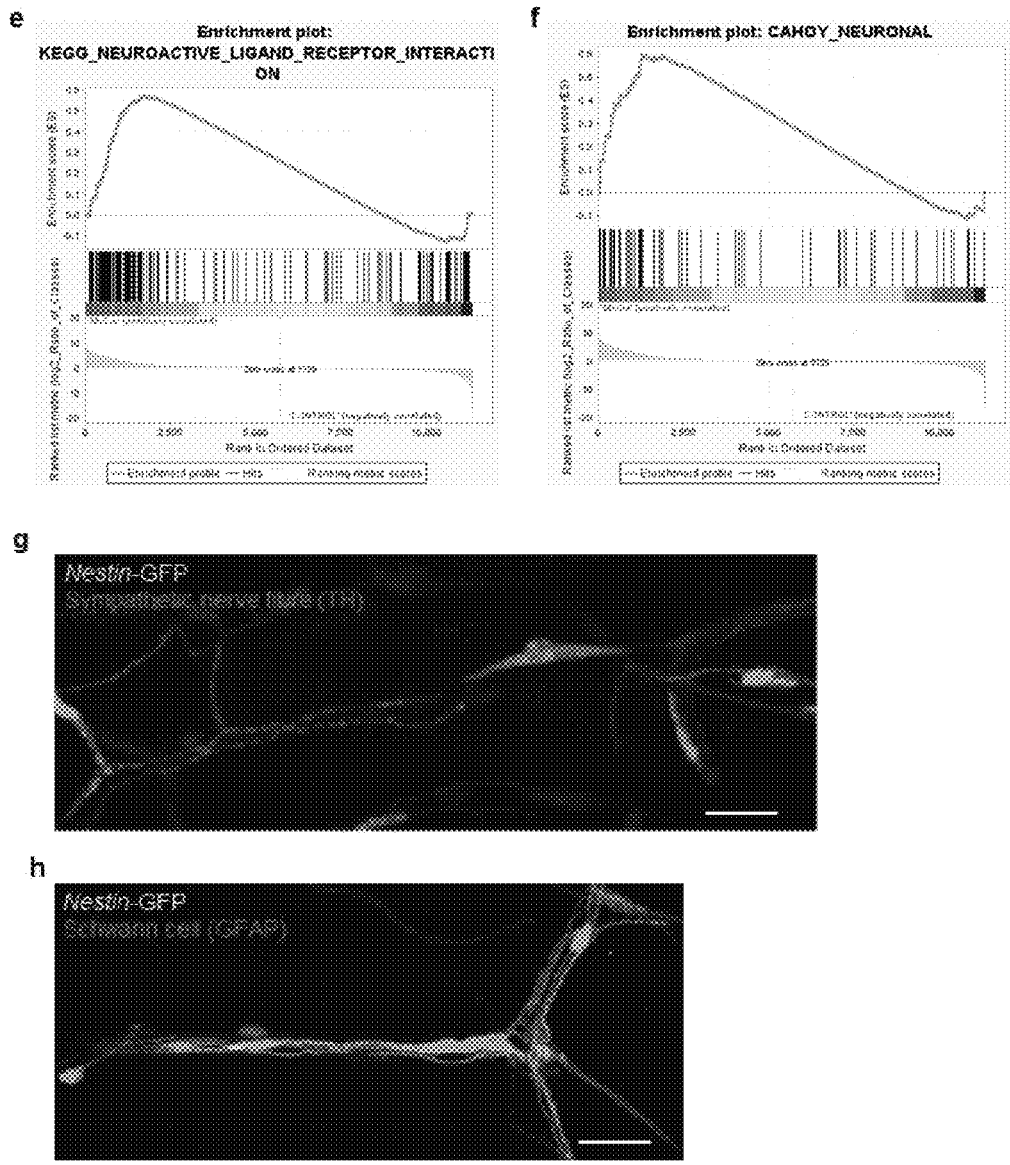
Figure 8:
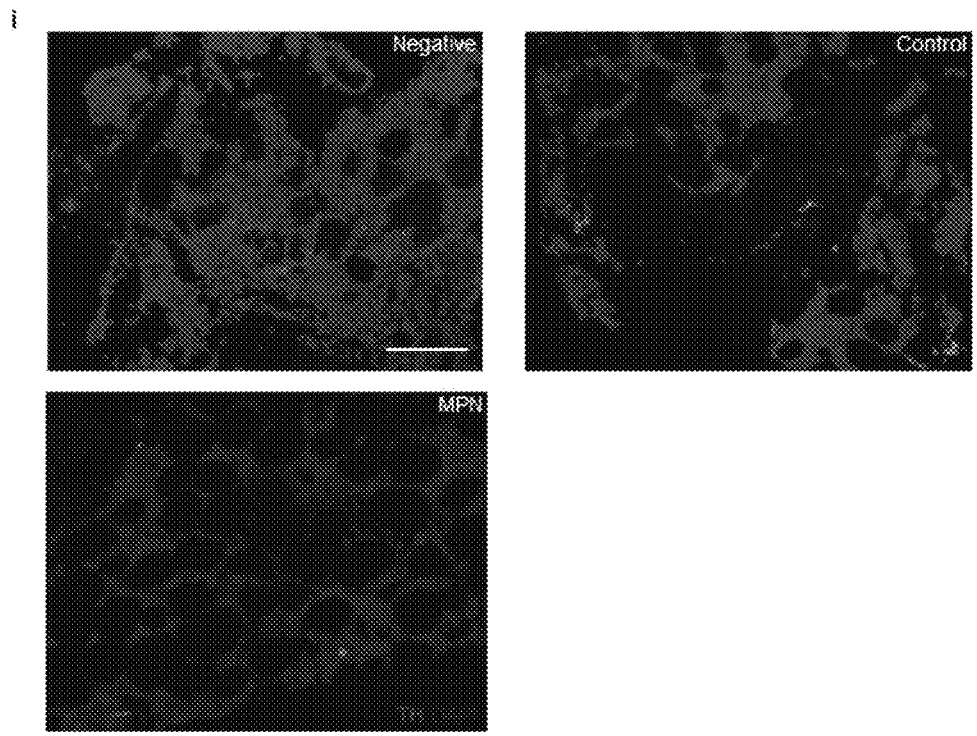

Unexpectedly, the vascular patterns of GFP+ cells were similar to those in unaffected Nes-gfp mice (FIG. 1h-i). Nestin+ MSC reduction was instead explained by 3-fold increased apoptotic rate in mutant mice (FIG. 1j), not prevented by the JAK inhibitor ruxolitinib (FIG. 6). To determine whether nestin+ MSC death could in turn stimulate MPN progression, the authors selectively depleted nestin+ cells in vivo. This depletion did not affect mature BM Schwann cells, reported to express nestin, but reduced MSCs, associated with increased white and red blood cells (FIG. 1k and FIG. 7a-e). BM sections revealed excessive fibroblasts and bone formation, not yet detectable in control mice (FIG. 1l), consistent with nestin+ cells not generating fibroblasts or bone cells in MPN.

Disease acceleration following nestin+ cell depletion also manifested as severe spleen infiltration, still absent in control mice (FIG. 1m). At early disease stage, most primitive HSCs showed highest expansion, leading to increased haematopoietic progenitors in BM, peripheral blood and spleen. The chemokine Cxcl12 regulates HSC migration and quiescence and is highly expressed by nestin+ MSCs. Early HSC mobilisation correlated with decreased BM Cxcl12, consistent with MSC reduction. In addition, Cxcl12 expression dropped 70-fold in MPN BM Nes-GFP+ cells (FIG. 7f-k). Deletion of Cxcl12REF24 in nestin+ cells in vivo increased BM haematopoietic progenitors and circulating platelets (FIG. 1n and FIG. 7l). MSC-derived Cxcl12 can thus negatively regulate JAK2V617F+HSC expansion.

Figure 2A:
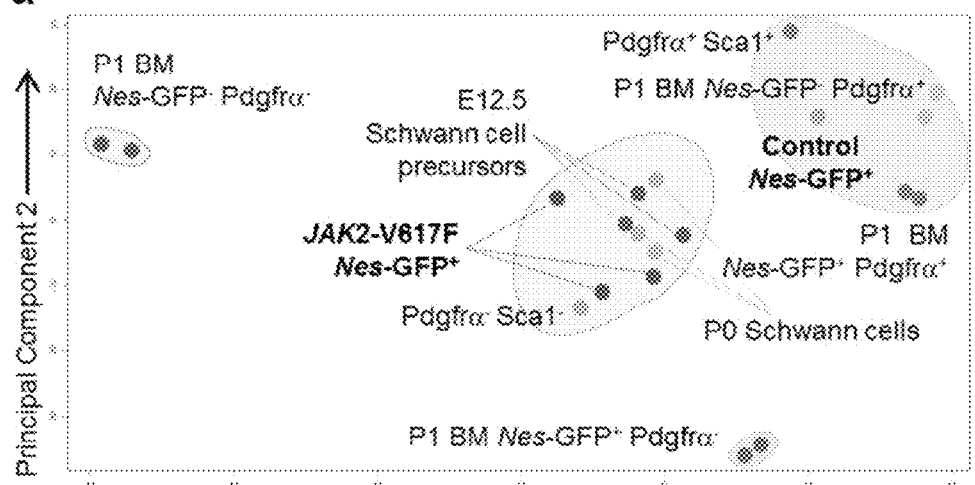
FIG. 2. BM Schwann cell death triggered by HSPC-derived interleukin-1β precedes nestin+ MSC apoptosis in MPN. a, Principal component analysis of control and MPN BM CD45−CD31−Ter119−Nes−GFP+ cells compared with mesenchymal stromal (adult BM Pdgfra+Sca1+ and neonatal BM Pdgfra+Nes-GFP+/− cells; purple shaded area) and Schwann cells (E12.5 Schwann cell precursors and neonatal Schwann cells; green shaded area; see Methods). b, QPCR validation. c, Nes-gfp skull BM 5 weeks after transplantation with control or MPN BM cells; fluorescent signals of GFP and sympathetic nerve fibres detected with anti-tyrosine hydroxylase (Th) antibodies. d, Immunostaining of glial fibrilar acidic protein (Gfap) to visualize Schwann cells in control and MPN BM. Scale bar, 200 μm (c), 100 μm (d). e, Quantification of Th+ fibres in BM from controls and MPN patients (n=2-16). f, GFAP mRNA expression in BM cells of controls, MPN patients and mice (n=2-11). g, Timecourse analyses of Schwann cells (Gfap), sympathetic fibres (Th) and Nes-GFP+ cell apoptosis in Nes-gfp;Mx1-cre;JAK2V617F+ and control mice 2-8 weeks after plpC treatment (n=3-7). h, Frequency of BM CD45−CD31−Ter119−CD105+ cells after 18-week interleukin-1 receptor antagonist (IL1ra) treatment (n=4-5). i, Apoptotic rate of MSCs and Schwann cells in vitro derived from neonatal BM Nes-GFP+ cells and cocultured for 24 h with control or MPN adult BM lin-sca-1+c-kit+ (LSK) cells (±200 ng ml-1 IL1ra). TUNEL staining (pink) of Schwann cells; nuclei were counterstained with DAPI (blue). Scale bar, 100 μm. Mean±SEM. * p<0.05; *** p<0.001 (unpaired two-tailed t test).
Figure 2A:
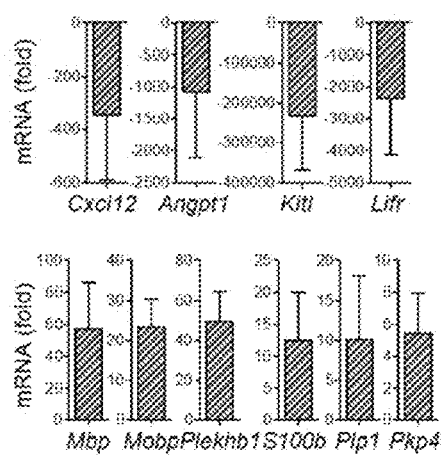
Figure 2B:
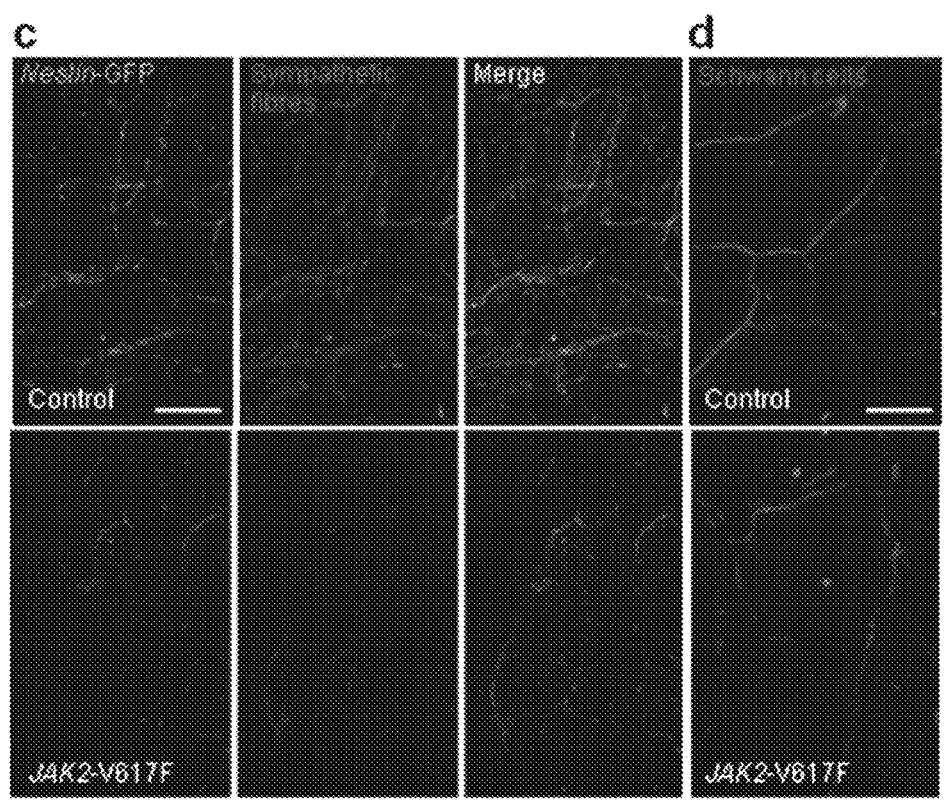
Figure 2C:
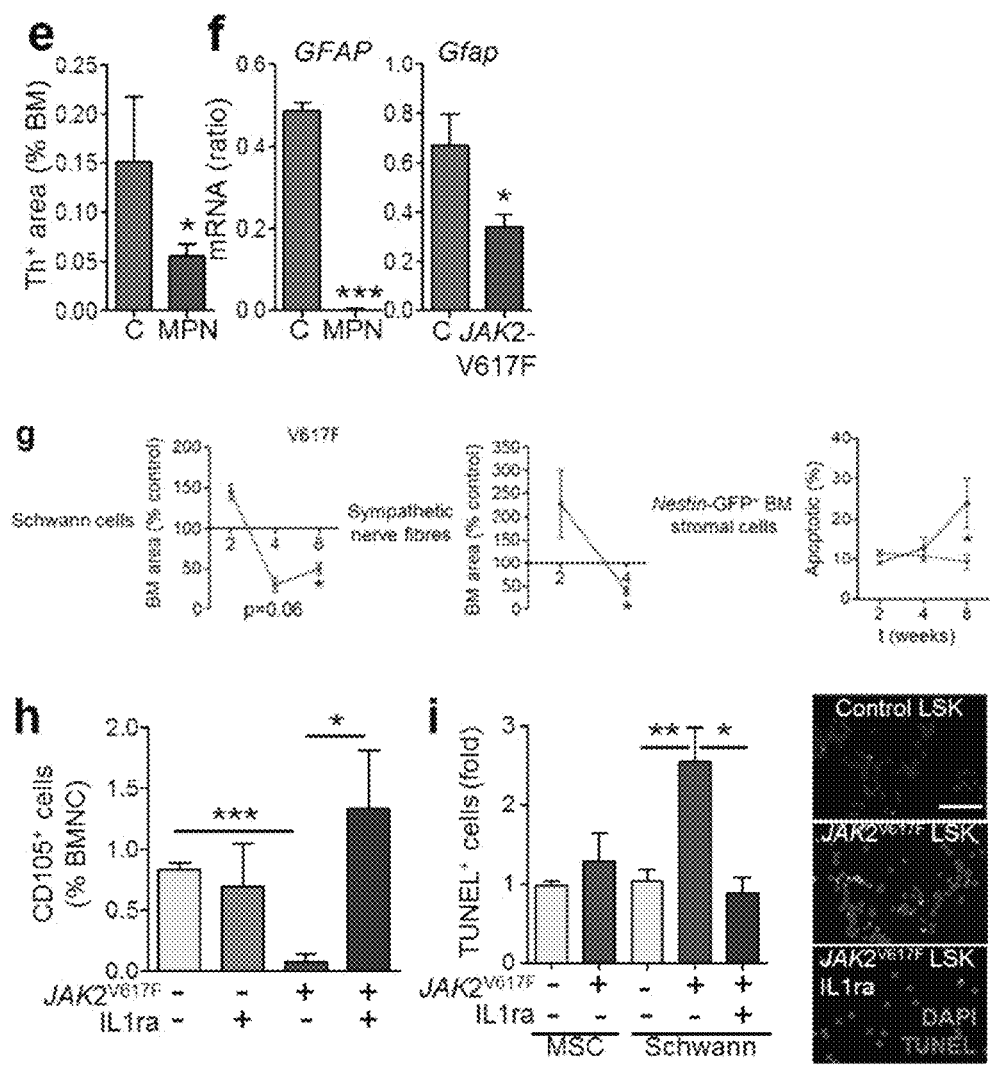

To better understand BM nestin+ cell alterations, genome-wide expression was profiled by next-generation sequencing. Expression of MSC and HSC-related genes was lower in MPN Nes-GFP+ cells, which instead showed enrichment in Schwann cell genes and neural-related functional categories (FIG. 8a-d and Table 1). Principal component analyses of independent biological samples compared with publically available data showed that control Nes-GFP+ cells were closest to mesenchymal progenitors, whereas MPN Nes-GFP+ clustered away from them and close to Schwann cells (FIG. 2a). These changes, confirmed by qPCR (FIG. 2b), suggested an altered HSC niche neural component in MPN.

Figure 9:
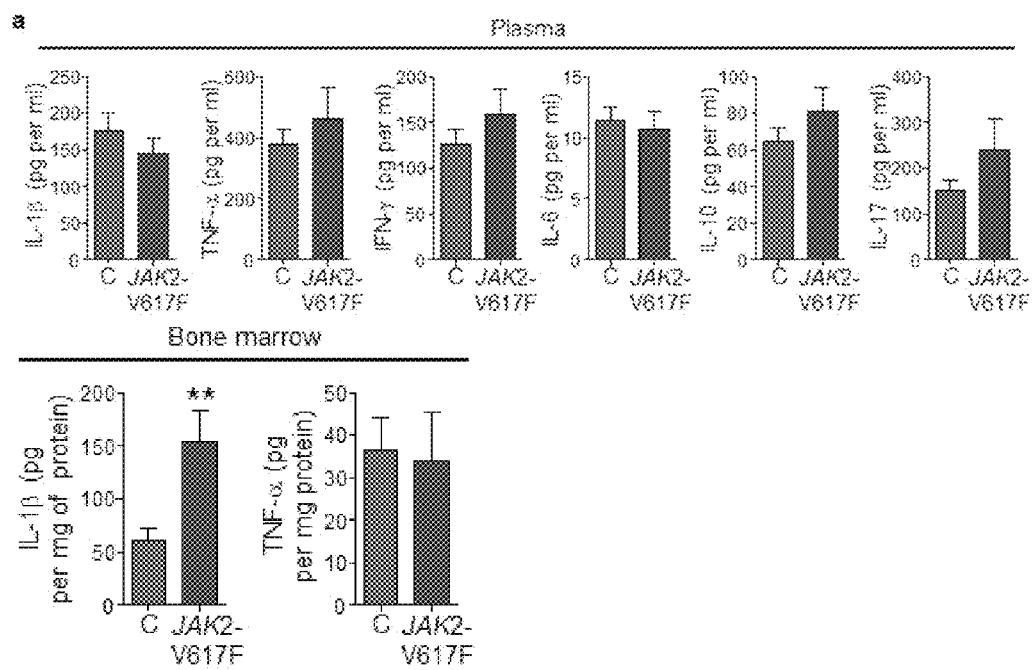
FIG. 9. Contribution of IL-1β to early MPN pathogenesis. a, Increased BM IL-1β levels early in MPN. Multiplex ELISA analysis of proinflammatory (IL-1β, TNF-α, IFN-γ, IL-6), regulatory (IL-17) and anti-inflammatory (IL-10) mediators in plasma (n=13-16) and BM extracellular fluid samples (n=6-11; only IL-1β and TNF-α were detectable) from control and Mx1-cre;JAK2-V617F mice 4-8 weeks after plpC treatment. b-f, Nes-gfp mice were transplanted with BM cells from MPN and control mice and analysed 2 weeks later (n=3-6). b-d, mRNA expression of (b) IL-1 and (c) its activating enzyme caspase-1 (Casp1), and (d) BM frequencies of lin-sca-1+c-kit+ haematopoietic progenitors and CD11b+Ly-6G(1A8)− monocytes. e-f, mRNA expression of (e) IL-1 receptor (IL1r) and (f) its antagonist (IL1ra) in BM CD45−CD31−Ter119−Nes-GFP+/− cells. g, Number of circulating platelets in WT mice transplanted with MPN and control BM cells and treated over 18 weeks with IL1ra, starting 2 weeks after transplant. h, Frequency of BM CD45−CD31−Ter119−CD90+ cells in mice in (g). i-j, qPCR analyses of (i) IL-1β and (j) Casp1 mRNA expression in haematopoietic progenitors and monocytes isolated from the BM of mice in (g). Gapdh was used as housekeeping gene (n=4-5). Mean±SEM. * $p<0.05$,  $p<0.01$, * $p<0.001$ (unpaired two-tailed t test).
Figures 9B, 9C, 9D, 9E, 9F, 9G, 9H, 9I, 9J:
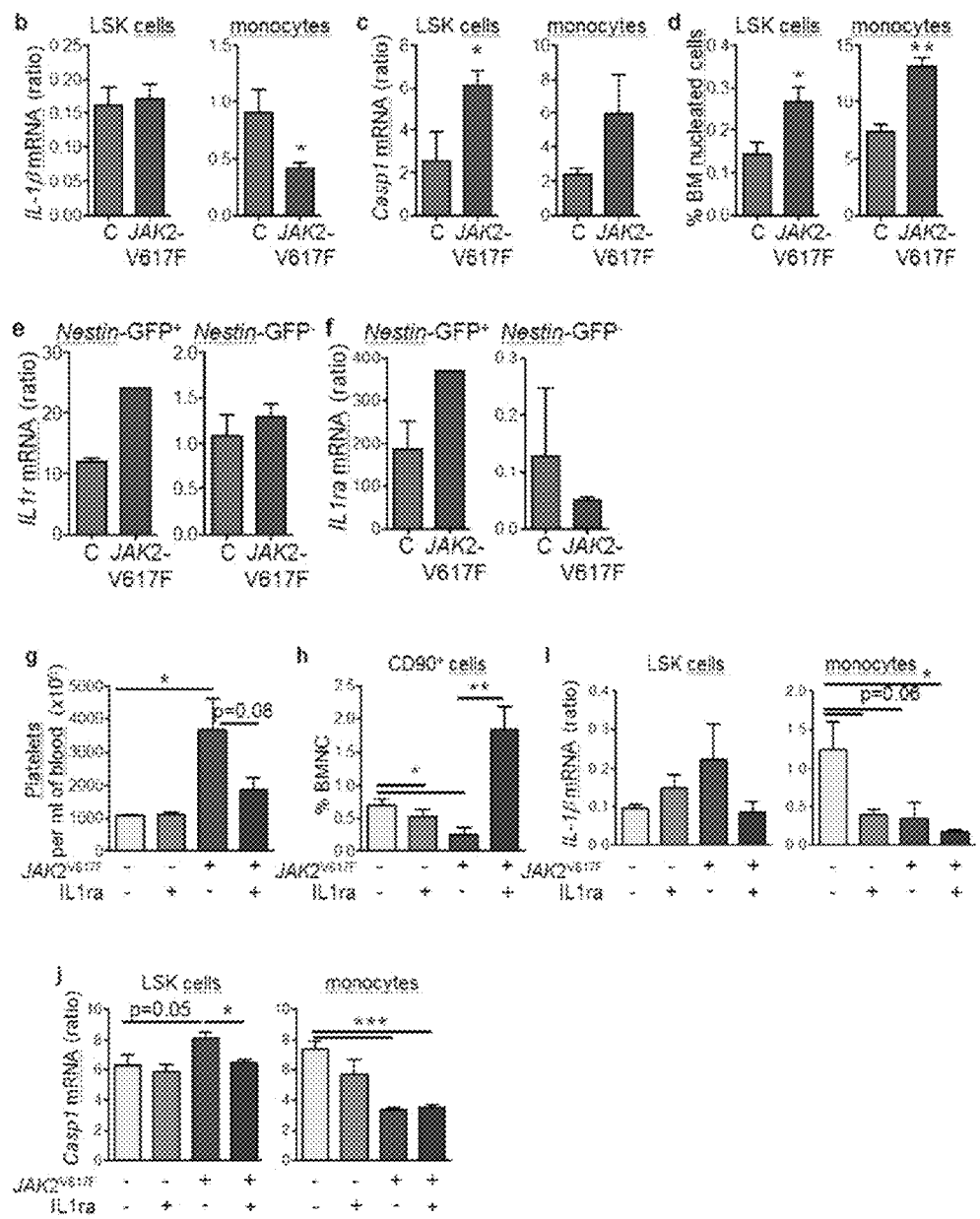

Sympathetic nerve fibres and ensheathing Schwann cells, adjacent to distinctive Nes-GFP+ cells, and GFAP mRNA expression were markedly reduced in BM of MPN patients and mice (FIG. 2c-g and FIG. 8g-i). Time course analysis showed that BM neural damage precedes Nes-GFP+ cell apoptosis (FIG. 2g), suggesting that sympathetic neuropathy could sensitise nestin+ cells to cell death triggered by mutant cells. Multiplex ELISA detected early increased interleukin-1β in MPN BM (FIG. 9a); this cytokine and its activating enzyme caspase-1 were expressed by monocytes, but also by haematopoietic progenitors (FIG. 9b-d). Compared with BM Nes-GFP− stromal cells, mRNA levels of interleukin-1 receptor and its antagonist were 10- and 1000-fold higher, respectively, and specifically upregulated in Nes-GFP+ cells in MPN (FIG. 9e-f).

Therefore the authors of the present invention chronically treated mice with an antagonist of interleukin-1 receptor. This treatment reduced platelet counts and increased BM MSC frequency, associated with reduced caspase-1 mRNA expression in haematopoietic progenitors (FIG. 2h and FIG. 9g-j). The authors studied whether JAK2V617F+ HSCs might directly cause BM Schwann cell death. Unlike MSCs, BM-derived Schwann cells co-cultured with JAK2V617F+ haematopoietic progenitors showed 3-fold higher apoptotic rate, which was blocked by interleukin-1 receptor antagonist (FIG. 2i).

Figure 3:
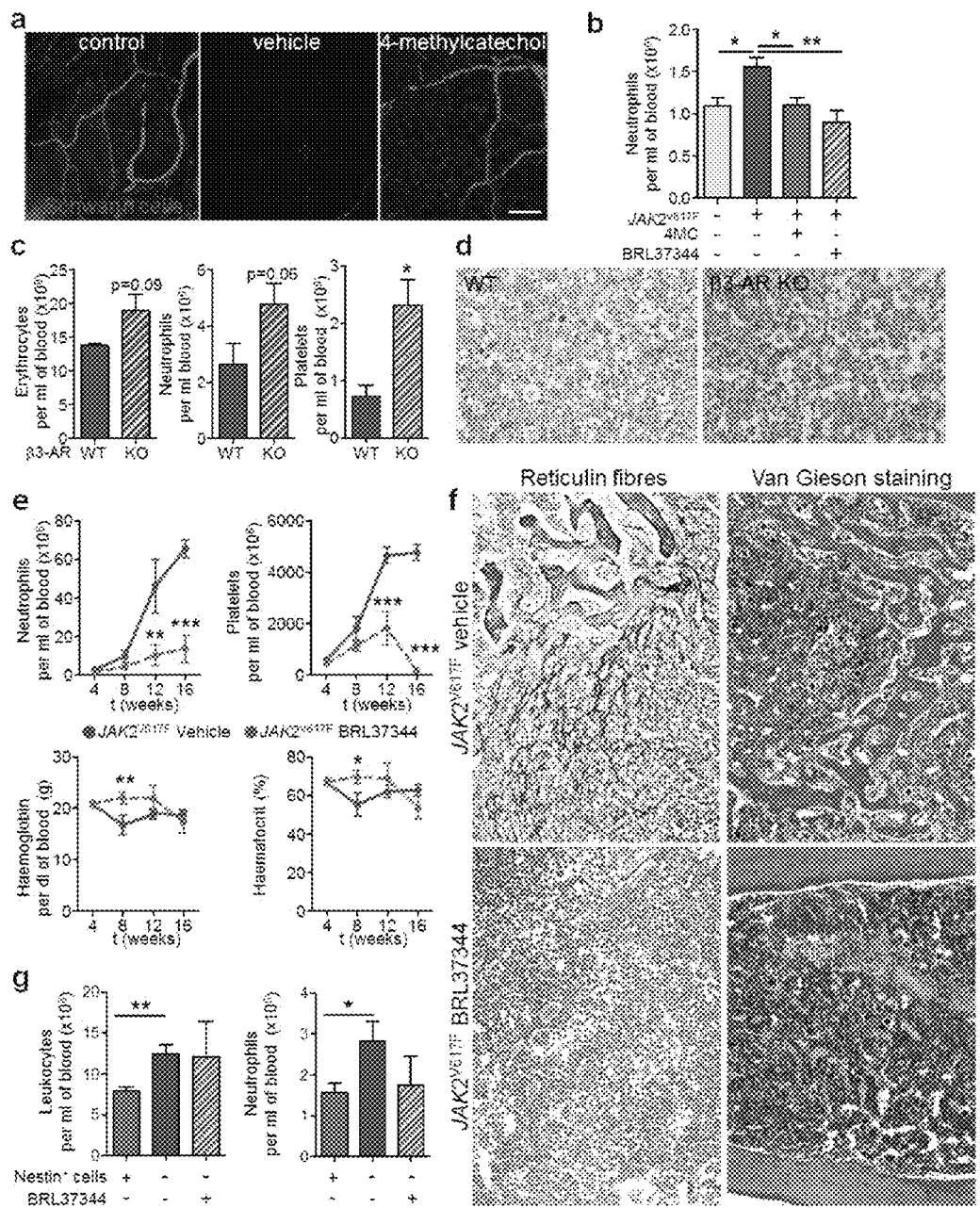
FIG. 3. Treatment with β3-adrenergic agonist or neuroprotective drug blocks MPN progression. a-b, Neurotrophic rescue of BM Schwann cells blocks MPN progression. WT mice transplanted with MPN BM cells were treated over a month with BRL37344, the neuroprotective drug 4-methylcatechol or vehicle. a, Skull BM immunostaining of glial fibrillary acidic protein to visualize Schwann cells (n=4-5); scale bar, 100 μm. b, Circulating neutrophils (n=5-9). c, Circulating erythrocytes, neutrophils and platelets 16 weeks after transplantation of MPN BM cells into β3-adrenergic receptor-deficient (KO) and WT mice (n=7-8). d, Van Gieson stainings of femoral BM of mice in (c). e-g, Compensation of BM sympathetic damage by selective sympathomimetic drugs blocks MPN progression and prevents fibrosis. e, Blood counts of WT mice transplanted with MPN BM cells and chronically treated with selective β3-adrenergic agonist (BRL37344) or vehicle (n=4-5). f, Reticulin and Van Gieson stainings of femoral BM of mice in (e) (magnification, 200×). g, In vivo depletion of nestin+ cells reduces the therapeutic effect of BRL37344. Blood counts of Nes13 creERT2;iDTA and control mice treated with vehicle or BRL37344 for 6 weeks (n=4-5). Drug treatments in a-b, e-f started 4 weeks after transplantation; treatment in g started 2 weeks after transplantation combined with tamoxifen (4 weeks). Mean±SEM. * p<0.05,  p<0.01, * p<0.001 (unpaired two-tailed t test).
Figure 4:
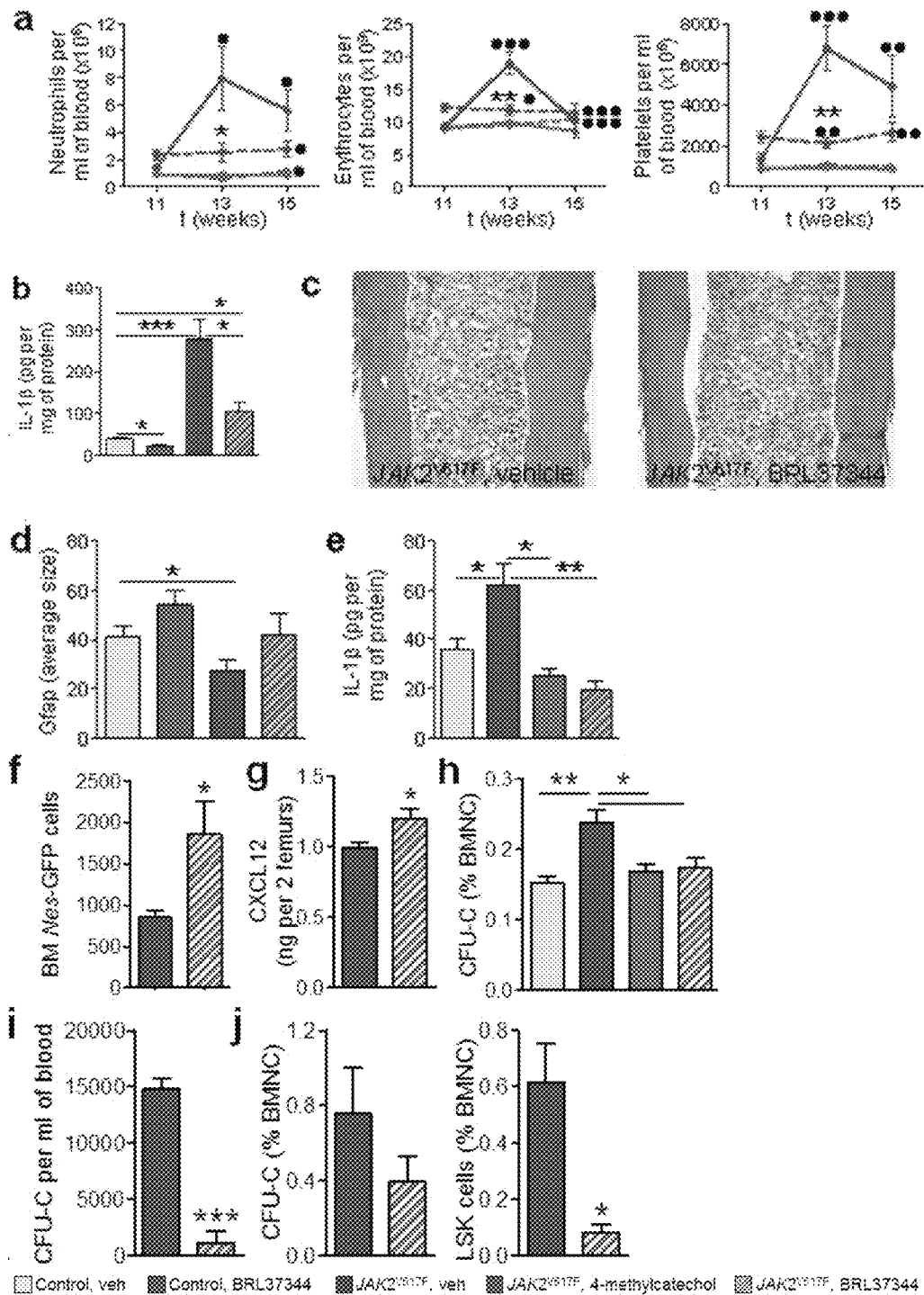
FIG. 4. Compensation of BM neuropathy rescues MSCs and prevents mutant HSC expansion in MPN. a-d, Efficacy of BRL37344 treatment in advanced MPN; WT mice transplanted with control or MPN BM cells were treated with BRL37344 or vehicle upon thrombocytosis (869±23 and 1968±264×106 platelets per ml of blood, respectively; n=4-5). a, Blood counts; * p<0.05,  p<0.01, * p<0.001 vs. vehicle-treated control mice. b, IL-1β content in BM supernatant. c, Van Gieson staining of femoral BM sections (magnification, 100×). d, Quantification of BM glial fibrillary acidic protein (Gfap) immunostaining. e-l, Sympathomimetic drug restores BM Cxcl12 levels and prevents HSC expansion and mobilisation. WT mice transplanted with control or MPN BM cells were treated 4 weeks with BRL37344, 4-methylcatechol or vehicle over (e, h) 4, (f) 8, or (g, i, j) 16 weeks. e, IL-1β content in BM supernatant (n=5-11). f, BM CD45−CD31−Ter119−Nes-GFP+ cells (n=8-10). g, Cxcl12 content in BM supernatant. h-j, Frequency of colony-forming units (CFU-C) in (h, j) BM nucleated cells (BMNC) and (i) blood, and (j) BM fraction of lin-sca-1+c-kit+ (LSK) cells (n=3-5). k, LSK cells, long-term (LT−) and short-term (ST−) HSCs (n=4-5) in mice in (a-d). l, Reduction of leukaemic stem cells in BRL37344-treated mice. CD45.2 WT mice were transplanted with BM cells from CD45.1 mice and limited BM cells from MPN mice treated with vehicle or BRL37344 (n=5). Frequency of mice with <50% donor LSK cell chimerism 16 weeks after transplantation is plotted against tested cell number. MPN-initiating cell frequency is indicated. * p<0.05, Pearson chisquared t test. m, Model illustrating HSC niche alterations and rescue in MPN. MPN, myeloproliferative neoplasm; HSC, haematopoietic stem cell; SNS, sympathetic nervous system; MSC, mesenchymal stem cell; NA, noradrenaline; AR, adrenergic receptor; C, control (disease-free mice). a-k, Mean±SEM. * p<0.05,  p<0.01, * p<0.001 (unpaired two-tailed t test).
Figure 4:
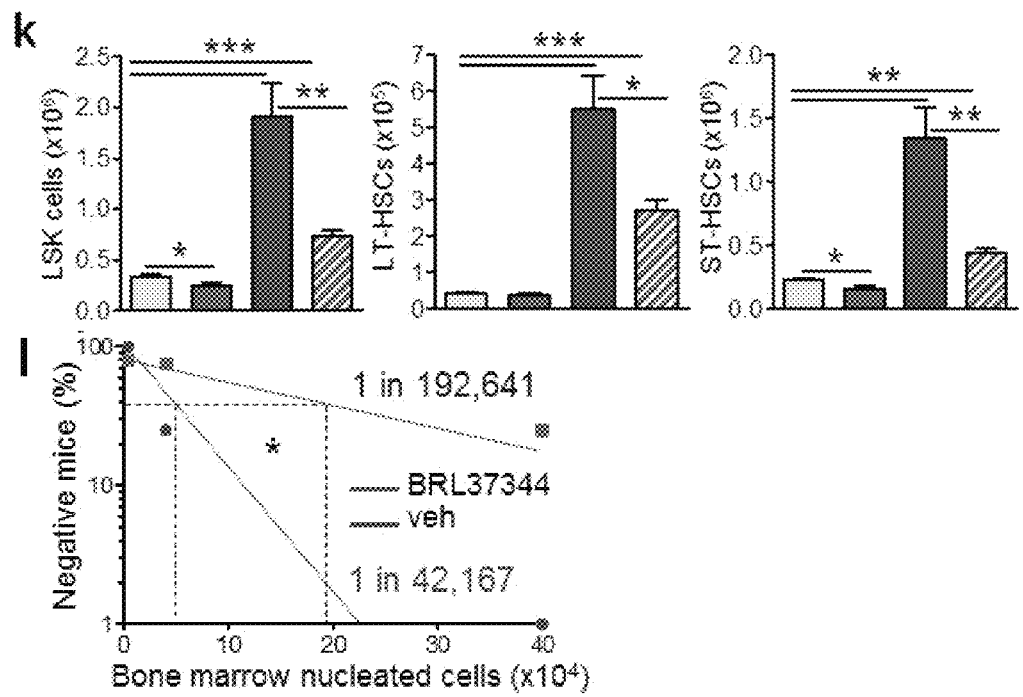
Figure 4:
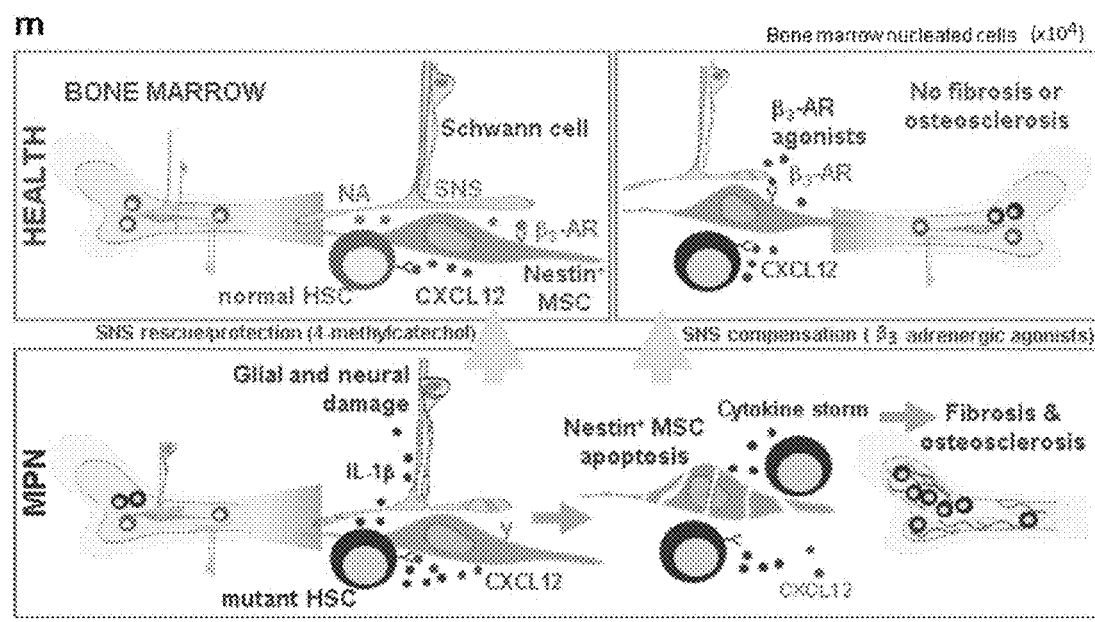
Figure 5:
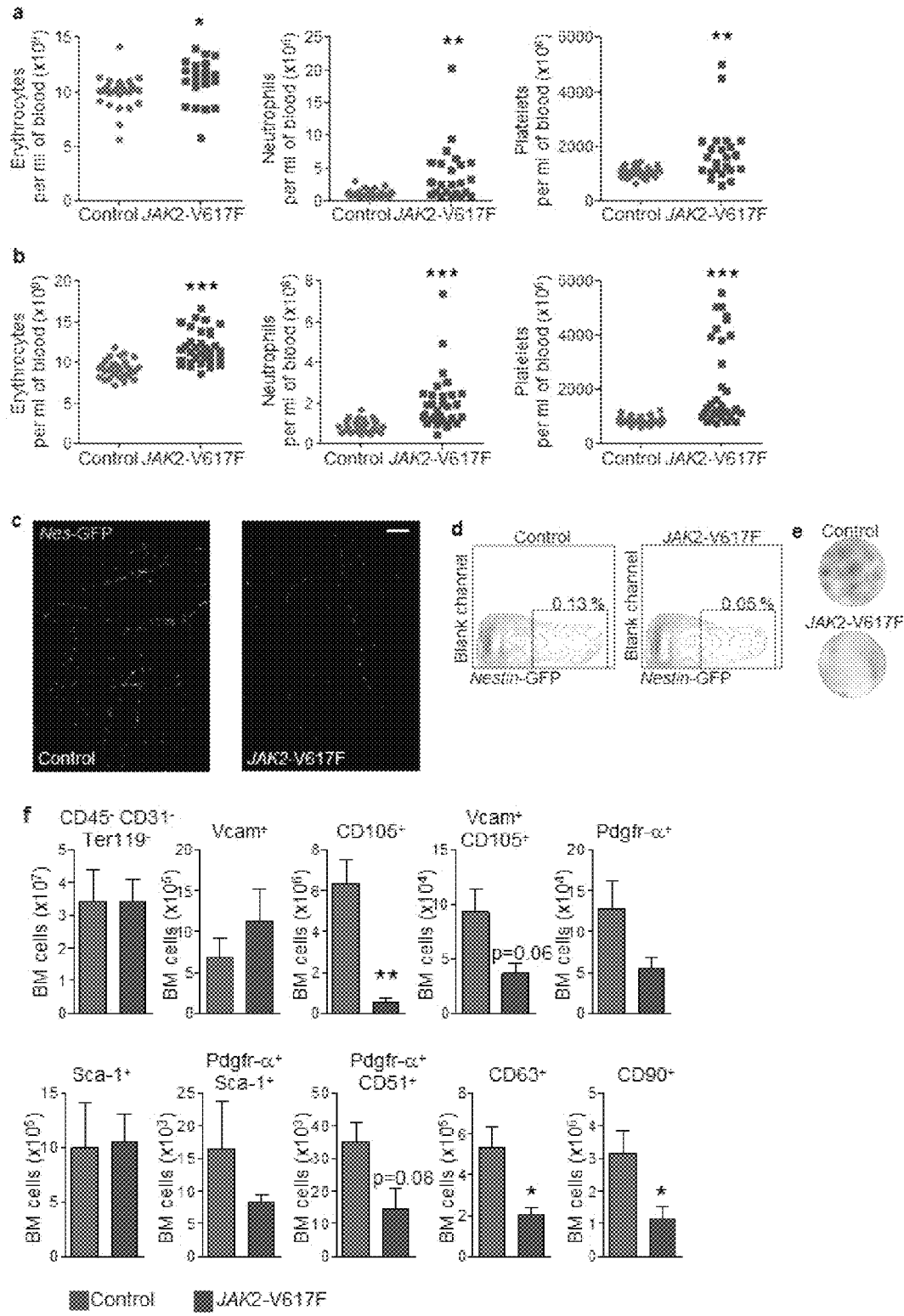
FIG. 5. BM MSC reduction in compound mutant mice and recipients of mutant haematopoietic cells is not due to cell differentiation. a-b, Blood counts of (a) Nes-gfp;Mx1-cre;JAK2-V617F and control mice 4-8 weeks after plpC treatment and (b) Nes-gfp mice 10-12 weeks after transplantation with BM cells from MPN and control mice. Note the similar erythrocytosis, neutrophilia and thrombocytosis in compound mutant mice and Nes-gfp mice transplanted with mutant cells. Each dot represents a mouse. c, GFP fluorescence in skull BM of Nes-gfp mice 6-8 weeks after transplantation with MPN and control BM cells (scale bar, 100 μm). d, Frequency of CD45−CD31−Ter119−Nes-GFP+ BM cells in MPN and control mice (n=7-9) 6-8 weeks after plpC induction. e, Giemsa-stained fibroblastic colony-forming units (CFU-F) from immunomagnetically-enriched BM CD45−Ter119− cells 30 weeks after transplantation with MPN and control BM cells. f, FACS analyses of BM CD45−CD31− Ter119− cells from MPN and control mice 8 weeks after plpC treatment (n=3). The specified MSC markers were used. Mean±SEM. g, BM reticulin staining; MPN mice showed incipient fibrosis (arrow) 6 weeks after plpC treatment (magnification, 200×). h-i, Lineage-tracing studies of BM nestin+ cells in MPN. h, Experimental design. NescreERT2; RCE:loxP mice were transplanted with MPN and control BM cells and fed with tamoxifen diet. Disease development was monitored over 28 weeks. i, Blood counts showing progressive neutrophilia and thrombocytosis in recipients of MPN BM cells (n=3). j, Femoral haematoxilin and eosin stainings showing abnormal bone formation in recipients of MPN BM cells (magnification, 100×). * p<0.05,  p<0.01, * p<0.001 (unpaired two-tailed t test).
Figure 5:
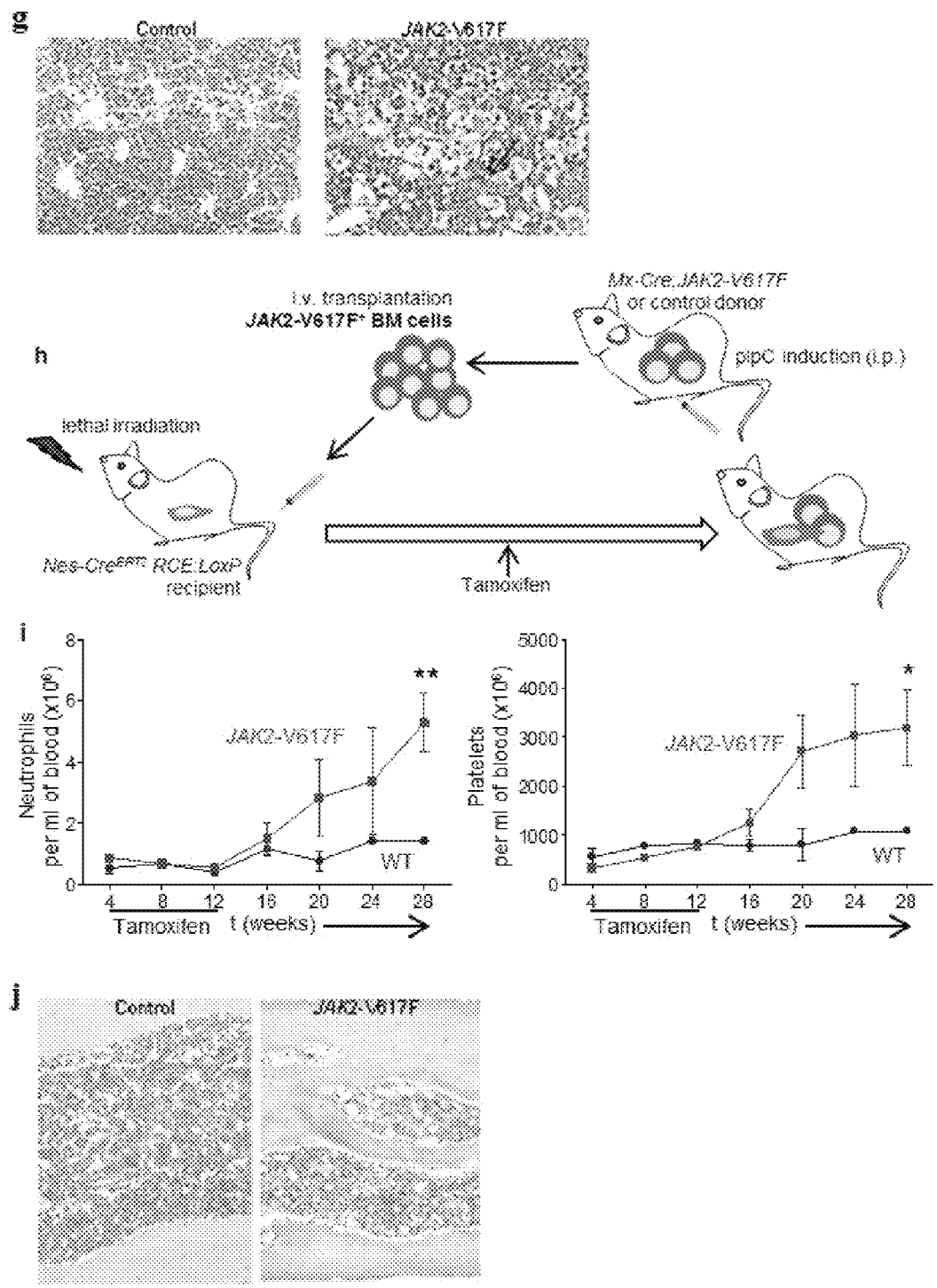
Figure 10:
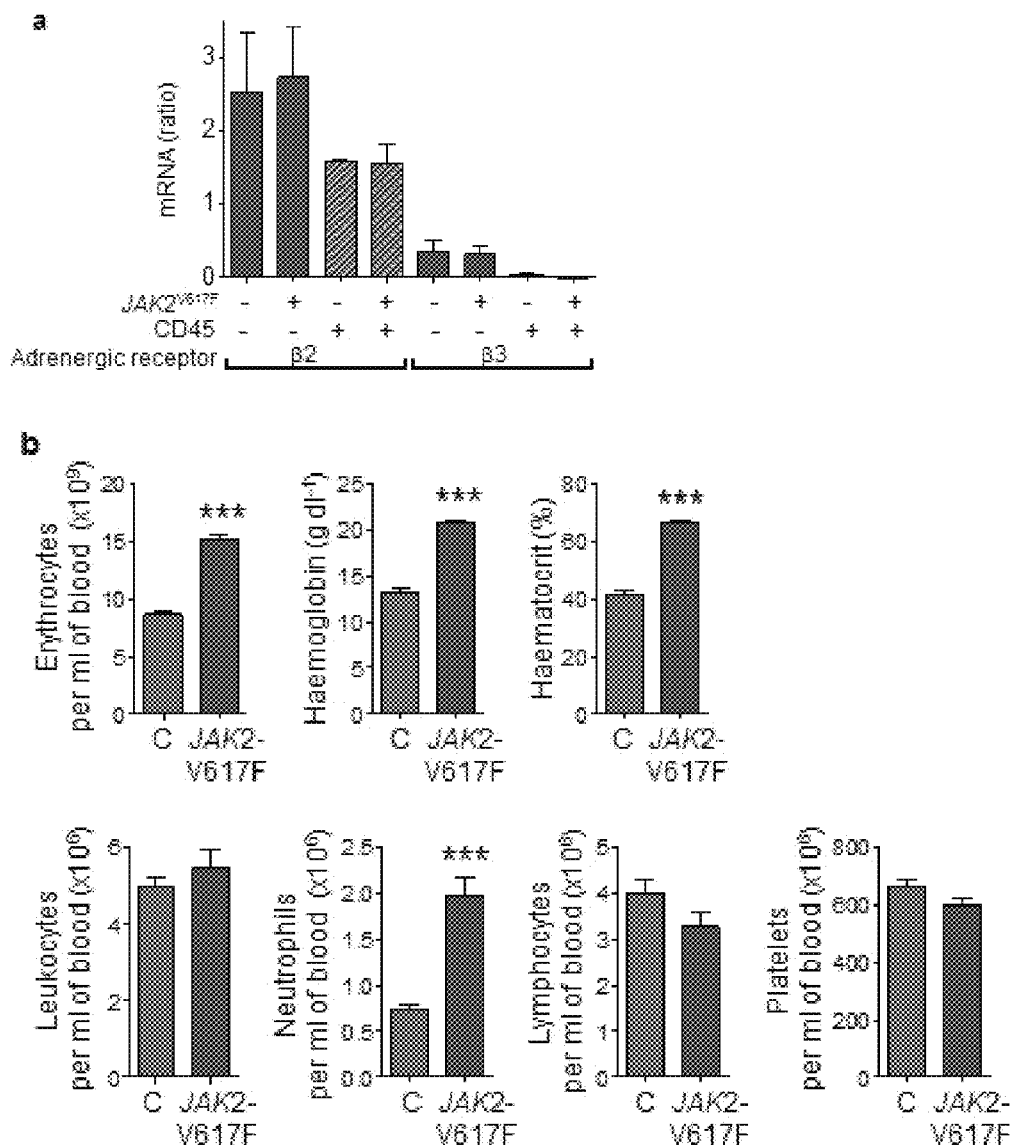
FIG. 10. Compensatory treatment with β3-adrenergic agonist BRL37344 blocks MPN progression. a, Expression of β2- and β3-adrenergic receptors in immunomagnetically-enriched CD45+ and CD45− BM cells from control and plpC induced Mx1-cre;JAK2-V617F mice (n=3). b-c, Blood counts of WT mice (b) 4 weeks after transplantation with MPN or control BM cells, prior to (n=11-13) and (c) 4-12 weeks after chronic BRL37344 (2 mg kg-1) or vehicle treatment (i.p., twice a day separated 10-12 hours; n=4-5). CD11b+ monocytes and granulocytes, B220+ B cells and CD3+ T cells were determined by flow cytometry. d, Blood counts of WT mice transplanted with control BM cells and treated with BRL37344 or vehicle as described above (n=4-6). Mean±SEM. * $p<0.05$,  $p<0.01$, * $p<0.001$ (unpaired two tailed t test).
Figure 10:
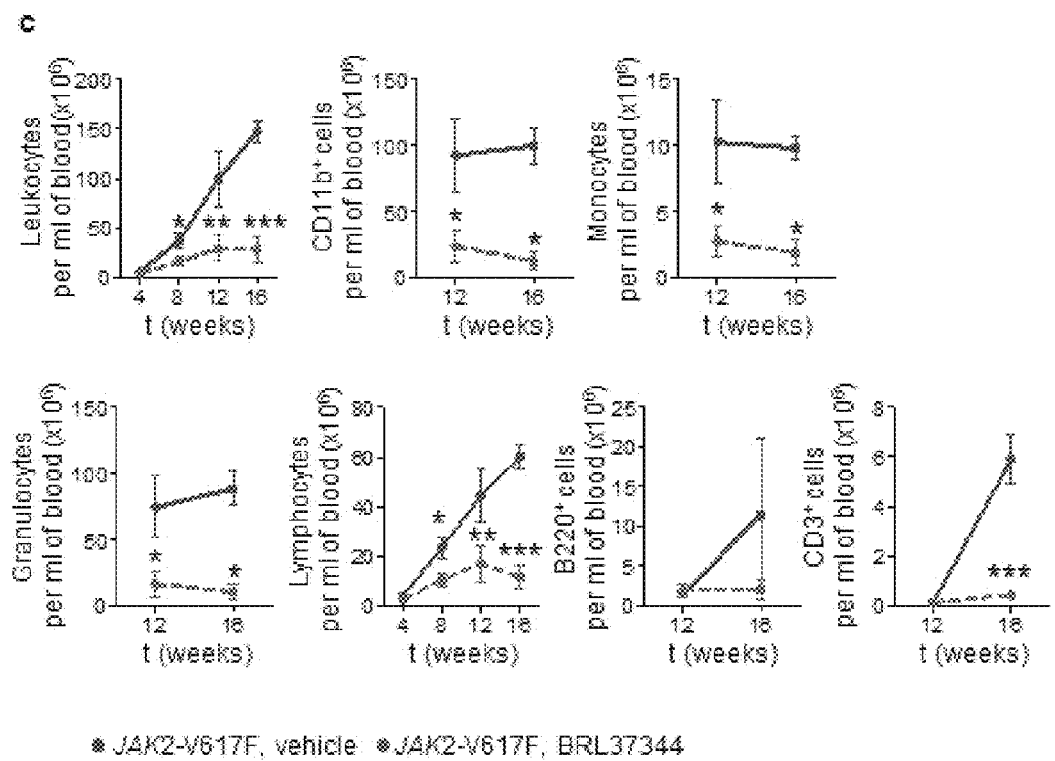
Figure 10:
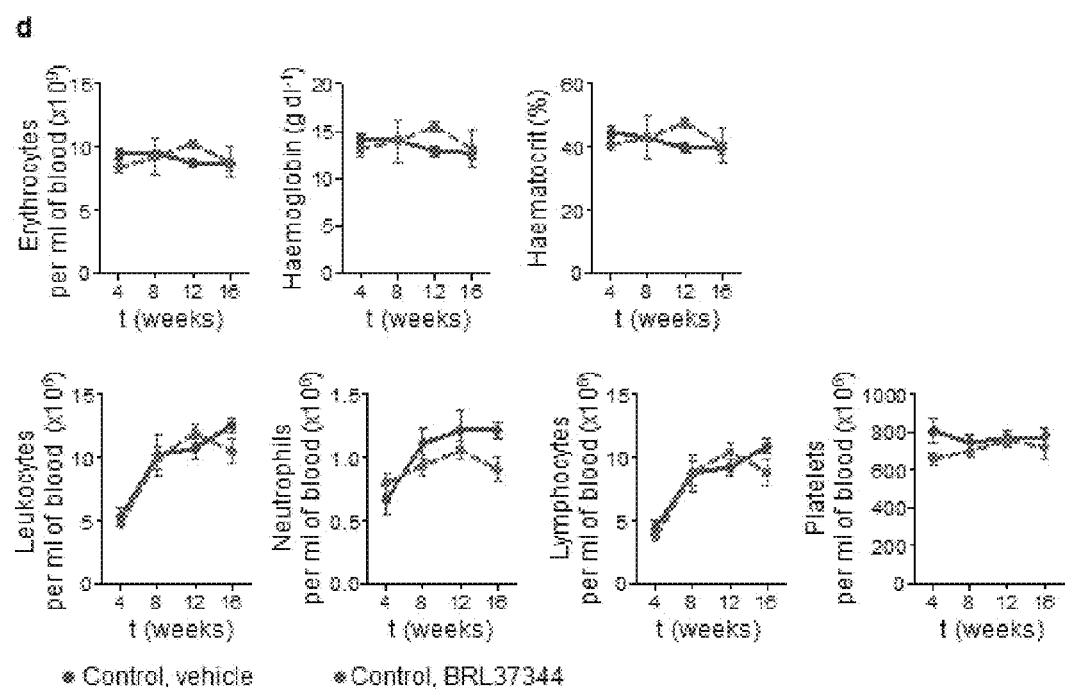

Together, these data suggest that HSC-derived interleukin-1 contributes to neuroglial damage, which compromises MSC survival. The authors therefore investigated whether sympathetic neuropathy might underlie HSC niche alterations and thus represent a therapeutic target in MPN. In this sense, the authors treated symptomatic MPN mice with the neuroprotective agent 4-methylcatechol, which can protect BM sympathetic nerve fibres during chemotherapy. Schwann cells were preserved in 4-methylcatechol-treated mice, associated with prevented neutrophilia (FIG. 3a-b). Sympathetic nerve fibres regulate BM HSC traffic via β3-adrenergic receptor activation in nestin+ MSCs. This receptor is not expressed in normal or JAK2V617F+ haematopoietic cells (FIG. 10a). Disease development was accelerated in mice lacking β3-adrenergic receptor (FIG. 3c-d), uncovering a protective role of this receptor in MPN. Symptomatic mice were chronically treated with a selective β3-adrenergic agonist (BRL37344) to compensate for deficient sympathetic stimulation of nestin+ MSCs. Strikingly, BRL37344 treatment prevented MPN-associated neutrophilia and thrombocytosis, delayed red blood cell reduction but did not affect blood counts in wild-type mice (FIG. 3b, e and FIG. 10b-d). Contrasting the severe fibrosis in vehicle-injected mice, the BM of BRL37344-treated animal was virtually devoid of excessive bone and fibroblastic tissue (FIG. 3f).

Figure 11:
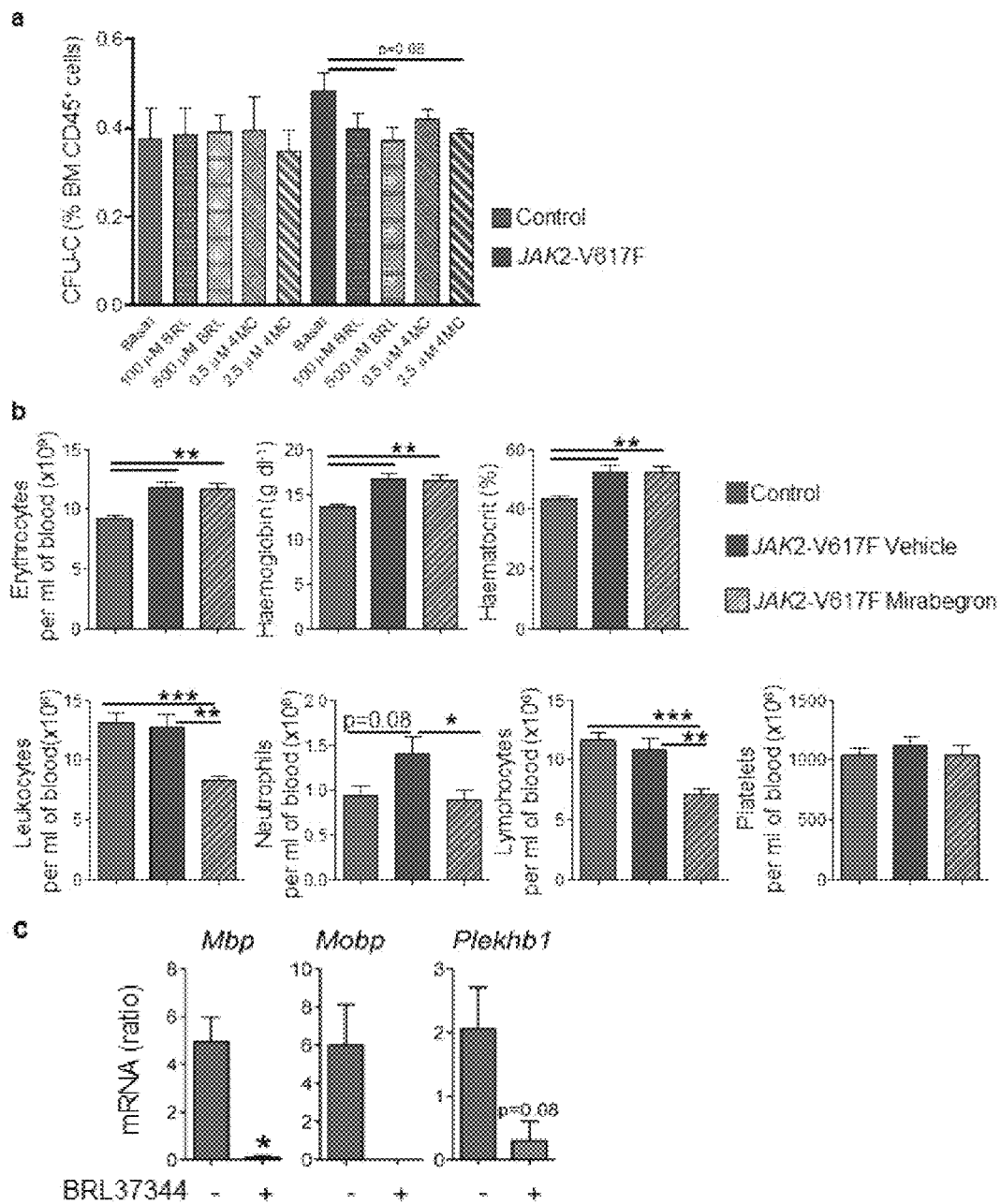
FIG. 11. β3-adrenergic agonists or neuroprotective drugs prevent neuroglial gene induction in nestin+ cells and indirectly affect mutant haematopoietic cells. a, Inhibition of mutant HSC expansion by β3-adrenergic agonists or neuroprotective drugs is HSC-niche dependent. Immunomagnetically-enriched CD45+ haematopoietic cells were obtained from the BM of Nes-gfp;Mx1-cre;JAK2− V617F mice and control littermates 16 weeks after plpC treatment (n=3). BRL37344 (BRL) and 4-methylcatechol (4MC) were added in vitro at the indicated concentrations and the frequency of colony-forming units in culture (CFU-C) was scored after one week in culture. b, Compensatory treatment with the human (33-adrenergic agonist Mirabegron delays MPN in mice. Blood counts of WT mice 8 weeks after transplantation with MPN or control BM cells. Mirabegron (2 mg kg-1) or vehicle treatment (i.p., twice a day separated 10-12 hours) was administered the last two weeks (n=5-8). c, BM Nes-GFP+ cells from MPN mice treated with BRL37344 do not express neuroglial genes; mRNA expression of the Schwann cell markers myelin basic protein (Mbp), myelin-associated oligodendrocyte basic protein (Mobp) and pleckstrin homology domain containing, family B (evectins) member 1 (Pleckhb1) in BM CD45− CD31− Ter119−GFP+ cells sorted from Nes-gfp mice treated over 8 weeks with BRL37344 or vehicle, starting 4 weeks after transplantation with MPN or control BM cells (n=4). Mean±SEM. * $p<0.05$,  $p<0.01$, * $p<0.001$ (unpaired two-tailed t test).

These effects were HSC niche-dependent, since neither 4-methylcatechol nor BRL37344 affected the growth of cultured haematopoietic progenitors and leukocytosis was not rescued by BRL37344 in mice depleted in nestin+ cells (FIG. 3g and FIG. 11a). Similarly, several MPN markers were improved by treatment with the clinically-approved β3-adrenergic agonist Mirabegron (FIG. 11b), albeit to lower extent probably due to its poor solubility and relatively low affinity for the murine receptor.

To investigate the potential therapeutic benefit when administered at more advanced stages, thrombocytotic and control mice were treated with BRL37344. This treatment reduced neutrophilia, erythrocytosis, thrombocytosis, BM interleukin-1β, fibrosis and osteosclerosis, rescued BM Schwann cells (FIG. 4a-d) and blocked Schwann cell program activation in BM nestin+ cells (FIG. 11c). MPN progression can thus be blocked by protection or rescue of BM neuroglia and by compensation of deficient sympathetic stimulation of nestin+ MSCs by β3-adrenergic agonists.

Figure 12:
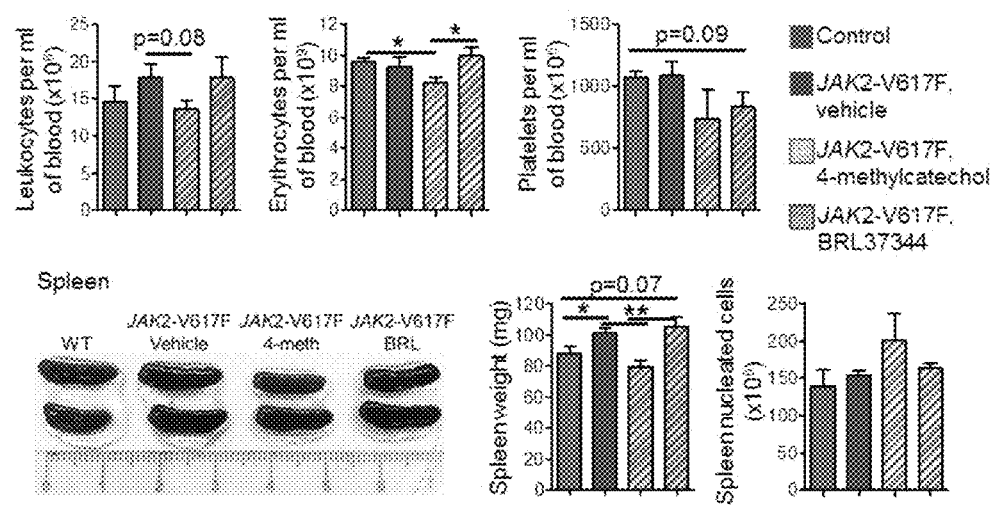
FIG. 12. Incipient MPN signs are improved by BRL37344 or 4-methylcatechol. a-b, Haematological parameters of WT mice 8 weeks after transplantation with BM cells from plpC-treated control and Mx1-cre;JAK2-V617F mice. The latter received the neuroprotective drug 4-methylcatechol (10 μg kg-1, once daily), BRL37344 (2 mg kg-1) or vehicle injections (twice a day, separated 10-12 hours) for the last 4 weeks (i.p.; n=4-5). MPN progression was monitored in peripheral blood and mice were sacrificed when they showed only incipient symptoms. a, Blood counts, spleen size, weight and nucleated cell number, BM nucleated cells (limbs and sternum), CD11b+ myeloid, B220+B-lymphoid and CD3+ T cells. b, BM lin-sca-1+c-kit+ (LSK) haematopoietic progenitors, Ter119+CD71-mature erythroblasts and CD41+/CD42+ megakaryocyte progenitors. Mean±SEM. * $p<0.05$,  $p<0.01$, * $p<0.001$ (unpaired two-tailed t test).
Figure 12:
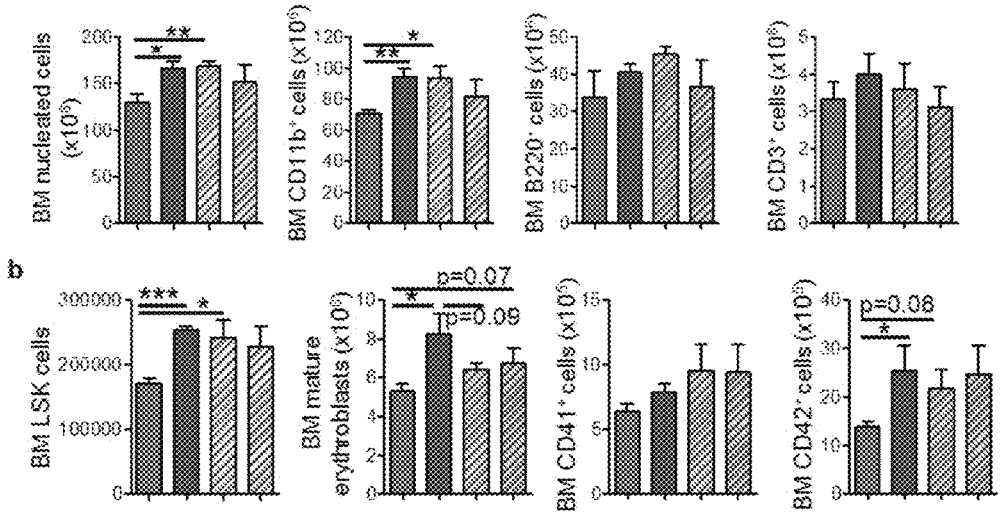
Figure 13:
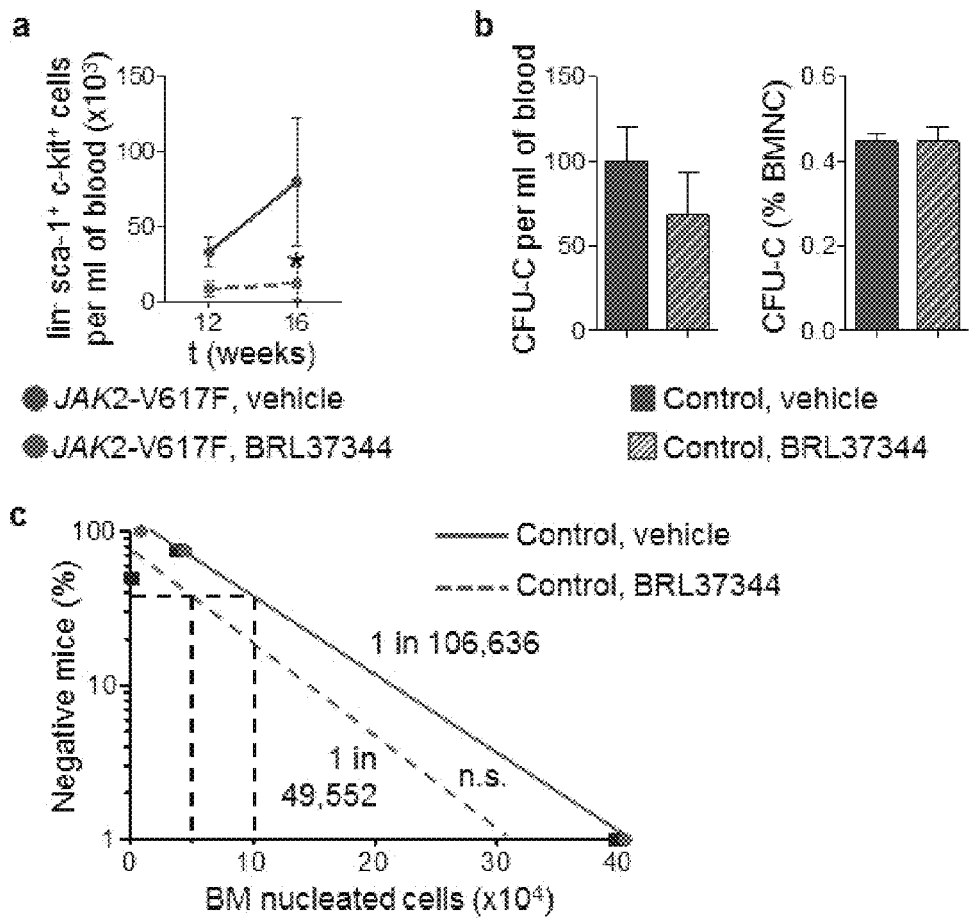
FIG. 13. Long-term BRL37344 treatment inhibits JAK2-V617F+HSC expansion but does not compromise normal haematopoiesis. Haematopoietic progenitors quantitated by (a) FACS or (b) colony-forming units (CFU-C) in BM and blood of WT mice 12-16 weeks after transplantation with (a) MPN and (b) WT BM cells, 16 weeks after BRL37344 (2 mg kg-1) or vehicle injections (twice a day, separated 10-12 hours; i.p.; n=3). Mean±SEM. * p<0.05 (unpaired two-tailed t test). c, BRL37344 treatment does not change normal HSC BM number. CD45.2 WT mice were transplanted with BM cells from congenic CD45.1 WT mice, together with limiting numbers of BM cells from CD45.2 control mice treated with vehicle/BRL37344 over 4 weeks, starting 11 weeks after the transplant (n=5). The frequency of mice that failed reconstitution 16 weeks after transplantation is plotted against the number of tested cells. HSC frequencies are indicated; n.s., non-significant; Pearson chi-squared t test.

The authors next asked whether MPN blockade could be mediated by preservation of MSCs and their HSC regulatory function. BRL37344 reduced IL-1β, restored Nes-GFP+ cell number and increased Cxcl12 levels in BM (FIG. 4e-g). Early BRL37344 or 4-methylcatechol treatments prevented mutant haematopoietic progenitor expansion (FIG. 4h and FIG. 12). Long-term BRL37344 treatment did not compromise normal HSCs but efficiently decreased mutant haematopoietic progenitors (FIG. 4i-j and FIG. 13), even when administered at thrombocytotic stage (FIG. 4k). Moreover, BRL37344-treated MPN mice showed 4.5-fold reduction in leukemic stem cells (FIG. 4l).

The present findings thus point to mutant HSCs as the cause of BM neuroglial damage that compromises MSC survival and function, critically contributing to MPN pathogenesis (FIG. 4m). In this sense, the present invention shows that the niche damage triggered by the mutant HSC is essential for the development of a haematopoietic malignancy previously considered to be caused by the HSC alone.

Targeting HSC niche-forming MSCs and their neural regulation paves the way to more efficient therapeutic strategies in MPN. For this purpose, the present invention shows that an efficient therapeutic strategy for the treatment of MPN lies on the administration of neuroprotective compounds, such as 4-methylcatechol, capable of protecting BM sympathetic nerve fibres. Additionally, another efficient therapeutic strategy is shown herein as the administration of selective β3-adrenergic agonists such as BRL37344 or Mirabegron, since this strategy will compensate for deficient sympathetic stimulation of nestin+ MSCs.

Therefore, a first aspect of the present invention refers to a composition comprising a TrK or RET receptor agonist, preferably a β3-adrenergic agonist, more preferably a selective β3-adrenergic agonist, or a neuroprotective compound capable of protecting BM sympathetic nerve fibres or the combination thereof, for its use in the treatment of myeloproliferative neoplasms. Preferably, the myeloproliferative neoplasms are selected from the group consisting of chronic myeloid leukaemia (CML), Chronic myelomonocytic leukaemia (CMML), polycythaemia vera, essential thrombocythaemia, primary myelofibrosis, Idiopathic myelofibrosis, agnogenic myeloid metaplasia, chronic neutrophilic leukaemia, chronic eosinophilic leukaemia and mastocytosis.

For the sake of simplicity, "selective β3 agonist", "selective beta-3 agonist" or similar expressions are used herein to refer to a "selective beta-3 adrenergic receptor agonist".

Generally, an agonist is a molecule that binds to the receptor and has an intrinsic effect, and therefore increases the basal activity of a receptor when it comes into contact with the receptor. In the present invention, selective beta-3 adrenergic receptor agonist is understood as a compound that exhibits preferential agonism towards the beta-3 receptor compared to the beta-1 and beta-2 receptors. Therefore the selective beta-3 agonists behave like beta-3 receptor agonists at lower concentrations than for beta-1 and beta-2 receptors. A selective beta-3 agonist also includes compounds that behave like beta-3 receptor agonists and like beta-1 and beta-2 receptor antagonists.

Preferably, the selectivity of the useful compounds in the present invention towards the beta-3 receptor is clearly higher compared to beta-1 and beta-2 receptors. In a preferred embodiment, the selective β3 agonists according to the present invention show selectivity towards the beta-3 receptor that is 25 about ≥10 times higher, more preferably about ≥100 times higher, and still more preferably about ≥1000 times higher, with respect to other beta adrenergic receptors. Even more preferably for the purpose of the invention, selective β3 agonists show selectivity towards the beta-3 receptor that is "infinitely" higher (about 30≥10000 times) with respect to other beta adrenergic receptors.

In preferred particular embodiments, the selective β3 agonist shows inhibition constant and/or mean effective concentration values for β3, β1 and β2 receptors, respectively, of about Ki 287/1750/1120 nM and/or EC50 18/>10000/>10000 nM. The capability of a specific compound to exert selective beta-3 agonism can be easily evaluated by means of conventional techniques. General literature references related to receptor ligand-binding assays include, for example: Masood N. Khan, John W. Findlay (2010). Ligand-Binding Assays: Development, Validation, and Implementation in the Drug Development Arena: John Wiley & Sons; Assay Guidance Manual Version 5.0, 2008: Eli Lilly and Company and NIH Chemical Genomics Center, available at: http://ncgcweb.nhgri.nih.gov/guidance/manual_toc.html.

Representative examples of selective beta-3 agonists useful in the present invention include, but are not limited to:
BRL 37344
CL 316243
AZ 002
BMS 187257
L-755507
L-750355
FR-149175
GW427353 (Solabegron)
YM178 (Mirabegron/myrbetriq)
CR 58611
SR 58611A (Amibegron)
SR 59104$^a$
SR 59119A
SAR150640
L-796568
CL-316243
and their pharmaceutically acceptable salts.

Any compound to which reference is made herein seeks to represent such specific compound as well as certain variations or forms. Therefore the useful compounds in the present invention can be, for example, in neutral form, in the form of a base or acid, in the form of a salt, preferably a physiologically acceptable salt, in the form of a solvate or of a polymorph and/or in different isomeric forms.

The term "salt" must be understood as any form of an active compound used according to this invention in which said compound is in ionic form or is charged and coupled to a counterion (a cation or anion) or is in solution. This definition also includes quaternary ammonium salts and active molecule complexes with other molecules and ions, particularly complexes formed by means of ionic interactions. The definition particularly includes physiologically acceptable salts; this term must be understood as equivalent to "pharmacologically acceptable salts" or "pharmaceutically acceptable salts".

The expression "physiologically acceptable salt" or "pharmaceutically acceptable salt" is particularly understood in the context of this invention as a salt (as defined above) formed either with a acid that is physiologically tolerated, i.e., salts of the particular active compound with organic or inorganic acids that are physiologically tolerated, particularly if they are used in human beings and/or mammals, or with at least one cation, preferably an inorganic cation, that is physiologically tolerated, particularly if they are used in human beings and/or mammals. Examples of particular acid salts that are physiologically tolerated are: hydrochloric acid, hydrobromic acid, sulfuric acid, hydrobromide, monohydrobromide, monohydrochloride or hydrochloride, methiodide, methanesulfonic acid, formic acid, acetic acid, oxalic acid, succinic acid, malic acid, tartaric acid, mandelic acid, fumaric acid, lactic acid, citric acid, glutamic acid, hippuric acid, picric acid and/or aspartic acid salts. Examples of particular base salts that are physiologically tolerated are alkali metal and alkaline-earth metal salts and with NH4.

According to this invention, the term "solvate" must be understood to mean any form of the active compound according to the invention in which this compound binds to another molecule (usually a polar solvent) by means of a non-covalent bond, particularly including hydrates and alcoholates, such as methanolate, for example.

Also within the scope of the invention is any compound which is a prodrug of a selective beta-3 adrenergic receptor agonist. The term "prodrug" is used in the broadest sense of the word and covers those derivatives converted into the compounds of the invention in vivo. Examples of prodrugs include, but are not limited to, derivatives and metabolites of selective beta-3 agonist compounds, including biohydrolyzable residues such as biohydrolyzable amides, biohydrolyzable esters, biohydrolyzable carbamates, biohydrolyzable carbonates, biohydrolyzable ureides and biohydrolyzable phosphate analogues. Prodrugs of compounds with functional carboxyl groups are preferably lower alkyl esters of carboxylic acid. Carboxylate esters are suitably formed by esterifying any of the carboxylic acid residues present in the molecule. Prodrugs can usually be prepared using well-known methods, such as those described in Burguer "Medicinal Chemistry and Drug Discovery 6th ed." (Donald J. Abraham ed. 2001, Wiley), "Design and Applications of Prodrugs" (H. Bundgaard ed., 1985, Harwood Academic Publishers) and Krogsgaard-Larsen et al. "Textbook of Drug Design and Discovery" Taylor & Francis (April 2002).

Selective beta-3 agonists useful in the present invention can include optical isomers depending on the presence of chiral centers or geometric isomers depending on the presence of multiple bonds (for example Z, E). Individual isomers, enantiomers or diastereoisomers and mixtures thereof, such as a racemic mixture are within the scope of the present invention.

Furthermore, any compound to which reference is made herein can exist as tautomers. Specifically, the term tautomer refers to one of two or more structural isomers of a compound in equilibrium and easily converted from one isomeric form to another. Common tautomeric pairs are amine-imine, amide-imidic acid, keto-enol, lactam-lactim, etc.

Unless otherwise indicated, it also is understood that the compounds of the invention include isotopically labeled forms, i.e., compounds differing only by the presence of one or more isotopically enriched atoms. For example, compounds having the present structures except the substitution of at least one hydrogen atom with a deuterium or tritium atom, or the substitution of at least one carbon with a 13C- or 14C-enriched carbon, or the substitution of at least one nitrogen with 15N enriched nitrogen, are within the scope of this invention.

Selective beta-3 agonists in the context of the invention are preferably in a pharmaceutically acceptable or substantially pure form. Pharmaceutically acceptable form is understood, among others, to have a pharmaceutically acceptable purity level excluding typical pharmaceutical additives such as diluents and vehicles, and to not include any material considered toxic at normal dosage levels. Purity levels with respect to the active ingredient are preferably greater than 50%, more preferably greater than 70%, most preferably greater than 90%. In a preferred embodiment, it is greater than 95% selective beta-3 agonist.

As observed above, the expression "pharmaceutically acceptable prodrugs, solvates or salts" refers to any salt, solvate or any other compound which, after administration to the recipient, can (directly or indirectly) provide a selective beta-3 agonist. It will be observed that non-pharmaceutically acceptable prodrugs, solvates and salts are also within the scope of the invention given that they can be useful in preparing pharmaceutically acceptable prodrugs, solvates and salts. Prodrugs, solvates and salts can be prepared by means of methods known in the art.

In a particular embodiment of the invention, the selective beta-3 agonist is selected from a compound derived from phenylethanolamine (2-amino-1-phenylethanol).

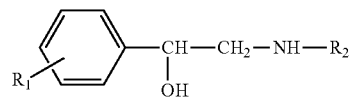

wherein R1 and R2 can represent various meanings, as detailed below.

In a more particular embodiment, R1 is selected from hydrogen and halogen (F, Cl, Br or I); the halogen is preferably chlorine. R1 can be in any position (ortho, meta or para); in a preferred embodiment, R1 is in the meta position.

In another more particular embodiment, R2 is an aralkyl, being able to be substituted in the aryl part and/or in the alkyl part, or a radical selected from:

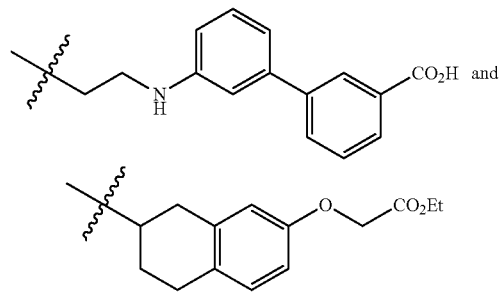

Particular $R_2$ radicals are indicated below:

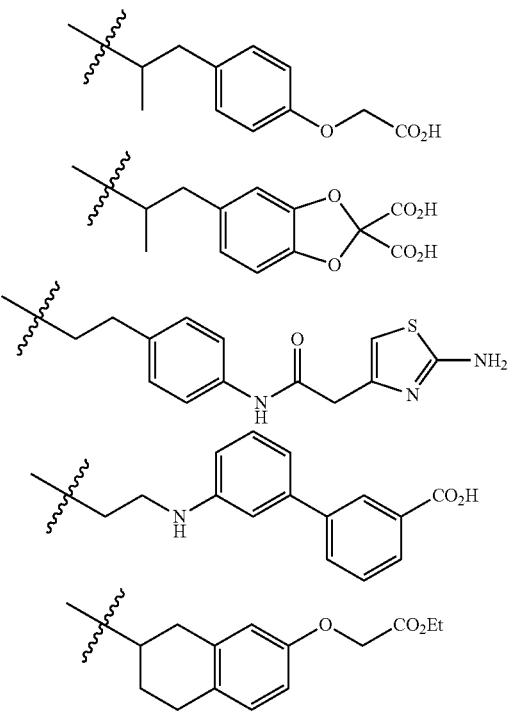

In a preferred embodiment, R1 represents chlorine in meta position and R2 is an optionally phenyl-substituted 1-methyl-2-phenylethyl radical. In another preferred embodiment, R1 represents hydrogen and R2 is an optionally phenyl-substituted 2-phenylethyl radical. In a preferred embodiment, the agonist used in the present invention is the compound identified as BRL37344 ([4-[(2R)-2-[[(2R)-2-(3-clorophenyl)-2-hydroxyethyl]amino]propyl]phenoxy]acetic acid), which is described in documents EP 023 385 and in Drugs of the Future, Vol. 16, 797-800 (1991), and it has the following molecular formula:

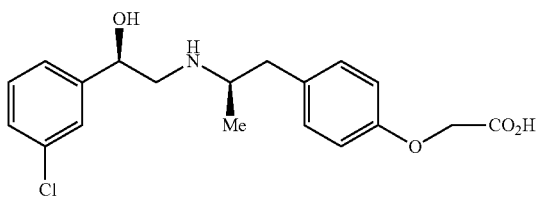 [SMILES: C[C@H](Cc1ccc(OCC(=O)O)cc1)NC[C@H](O)c1cccc(Cl)c1]

Compound BRL 37344 is a potent and selective beta-3 adrenergic receptor agonist (Ki values are 287, 1750 and 1120 nM for β3, β1 and β2 receptors, respectively) which can be commercially acquired in the form of sodium salt (CAS number 5 127299-93-8):

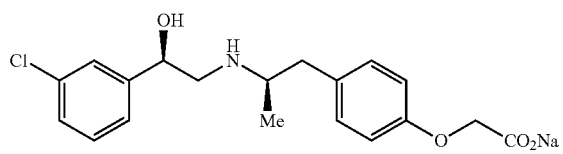

In another embodiment of the invention, the compound known as CL316243 is preferred, said compound being described in documents EP 0 455 006 and J. Med. Chem., Vol. 35, 3081-3084 (1992) and having the following molecular formula:

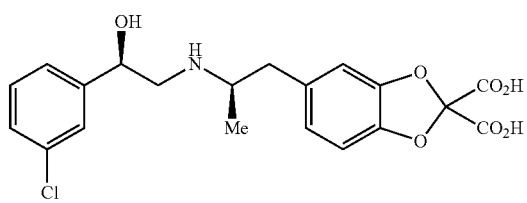 [SMILES: C[C@H](Cc1ccc2c(c1)OC(C(=O)O)(C(=O)O)O2)NC[C@H](O)c1cccc(Cl)c1]

Compound CL 316243 is a potent and selective beta-3 adrenergic receptor agonist (EC50=3 nM; selectivity 10000 orders of magnitude greater than β1 and β2) which can be commercially acquired in the form of disodium salt (151126-84-0):

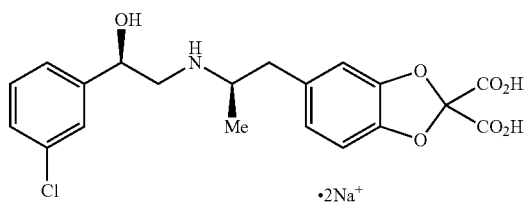 [SMILES: C[C@H](Cc1ccc2c(c1)OC(C(=O)O)(C(=O)O)O2)NC[C@H](O)c1cccc(Cl)c1]

In another preferred embodiment, the agonist used in the present invention is YM178 (Mirabegron) or a salt thereof. Mirabegron is a compound marketed for treating hyperactive bladder and has the following molecular formula:

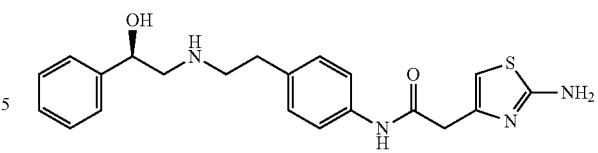

In another preferred embodiment, the agonist used in the present invention is GW427353 (Solabegron) or a salt thereof, such as its hydrochloride. Solabegron has the following molecular formula:

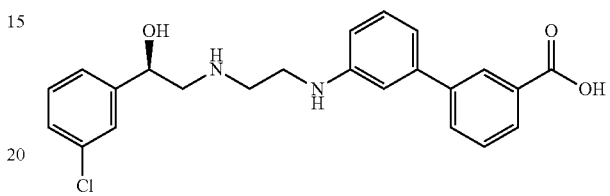

In another preferred embodiment, the agonist used in the present invention is SR 58611A (Amibegron) or a salt thereof. Amibegron is an antidepressant that has the following molecular formula:

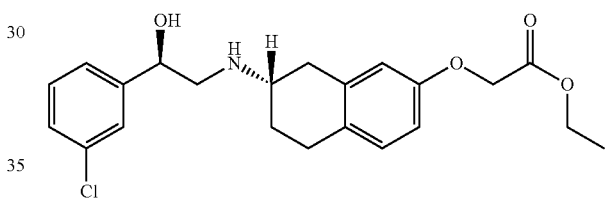

Other documents describing compound BRL 37344 and more compounds showing agonism towards beta-3 adrenergic receptor are: US20040242485A1, U.S. Pat. No. 4,873,240, U.S. Pat. No. 4,880,834, U.S. Pat. No. 5,002,946, U.S. Pat. No. 5,087,626, U.S. Pat. No. 5,236,951, U.S. Pat. No. 5,578,638, U.S. Pat. No. 6,172,099, U.S. Pat. No. 6,187,809. Additional compounds known to show selective agonist activity for beta-3 adrenergic receptors are described, for example, in patent documents: U.S. Pat. No. 4,396,627, U.S. Pat. No. 4,478,849, U.S. Pat. No. 4,999,377, U.S. Pat. No. 5,153,210, WO98/32753, WO97/46556, WO97/37646, WO97/15549, WO97/25311, WO96/16938, WO95/29159, WO02/06276, EP427480, EP659737, EP801060, EP714883, EP764632, EP764640, EP827746, U.S. Pat. No. 5,561,142, U.S. Pat. No. 5,705,515, U.S. Pat. No. 5,436,257, U.S. Pat. No. 5,578,620 and U.S. Pat. No. 6,537,994.

The person skilled in the art can easily determine if a compound is useful for the purpose of the invention. Therefore, as indicated above, there are conventional methods suitable for assessing if a compound is a good selective beta-3 adrenergic receptor agonist. Furthermore, both the determination of beta-3 agonist activity and of beta-3 receptor selectivity with respect to beta-1/beta-2 receptors can be evaluated following previously established specific functional assays such as those described in the aforementioned patents and applications, particularly WO98/32753, WO97/46556, EP764632, EP764640, and EP827746. As indicated above, selective beta-3 adrenergic receptor agonists are commercially available and/or can be prepared by known methods, such as those described, for example, in the aforementioned patents and applications.

In addition, the first aspect of the present invention also refers to a neuroprotective compounds capable of protecting BM sympathetic nerve fibres or the combination thereof, for its use in the treatment of myeloproliferative neoplasms.

Said neuroprotective compounds can be selected from the list consisting of 4-methylcatechol; NGF (neuron growth factors); glial cell line-derived neurotrophic factors (GDNF) pertaining to the Neurturin (NRTN), artemin (ARTN) or persephin (PSPN) families; Neurotrophin-3 and Neurotrophin 4/5; interleukin-6 (IL-6); Insulin-like growth factor 1 (IGF-1); vitamin E, in particular the α-tocopherol form of vitamin E; Acetylcysteine also known as N-acetylcysteine or N-acetyl-L-cysteine (abbreviated NAC); Acetyl-L-carnitine or ALCAR; amifostine and Leukemia inhibitory factor, or LIF.

Alternatively, the neuroprotective compounds are selected from compounds useful in the treatment of diabetic neuropathy. Such compounds can be selected from the group of gastrointestinal hormones known as incretins. Incretins are a group of gastrointestinal hormones that stimulate a decrease in blood glucose levels. Incretins do so by causing an increase in the amount of insulin released from the beta cells of the islets of Langerhans after eating, before blood glucose levels become elevated. They also slow the rate of absorption of nutrients into the blood stream by reducing gastric emptying and may directly reduce food intake. As expected, they also inhibit glucagon release from the alpha cells of the Islets of Langerhans. The two main candidate molecules that fulfill criteria for an incretin are glucagon-like peptide-1 (GLP-1) and gastric inhibitory peptide (also known as: glucose-dependent insulinotropic polypeptide or GIP). Both GLP-1 and GIP are rapidly inactivated by the enzyme dipeptidyl peptidase-4 (DPP-4). Therefore, other agents useful as neuroprotective compounds would be those capable of inactivating the enzyme dipeptidyl peptidase-4 (DPP-4).

Furthermore, in another preferred aspect of the invention, the neuroprotective compounds can also be selected from the list consisting of sitagliptin (Merck), saxagliptin/Onglyza (Bristol-Myers Squibb/AstraZeneca), linagliptin (Boehringer Ingelheim), dutogliptin (Phenomix Corporation), gemigliptin (LG Life Sciences, Korea), alogliptin (Takeda), vildagliptin/Galvus (Novartis) and dietary supplement obtained from the Berberine.

Any of the neuroprotective compounds to which reference is made herein seeks to represent such specific compound as well as certain variations or forms. Therefore the useful compounds in the present invention can be, for example, in neutral form, in the form of a base or acid, in the form of a salt, preferably a physiologically acceptable salt, in the form of a solvate or of a polymorph and/or in different isomeric forms.

The term "salt" must be understood as any form of an active compound used according to this invention in which said compound is in ionic form or is charged and coupled to a counterion (a cation or anion) or is in solution. This definition also includes quaternary ammonium salts and active molecule complexes with other molecules and ions, particularly complexes formed by means of ionic interactions. The definition particularly includes physiologically acceptable salts; this term must be understood as equivalent to "pharmacologically acceptable salts" or "pharmaceutically acceptable salts".

The expression "physiologically acceptable salt" or "pharmaceutically acceptable salt" is particularly understood in the context of this invention as a salt (as defined above) formed either with a acid that is physiologically tolerated, i.e., salts of the particular active compound with organic or inorganic acids that are physiologically tolerated, particularly if they are used in human beings and/or mammals, or with at least one cation, preferably an inorganic cation, that is physiologically tolerated, particularly if they are used in human beings and/or mammals. Examples of particular acid salts that are physiologically tolerated are: hydrochloric acid, hydrobromic acid, sulfuric acid, hydrobromide, monohydrobromide, monohydrochloride or hydrochloride, methiodide, methanesulfonic acid, formic acid, acetic acid, oxalic acid, succinic acid, malic acid, tartaric acid, mandelic acid, fumaric acid, lactic acid, citric acid, glutamic acid, hippuric acid, picric acid and/or aspartic acid salts. Examples of particular base salts that are physiologically tolerated are alkali metal and alkaline-earth metal salts and with NH4.

According to this invention, the term "solvate" must be understood to mean any form of the active compound according to the invention in which this compound binds to another molecule (usually a polar solvent) by means of a non-covalent bond, particularly including hydrates and alcoholates, such as methanolate, for example.

Also within the scope of the invention is any compound which is a prodrug of the neuroprotective compounds to which reference is made herein. The term "prodrug" is used in the broadest sense of the word and covers those derivatives converted into the compounds of the invention in vivo. Examples of prodrugs include, but are not limited to, derivatives and metabolites of the neuroprotective agents to which reference is made herein, including biohydrolyzable residues such as biohydrolyzable amides, biohydrolyzable esters, biohydrolyzable carbamates, biohydrolyzable carbonates, biohydrolyzable ureides and biohydrolyzable phosphate analogues. Prodrugs of compounds with functional carboxyl groups are preferably lower alkyl esters of carboxylic acid. Carboxylate esters are suitably formed by esterifying any of the carboxylic acid residues present in the molecule. Prodrugs can usually be prepared using well-known methods, such as those described in Burguer "Medicinal Chemistry and Drug Discovery 6th ed." (Donald J. Abraham ed. 2001, Wiley), "Design and Applications of Prodrugs" (H. Bundgaard ed., 1985, Harwood Academic Publishers) and Krogsgaard-Larsen et al. "Textbook of Drug Design and Discovery" Taylor & Francis (April 2002).

The neuroprotective compounds to which reference is made herein can include optical isomers depending on the presence of chiral centers or geometric isomers depending on the presence of multiple bonds (for example Z, E). Individual isomers, enantiomers or diastereoisomers and mixtures thereof, such as a racemic mixture are within the scope of the present invention.

Furthermore, any compound to which reference is made herein can exist as tautomers. Specifically, the term tautomer refers to one of two or more structural isomers of a compound in equilibrium and easily converted from one isomeric form to another. Common tautomeric pairs are amine-imine, amide-imidic acid, keto-enol, lactam-lactim, etc.

Unless otherwise indicated, it also is understood that the compounds of the invention include isotopically labeled forms, i.e., compounds differing only by the presence of one or more isotopically enriched atoms. For example, compounds having the present structures except the substitution of at least one hydrogen atom with a deuterium or tritium atom, or the substitution of at least one carbon with a 13C- or 14C-enriched carbon, or the substitution of at least one nitrogen with 15N enriched nitrogen, are within the scope of this invention.

The neuroprotective compounds to which reference is made herein are preferably in a pharmaceutically acceptable or substantially pure form. Pharmaceutically acceptable form is understood, among others, to have a pharmaceutically acceptable purity level excluding typical pharmaceutical additives such as diluents and vehicles, and to not include any material considered toxic at normal dosage levels. Purity levels with respect to the active ingredient are preferably greater than 50%, more preferably greater than 70%, most preferably greater than 90%. In a preferred embodiment, it is greater than 95% selective beta-3 agonist.

In a preferred embodiment of this aspect of the invention, the compound known as 4-methylcatechol is preferred, said compound has the following molecular formula:

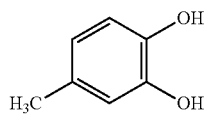

In another preferred embodiment of this aspect of the invention, the compound known as sitagliptin (INN; previously identified as MK-0431 and marketed as the phosphate salt under the trade name Januvia) is preferred, said compound has the following molecular formula:

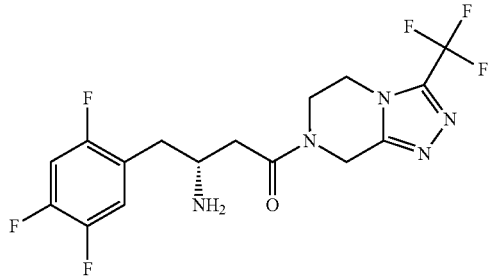 [SMILES: N[C@@H](CC(=O)N1CCn2c(nnc2C(F)(F)F)C1)Cc1cc(F)c(F)cc1F]

In another preferred embodiment of this aspect of the invention, the compound known as saxagliptin (rINN), previously identified as BMS-477118 is preferred, said compound has the following molecular formula:

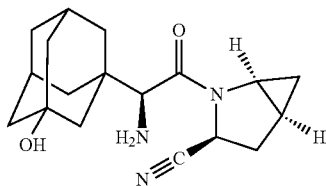 [SMILES: N#C[C@@H]1C[C@@H]2C[C@@H]2N1C(=O)[C@@H](N)C12CC3CC(CC(O)(C3)C1)C2]

In another preferred embodiment of this aspect of the invention, the compound known as linagliptin (BI-1356, trade names Tradjenta and Trajenta) is preferred, said compound has the following molecular formula:

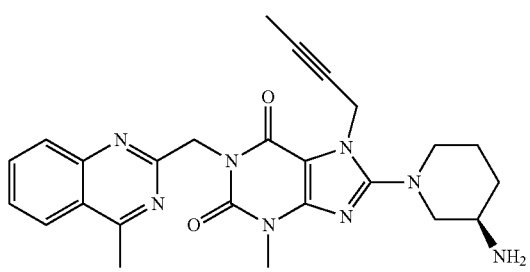 [SMILES: CC#CCn1c(N2CCC[C@@H](N)C2)nc2c1c(=O)n(Cc1nc(C)c3ccccc3n1)c(=O)n2C]

In another preferred embodiment of this aspect of the invention, the compound known as dutogliptin is preferred, said compound has the following molecular formula:

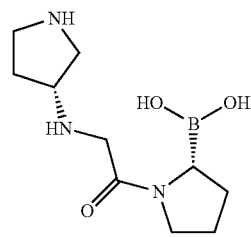 [SMILES: O=C(CN[C@@H]1CCNC1)N1CCC[C@H]1B(O)O]

In another preferred embodiment of this aspect of the invention, the compound known as gemigliptin (rINN), previously identified as LC15-0444, is preferred, said compound has the following molecular formula:

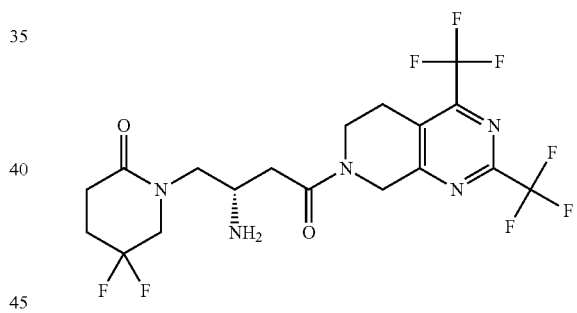

In yet another preferred embodiment of this aspect of the invention, the compound known as alogliptin (codenamed SYR-322, trade name Nesina) is preferred, said compound has the following molecular formula:

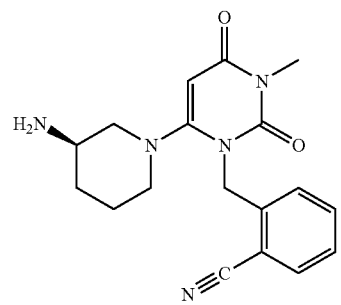 [SMILES: Cn1c(=O)cc(N2CCC[C@@H](N)C2)n(Cc2ccccc2C#N)c1=O]

In yet another preferred embodiment of this aspect of the invention, the compound known as vildagliptin (previously LAF237, trade names Galvus, Zomelis, Jalra) is preferred, said compound has the following molecular formula:

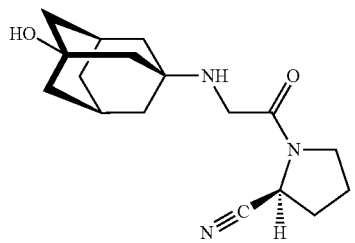

The inventors have thus demonstrated in different scenarios that the administration of selective beta-3 agonists or neuroprotective compounds paves the way to more efficient therapeutic strategies in MPN. For this purpose, the present invention shows that an efficient therapeutic strategy for the treatment of MPN lies on the administration of neuroprotective compounds, such as 4-methylcatechol, capable of protecting BM sympathetic nerve fibres and associated Schwann cells. Additionally, another efficient therapeutic strategy is shown herein as the administration of selective β3-adrenergic agonists such as BRL37344 or Mirabegron, since this strategy will compensate for deficient sympathetic stimulation of nestin+ MSCs and rescue BM Schwann cells.

The present invention therefore proposes the use of beta-3 adrenergic receptor agonists and neuroprotective compounds capable of protecting BM sympathetic nerve fibres as a broad spectrum therapeutic agent against MPN. Therefore, the results obtained prove the enormous usefulness of these compounds in treating and/or preventing MPN.

Medicinal products or pharmaceutical compositions for use in treating and/or preventing MPN comprising a selective beta-3 adrenergic receptor agonist and/or a neuroprotective compound and a pharmaceutically acceptable excipient are provided with this invention.

Examples of pharmaceutical compositions include any solid (tablets, pills, capsules, granules, etc.) or liquid (solutions, suspensions or emulsions) composition for oral, topical or parenteral administration.

The term "excipient" refers to components of a pharmacological compound other than the active ingredient (definition obtained from the European Medicines Agency—EMA). They preferably include a "carrier, adjuvant and/or vehicle". Carriers are forms in which substances are incorporated to improve drug administration and efficacy. Drug carriers are used in drug administration systems such as controlled release technology to prolong the actions of the drug in vivo, reduce drug metabolism and reduce drug toxicity. Carriers are also used in designs to increase the efficacy of drug administration to pharmacological target action sites (U.S. National Library of Medicine. National Institutes of Health).

Adjuvant is a substance added to a pharmacological product formulation affecting the action of the active ingredient in a predictable manner.

Vehicle is an excipient or a substance, preferably without any therapeutic action, used as a means to provide volume for the administration of medicinal products (Stedman's Medical Spellchecker, © 2006 Lippincott Williams & Wilkins).

Such pharmaceutical carriers, adjuvants or vehicles can be sterile liquids, such as water and oils, including petroleum oil or oil of an animal, plant or synthetic origin, such as peanut oil, soybean oil, mineral oil, sesame seed oil and the like, excipients, disintegrants, wetting agents or diluents. Suitable pharmaceutical carriers are described in "Remington's Pharmaceutical Sciences" by E. W. Martin. The selection of these excipients and the amounts to be used will depend on the form of application of the pharmaceutical composition.

The daily dosage for human beings and animals can vary depending on factors based on the respective species or other factors, such as age, sex, weight or degree of disease, etc.

The formulations can be prepared according to conventional methods such as those described in the Spanish, European or US Pharmacopoeias, or in similar reference texts, for example "Tratado de Farmacia Galénica", by C. Faulí i Trillo, $10^{th}$ Edition, 1993, Luzán 5, S.A. de Ediciones.

The compounds and compositions of this invention can be used with other drugs to provide a combination therapy. The other drugs can be part of the same composition or can be provided as a separate composition for administration at the same time or at a different time.

As it is used herein, the terms "to treat", "treating" and "treatment" generally include the eradication, elimination, reversal, alleviation, modification or control of MPN in a subject.

As it is used herein, the terms "prevention", "preventing", "preventive", "to prevent" and prophylaxis refer to the capability of a given substance to thwart, minimize or complicate the onset or development of MPN in a subject.

The term "subject" or "patient" in the context of the invention includes any animal, particularly vertebrate animals, preferably mammals, such as mice, rats, horses, pigs, rabbits, cats, sheep, dogs, cows, human beings, etc. In a preferred embodiment, the mammal is a human being.

Also provided in the present invention is a method of diagnosis or prognosis of the MPN in a patient of chronic myeloid leukaemia (CML), Polycythaemia vera, essential thrombocythaemia, myelofibrosis, chronic neutrophilic leukaemia, chronic eosinophilic leukaemia and mastocytosis. In this sense, prognosis of a MPN may be done through a method comprising the estimation of the sympathetic nervous system fibers in the BM of the patient through immunostaining of tyrosine hydroxylase in BM biopsies over time, wherein if sympathetic nervous system fibers are reduced in comparison to the sympathetic nervous system fibers in a normal subject and/or over time in the same patient, BM neural damage which preceeds nestin+ MSC reduction is progressing in the subject.

Typically, the patient with MPN will show a 3-fold reduction in the BM area occupied by tyrosine hydroxylase fibers.

In the context of the present invention, a reference or control value of the BM area occupied by sympathetic fibers is 0.15±0.09% of the total BM area in the section.

In the context of the present invention, the term "normal" makes reference to a healthy subject.

In another preferred embodiment, prediction or prognosis of a MPN in a subject may be done through a method comprising the following steps:

a. obtaining a biological sample from the bone marrow of a subject;
b. optionally performing erythrocyte lysis by standarised methods and obtaining the remaining bone marrow nucleated cells through centrifugation, where mRNA expression of the glial fibrillary acidic protein by qRT-PCR can be used as an indicator of the total number of glial cells in the sample of step a);

c. comparing the mRNA expression of the glial fibrillary acidic protein in the sample of step a) with a reference or control value of the mRNA expression of the glial fibrillary acidic protein in a normal subject or with the mRNA expression of the glial fibrillary acidic protein in a biological sample obtained from a normal subject, wherein if the mRNA expression of the glial fibrillary acidic protein in the sample of step a) is reduced in comparison to the reference or control value or to the mRNA expression of the glial fibrillary acidic protein in the biological sample obtained from a normal subject or over time, then BM neural damage which preceeds nestin+ MSC reduction is progressing in the subject.

In the context of the present invention, a reference or control value of the mRNA expression of the glial fibrillary acidic protein is 0.48±0.03 normalised to the mRNA expression of the housekeeping gene Glyceraldehyde-3-phosphate dehydrogenase (GAPDH).

In the context of this embodiment of the invention, the term "reduced" means a 160 fold reduction of the value of the mRNA expression of the glial fibrillary acidic protein normalised to the mRNA expression of the housekeeping gene GAPDH in controls.

In the context of the present invention, the term "control" makes reference to a healthy subject.

Figure 1:
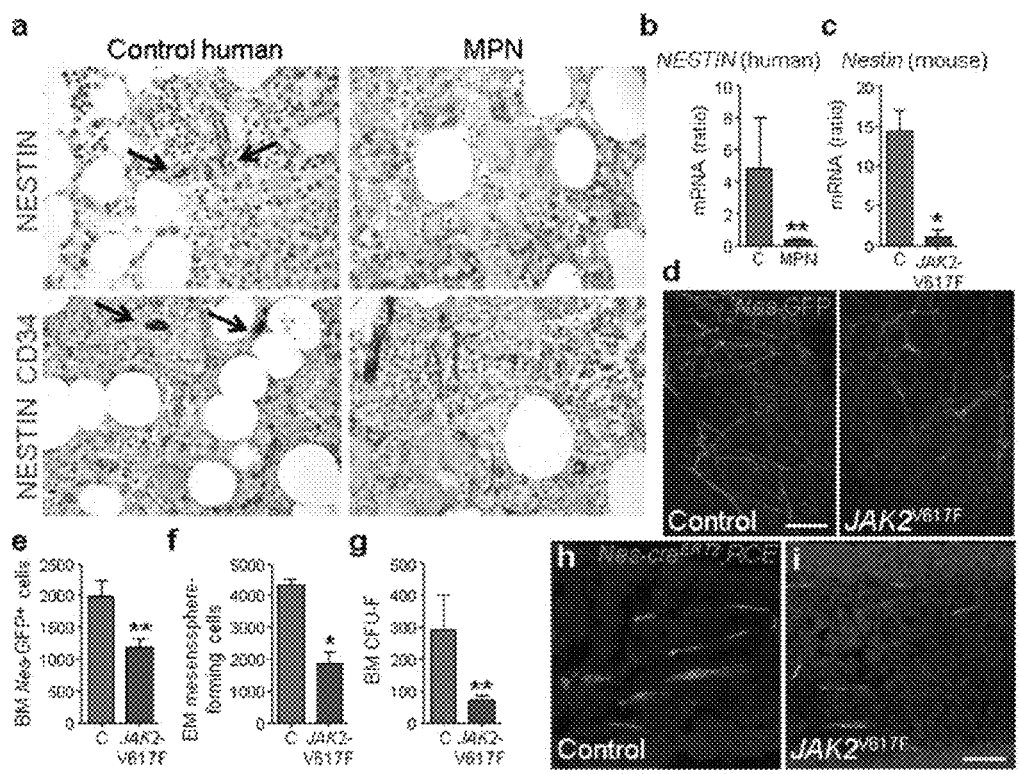
FIG. 1. Apoptosis of BM (Bone marrow) nestin+ HSC (haematopoietic stem cells) niche cells contributes to MPN (myeloprofilerative neoplasms) progression. a, BM sections of controls (left) and MPN patients (right) immunostained with NESTIN (brown, arrows; all panels) and CD34 (red, lower panels; magnification, 200×). Numbers of NESTIN+ niches per mm2 (mean±SD) were 1.15±0.3 (control) and 0.17±0.18 (MPN; n=40; p=10-6, Mann-Whitney U test). b-c, NESTIN Mrna expression in BM cells controls, MPN patients and mice (n=2-11). d, Nes-GFP+ cells in skull BM of control (left) and MPN mice (right; n=10). e-g, CD45−CD31−Ter119-11 Nes-GFP+cells (e), mesensphere-forming cells (f) and fibroblastic colony-forming units (CFU-F, g) in BM cells from WT mice 30 weeks after transplantation with control or MPN BM cells (n=6-12). h-i, Lineage-tracing studies of nestin+cells. Femoral sections of tamoxifen-treated Nes-creERT2; RCE:loxP mice 28 weeks after transplantation with (h) control or (i) MPN BM cells, showing fluorescent signals from GFP and nuclei counterstained with DAPI (n=4). j, Fraction of live, early and late apoptotic BM stromal Nes-GFP+cells from control or MPN mice (n=5-7). k-m, Blood counts (k), femoral trichromic (l) and spleen hematoxylin-eosin stainings (m) of Nes-creERT2;iDTA and control mice 20 weeks after transplantation of MPN BM cells (n=3). n, Frequency of lin-sca-1+c-kit+(LSK) haematopoietic progenitors in BM nucleated cells (BMNC) of Nes-creERT2;Cxcl12fl/fl and control littermates 30 weeks after transplantation with MPN BM cells and 24 weeks after tamoxifen treatment (n=5-7). c-e, j, 6-8 weeks after plpC treatment. Scale bar (d, h) 200 μm. Magnification (l, m) 100×. Data are mean±SEM. * p<0.05; ** p<0.01 (unpaired two-tailed t test). BM, bone marrow. C, control (disease-free) mice.
Figure 1:
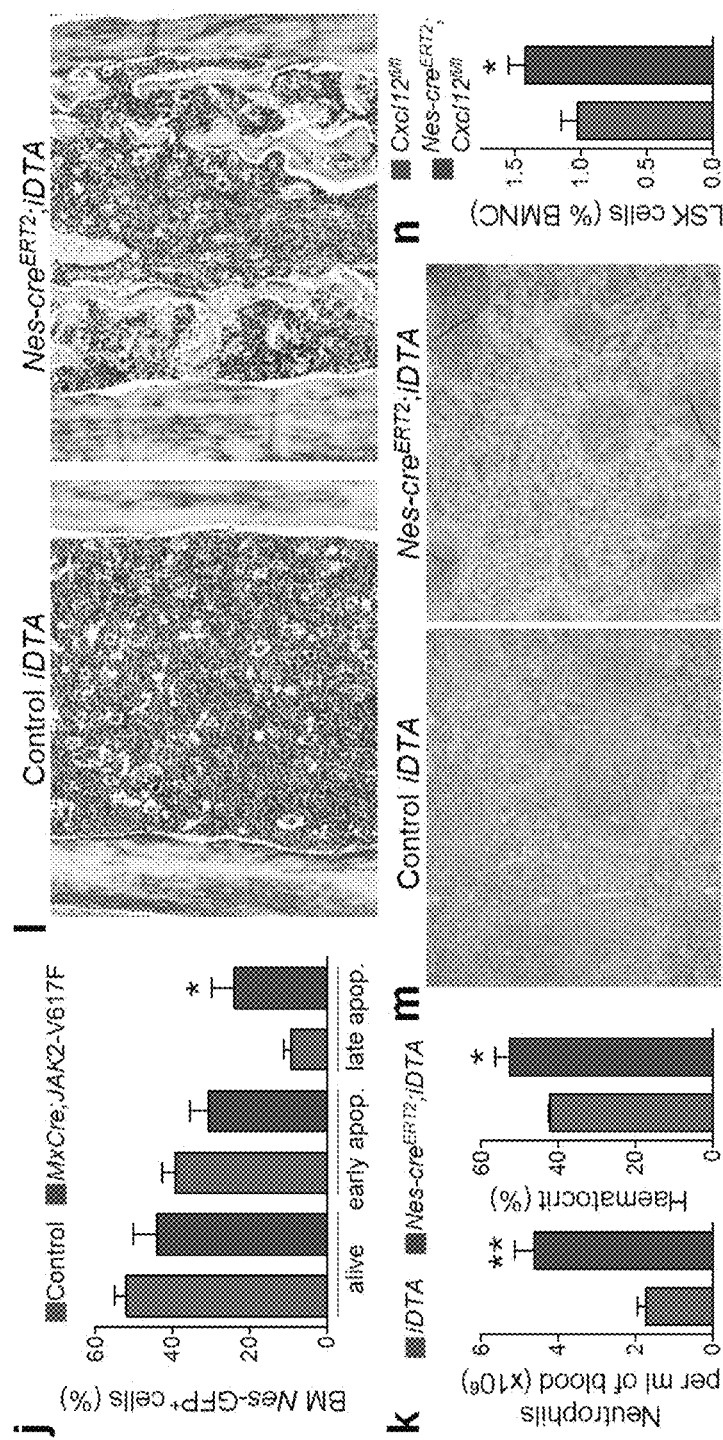

In addition, as shown in FIG. 1 the apoptosis of BM nestin+ mesenchymal stem cell niche cells contributes to MPN progression. Thus, in a preferred embodiment, prediction or prognosis of a MPN in a subject may be done through a method comprising the following steps:

a. Obtaining a biological sample from the bone marrow of a subject over time;

b. using as an indicator the total number of BM nestin+ MSCs in the sample of step a) as measured by immunostaining of nestin followed by scoring taking into account the number of NESTIN+ perivascular niches (either single cells or clusters of up to 3 cells) in the BM samples. On average 7.2 mm$^2$ of BM should be evaluated and results extrapolated to 1 mm$^2$;

c. comparing the total number of BM nestin+ MSCs in the biological sample of step a) with a reference or control value of the total number of BM nestin+ MSC in a normal subject or with the total number of BM nestin+ MSCs in a biological sample obtained from a normal subject, wherein if the number of cells is reduced in comparison to the reference or control value or to the number of BM nestin+ MSCs in the biological sample obtained from a normal subject or over time, then damage of the niche that preceeds myelofibrosis is present in the patient.

In the context of the present invention, a reference or control value of the total number of BM nestin+ cells in a normal subject is 1.15±0.3 niches per mm$^2$ (each one containing at least one positive cell).

In the context of this embodiment of the invention, the term "reduced" is a 6-fold reduction of the number BM nestin+ MSC in a normal subject.

In the context of the present invention, the term "normal" makes reference to a healthy subject.

In another preferred embodiment, prediction or prognosis of a MPN in a subject may be done through a method comprising the following steps:

a. obtaining a biological sample from the bone marrow of a subject;

b. performing erythrocyte lysis by standarised methods and obtaining the remaining bone marrow nucleated cells through centrifugation, where mRNA expression of NESTIN by qRT-PCR can be used as an indicator of the total number of nestin+ MSC in the sample of step a);

d. comparing the mRNA expression of NESTIN in the sample of step a) with a reference or control value of the mRNA expression of NESTIN in a normal subject or with the mRNA expression of NESTIN in a biological sample obtained from a normal subject, wherein if the mRNA expression of NESTIN in the sample of step a) is reduced in comparison to the reference or control value or to the mRNA expression of NESTIN in the biological sample obtained from a normal subject or over time, then damage of the niche that preceeds myelofibrosis is present in the patient.

In the context of the present invention, a reference or control value of the mRNA expression of NESTIN is 4.86±4.55 normalised to the mRNA expression of the housekeeping gene Glyceraldehyde-3-phosphate dehydrogenase (GAPDH).

In the context of this embodiment of the invention, the term "reduced" means a 13 fold reduction of the value of the mRNA expression of NESTIN normalised to the mRNA expression of the housekeeping gene GAPDH in controls.

In the context of the present invention, the term "control" makes reference to a healthy subject.

A further aspect of the invention refers to a kit suitable for implementing any of the precedent methods.

The invention is described below by means of the following examples which must be considered as merely illustration and non-limiting thereof.

EXAMPLES

Example 1. Materials and Methods for FIGS. 1-13

1.1. Human Study

The study was approved by institutional review boards. Written informed consent was obtained from all patients in accordance with the Declaration of Helsinki. The diagnosis of MPN was established according to the revised criteria of the World Health Organization.

1.2. In Vivo Pharmacological Treatments

In Mx1-cre; JAK2-V617F double-transgenic mice, expression of the human JAK2-V617F mutation is driven by the endogenous Jak2 promoter and can be conditionally expressed in haematopoietic cells upon Myxovirus resistance-1 (Mx1)-driven Cre recombinase activation by polyinosine-polycytosine (plpC). PlpC-induced transgenic mice and wild-type mice transplanted with BM cells from these mice develop progressive symptoms of PV19,20.

Age-matched, female wild-type C57BL/6J or Nes-gfp mice were used as recipients in bone marrow (BM) transplantation assays and for in vivo pharmacological treatments. Lethally irradiated (12 Gy) recipient mice were transplanted with 2×106 BM cells from Mx-Cre; JAK2V617F mice induced with plpC 8 weeks before, or from Cre-negative mice as disease-free controls. The selective β3-adrenergic agonist BRL37344 (Sigma, St. Louis, Mo.) was administered at 2 mg kg-1 through intraperitoneal (i.p.) injection twice per day (every 10-12 hours). Vehicle (saline solution) daily injections were performed in the same way. Unless indicated, treatment was initiated 4 weeks posttransplant, when animals evidenced peripheral blood signs of MPN. Mice were randomly distributed prior to treatment initiation, and disease development was monitored over time in peripheral blood samples, using an automated blood counter. A similar treatment protocol was performed with the selective beta3-adrenergic agonist Mirabegron (2 mg kg-1, i.p., two injections per day separated 10-12 hours). The neuroprotective drug 4-methylcatechol (10 μg kg-1, i.p.) was injected once daily. The JAK inhibitor INCB018424 (S-Ruxilitinib, Abmole Bioscience) was administered by oral gavage (30 mg kg-1, twice per day separated 10-12 hours) in 0.5% hydroxypropylmethylcellulose (Sigma) after solubilisation in DMSO. The IL-1 receptor antagonist (Kineret, Sobi, Stockholm, Sweden) was administered by subcutaneous osmotic pumps (Alzet) infusing a continuous dosing of 40 mg kg-1 per day. Mice were sacrificed at different time points and subjected to complete necropsy; BM and spleen were analysed by histology and flow cytometry; femora and skull were used for immunostainings, and haematopoietic and stromal cells were additionally used for functional assays ex vivo.

For quantification of HSC, BM cells from treated mice were used for competitive repopulation assays using limiting cell dilutions. Briefly, CD45.1+ competitor BM cells ($2\times10^6$) were transplanted into lethally irradiated CD45.2+ recipient mice, after mix with $4\times10^5$, $4\times10^4$ and $4\times10^3$ donor BM cells. Peripheral blood chimerism was assessed by flow cytometry every 2-4 weeks. Mice were sacrificed 16 weeks after the transplant and the BM LSK cell chimerism was assessed by flow cytometry. A minimum of 5% CD45.2+ chimerism in the LSK cell compartment was considered as positive in recipients of control BM cells. In recipients of mutant BM, mice were considered as positive ("leukaemic") above 50% CD45.2+ chimerism. The software LCalc (StemCell Technologies) was used for quantification of HSCs and MPN-initiating cells in control and mutant donor BM, respectively.

Nes-creERT2 mice were induced with tamoxifen (Sigma) for the indicated time periods. Control and experimental mice were i.p. injected with 140 mg kg-1 of tamoxifen (14 mg ml-1 solution in corn oil), 3 times on alternate days, and were simultaneously fed with phytoestrogen-free diet for one week, followed by tamoxifen-containing diet TM400 (Harlan). Nes-creERT2;RCE:loxP mice were used for in vivo lineage-tracing studies. To selectively deplete nestin+ cells, Nes-creERT2 mice were crossed with a Cre recombinase inducible diphtheria toxin mouse line (iDTA). Nes-creERT2 mice were additionally crossed with conditional Cxcl12-deficient mice to selectively delete Cxcl12 in nestin+ cells upon tamoxifen induction.

BM cell extraction, flow cytometry and fluorescence-activated cell sorting For haematopoietic cell recovery, bones were crushed in a mortar, filtered through a 40-μm mesh to obtain single cell suspensions, and depleted of red blood cells by lysis in 0.15 M NH4Cl for 10 min at 4° C. Spleen samples were homogenised and filtered prior to lysis; blood samples were directly lysed. Cells (1-$2\times10^6$ cells per sample) were incubated with the appropriate dilution (2-5 μg ml-1) of fluorescent antibody conjugates and 4',6-diamidino-2-phenylindole (DAPI) for dead cell exclusion, and analysed on LSRFortessa flow cytometer (BD Biosciences, Franklin Lakes, N.J.) equipped with FACSDiva Software (BD Biosciences). The following antibodies were used: fluorescent CD45.1 (A20), CD45.2 (104), B220 (RA3-6B2), CD11b (M1/70), CD3ε (145-2C11), Ly-6G (1A8), Sca1 (E13-161.7), CD34 (RAM34), CD135/Flt3 (A2F10.1), and biotinylated lineage antibodies (CD11b, Gr-1, Ter119, B220, CD3ε), all from BD Biosciences; c-kit (2B8) from eBioscience (San Diego, Calif.). Biotinylated antibodies were detected with fluorochrome-conjugated streptavidin (BD Biosciences). Phenotypic populations of HSC were defined as long-term haematopoietic stem cells (HSCs) (lin– Sca1+ c-kit+ (LSK) CD34– Flt3–), short-term HSCs (LSK CD34+ Flt3–) and multipotent progenitors (MPP) (LSK CD34+ Flt3+).

For isolation of nestin+ cells, bones were cleaned from surrounding tissue, crushed in a mortar with a pestle, and collagenase-digested (catalog number 07902, StemCell Technologies) in a shaking water bath at 37° C. for 45 min. Cells were filtered through a 40-μm mesh and erythrocytes were lysed as previously described. The resulting bone marrow-enriched cell suspensions were pelleted, washed and resuspended in PBS buffer containing 2% foetal calf serum (FCS) for further analyses. For cell sorting, cells were enriched by immunomagnetic depletion using biotinylated CD45 (104), CD31 (MEC13.3), and Ter119 antibodies followed by addition of streptavidin magnetic beads (BD Biosciences), according to the manufacturer's recommendations. BM stromal CD45– CD31– Ter119– cells were further purified according to GFP fluorescence using a FACS Aria cell sorter (BD Bioscience). For the determination of apoptotic cells, samples were washed with PBS after surface antibody staining and subsequently stained with Annexin V-Pacific Blue and SYTOX AADvanced (Invitrogen, Life Technologies, Paisley, UK). For functional assays, cells were enriched by immunomagnetic depletion using biotinylated CD45 and Ter119. For immunophenotypic characterisation, total BM samples were studied by flow cytometry using the following additional antibodies: CD63 (NVG-2), CD105 (MJ7/18), CD140a (APA5), Vcam, CD51 (RMV-7), all from Biolegend; and CD90.2 from BD Biosciences.

1.3. Cell Culture

Colony-forming units in culture (CFU-C) assay was performed. BRL37344 and 4-methylcatechol were added to the methylcellulose at the specified concentrations. Colonies of more than 50 cells were scored after 7 days of incubation at 37° C., 5% CO2, 20% O2 in a water-jacketed incubator. For CFU-F assays, BM CD45– Ter119– cells were plated into 6-well dishes and cultured in maintenance medium (α-MEM, 15% FCS with antibiotics). After 10-12 days in culture, adherent cells were fixed with 100% methanol and stained with Giemsa stain (Sigma) to reveal fibroblastic clusters. Colonies with more than 50 cells were scored as CFU-F.

For mesensphere formation, cells were plated in ultra-low adherent 35-mm dishes (StemCell Technologies). The growth medium contained 15% chicken embryo extract, prepared as described 32,33,33; 0.1 mM β-mercaptoethanol; 1% non-essential aminoacids (Sigma); 1% N2 and 2% B27 supplements (Invitrogen); recombinant human fibroblast growth factor (FGF)-basic, recombinant human epidermal growth factor (EGF), recombinant human platelet-derived growth factor (PDGF-AB), recombinant human oncostatin M (227 a.a. OSM) (20 ng ml-1) and recombinant human insulin-like growth factor-1 (IGF-1; 40 ng ml-1) (Peprotech) in DMEM/F12 (1:1)/human endothelial (1:2) serum-free medium (Invitrogen). The cultures were kept at 37° C. with 5% CO2, 20% O2 in a water-jacketed incubator. One-half medium changes were performed weekly. Mesenspheres were scored at day 10.

For co-culture of BM-derived Schwann cells and MSCs with BM LSK cells from control and mutant mice, neonatal BM CD45– CD31– Ter119– Nes-GFP+ Pdgfrα–/+ cells containing Schwann cell precursors and MSCs, respectively (Isern J et al., submitted), were sorted and cultured under Schwann cell differentiation conditions, as previously described 34, or mesenchymal culture conditions, in MEMα supplemented with 10 ng ml-1 PDGFAB, 15% FBS. Both were co-cultured for 24 h with primary BM LSK cells isolated by FACS from control or mutant mice. Schwann cells derived from sorted GFP+ Pdgfrα– BM precursors were additionally incubated with IL1ra (200 ng ml-1) for the co-culture period. After 24 h of co-culture, haematopoietic cells were washed away and the remaining adherent Schwann cells were fixed and analysed for apoptosis by TUNEL.

Histological analyses, immunohistochemistry and immunofluorescence Hematoxylin & eosin conventional staining was performed in deparaffinised sections followed by re-hydration. Harris hematoxylin solution was used for staining and eosin Y solution was utilized for counterstaining. After briefly rinsing the slides in distilled water, dehydration was quickly performed in 70%, 95%, absolute ethyl alcohol. Sections were cleared with xylene and mounted in DPX.

For Masson's trichrome staining of collagen, sections were fixed again in Bouin's solution for 1 hour at 56° C. and stained with Weigert's iron hematoxylin working solution for 10 minutes, followed by Biebrich scarlet-acid fuchsin solution for 10-15 minutes. Phosphomolybdic-phosphotungstic acid solution was added for 10-15 minutes or until collagen lost the red staining. Sections were transferred directly to fast green solution and stained for 1 minute, briefly rinsed and incubated with 1% acetic acid solution for 2-5 minutes. After a brief rinse in distilled water, dehydration was quickly performed in 70%, 95% and absolute ethyl alcohol; sections were cleared with xylene and mounted with DPX.

Gordon & Sweet's staining protocol was used to visualise reticulin fibres. Briefly, deparaffinised sections were oxidised in 1% acidified potassium permanganate for 5 minutes, followed by 1% Oxalic acid to decolourise, and mordant in 2.5% iron alum for 15 minutes. Sections were impregnated in ammoniacal silver solution for 2 minutes and reduced with 10% aqueous formalin for 2 minutes. Afterwards the sections were incubated in gold chloride for 2 minutes and fixed with 5% aqueous sodium thiosulphate. A 15 second incubation in Fast green was used for counter-staining. After a brief rinse in distilled water, dehydration was quickly performed in 70%, 95% and absolute ethyl alcohol; sections were cleared with xylene and mounted with DPX.

For Van Gieson's staining of collagen, nuclei were stained with celestine blue for 2 minutes, briefly rinsed in distilled water, incubated with Harris hematoxylin solution for 2 minutes and washed under running tap water for 5 minutes. Curtis stain (saturated aqueous picric acid, 1% ponceau S and glacial acetic acid mix) was performed for 5 minutes, until collagen was pink. After a brief rinse in distilled water, dehydration was quickly performed in 70%, 95% and absolute ethyl alcohol; sections were cleared with xylene and mounted with DPX.

Immunofluorescence staining of cryostat sections was performed. For whole mount staining of the calvaria, all incubation times were extended. The antibodies used were TH (Rabbit pAb, Millipore) and GFAP (Rabbit pAb, Dako). Confocal images were acquired with a laser scanning confocal (Zeiss LSM 700). At least 3 different sections were used for quantification using ImageJ software.

For NESTIN/CD34 immunohistochemistry of human BM samples, 12 control BM biopsies (2 from healthy donors, 2 from patients with reactive peripheral leukocytosis, and 8 performed for lymphoma staging, but unaffected by lymphoma) and 28 MPN (13 of them were JAK2-V617F+) were stained for NESTIN applying the monoclonal antibody 10C2 from AbD Serotec (OBT1610) at a dilution of 1:50 using an automated immunostainer (Benchmark, Ventana/Roche). Antigen retrieval was achieved by cell conditioning (CC1 from Ventana/Roche) treatment for 60 minutes. Incubation for 60 minutes, signal amplification and visualization (amplifier and chromogen ultraview universal diaminobenzidine from Ventana/Roche) followed. For NESTIN/CD34 double stainings, the ready to use monoclonal antibody QBEnd/10 from Ventana/Roche (790-2927) was applied after NESTIN visualization and envisioned using an alternative chromogenic detection kit (basic aminoethylcarbazole from Ventana/Roche). Scoring was performed taking into account the number of NESTIN+ perivascular niches (either single cells or clusters of up to 3 cells) in the BM samples. On average 7.2 mm2/case were evaluated and results were the extrapolated to 1 mm2. For TH immunofluorescence of human BM samples, 2 control and 16 MPN (5 essential thrombocythemia, 4 chronic myeloid leukemia, and 7 primary myelofibrosis) BM biopsies were used. Sections were desparaffined and antigen retrieval was performed with EDTA pH 9. After 30 minutes of permeabilisation in methanol, immunofluorescence staining and quantification was performed as described above.

1.4. ELISA

Bio-Plex Pro Mouse Th17 cytokine Panel A 6-plex (M60-00007NY, Bio-Rad) was performed following the manufacturer's protocol. Cxcl12 protein levels were measured by conventional ELISA. Briefly, 96-well plates were coated over night at 4° C. with 2 μg ml-1 of monoclonal anti-human and mouse CXCL12/SDF-1 antibody (MAB350, R&D Systems). After blocking, bone marrow extracellular fluids were incubated for 2 h at room temperature, followed by addition of biotinylated anti-human and mouse CXCL12/SDF-1 antibody (BAF310, RD). Streptavidin-horseradish peroxidase conjugate (RPN1231V, Dako) was used for reporting signal, and reaction was stopped with horseradish peroxidase substrate (TMB, ES001-500ML, Chemicon, Millipore).

Stardard curve was performed with recombinant human, feline, rhesus macaque SDF-1 alpha (350-NS, R&D). RNA isolation and qPCR RNA isolation was performed using the Dynabeads® mRNA DIRECT™ Micro Kit (Invitrogen). Reverse transcription was performed using the Reverse Transcription System (Promega), following the manufacturer's recommendations. The expression level of each gene was determined by using the relative standard curve method. Briefly, a standard curve was performed by doing serial dilutions of a mouse or human reference total RNA (Clontech). The expression level of each gene was calculated by interpolation from the standard curve. All values were normalised with Gapdh as endogenous control. The primers shown in the table were used.

TABLE

| | RNAseq and microarray | | |
|---|---|---|---|
| Gene Name | Species | Forward sequence (5'-3') | Reverse sequence (5'-3') |
| GFAP | Human | CCGACAGCAGGTCCATGTG | GTTGCTGGACGCCATTGC |
| NEST N | Human | CAACAGCGACGGAGGTCTC | GCCTCTACGCTCTCTTCTTTGA |
| GAPDH | Human/Mouse | GCATGGCCTTCCGTGTTC | CCTGTTCACCACCTTCTTGAT |

TABLE-continued

RNAseq and microarray

| Gene Name | Species | Forward sequence (5'-3') | Reverse sequence (5'-3') |
|---|---|---|---|
| Adrb2 | Mouse | AGCAATAGCAACGGCAGAAC | TTCACAAAGCCTTCCATGCC |
| Adrb3 | Mouse | AAACTGGTTGCGAACTGTGG | TAACGCAAAGGGTTGGTGAC |
| Angpt1 | Mouse | CTCGTCAGACATTCATCATCCAG | CACCTTCTTTAGTGCAAAGGCT |
| Casp1 | Mouse | TTGGAGCTCAAGTTGACCTCAG | TGTCAGAAGTCTTGTGCTCTGG |
| Cxcl12 | Mouse | TGCATCAGTGACGGTAAACCA | TTCTTCAGCCGTGCAACAATC |
| Gfap | Mouse | CGGAGACGCATCACCTCTG | AGGGAGTGGAGGAGTCATTCG |
| Il1b | Mouse | GAAATGCCACCTTTTGACAGTG | TGGATGCTCTCATCAGGACAG |
| Il1r | Mouse | GTGCTACTGGGGCTCATTTGT | GGAGTAAGAGGACACTTGCGAAT |
| Il1rn | Mouse | GAGAAACAACCAGCTCATTGC | GGATGCCCAAGAACACACTATG |
| Kitl | Mouse | CCCTGAAGACTCGGGCCTA | CAATTACAAGCGAAATGAGAGCC |
| Lifr | Mouse | TACGTCGGCAGACTCGATATT | TGGGCGTATCTCTCTCTCCTT |
| Mbp | Mouse | AATCGGCTCACAAGGGATTCA | TCCTCCCAGCTTAAAGATTTTGG |
| Mobp | Mouse | CCAGGCTCTCCAAGAACCAG | GGTCCACGATCTCACGCTT |
| Nestin | Mouse | CCCTGAAGTCGAGGAGCTG | CTGCTGCACCTCTAAGCGA |
| Pkp4 | Mouse | GAACCTGTCATACCGGCTGG | TTCCGAGTCTTTGCTGGGAGA |
| Plekhb1 | Mouse | CTGGAAGCGGAATTGGTTCG | TGCCGTCTCGTCATGGTAGTA |
| Plp1 | Mouse | TGAGCGCAACGGTAACAGG | TTCCCAAACAATGACACACCC |
| S100b | Mouse | TGGTTGCCCTCATTGATGTCT | CCCATCCCCATCTTCGTCC |
| Slit2 | Mouse | CCATGTAAAAATGATGGCACCTG | ATCACAGTCCTGACCCTTGAA |

For next-generation sequencing, total RNA was isolated using the Arcturus Picopure RNA isolation kit (Life Technologies) from small numbers of FACS sorted CD45− CD31− Ter119− GFP+ cells, obtained from the BM of Nes-gfp;Mx1-cre;JAK2-V617F mice and control littermates 6 weeks after plpC treatment. Each sample was a pool from 3 different animals. RNA was amplified and prepared for RNA-Seq using the Ovation RNA-Seq System v2 (NuGEN) following the manufacturer's recommendations. The RNA sequencing library was prepared with the TruSeq RNA Sample Preparation v2 Kit (Illumina, San Diego, Calif.) to construct index-tagged cDNA. The quality, quantity and the size distribution of the Illumina libraries were determined using the DNA-1000 Kit (Agilent Bioanalyzer). Libraries were sequenced on the Genome Analyzer IIx (Illumina) following the standard RNA sequencing protocol with the TruSeq SBS Kit v5. Fastq files containing reads for each library were extracted and demultiplexed using Casava v1.8.2 pipeline. Sequencing adaptor contaminations were removed from reads using cutadapt software tool (MIT) and the resulting reads were mapped and quantified on the transcriptome (NCBIM37 Ensembl gene-build 65) using RSEM v1.1734.

Expression data was compared between both samples by the analysis of individual selected genes for differential expression, and through gene-set enrichment analyses (GSEA) to detect coordinated changes in sets of genes representing pathways, functional signatures or transcription factor targets. GSEA were performed as described (http://www.broadinstitute.org/gsea/index.jsp), using a weighted statistic, fold-change ranking, 1000 gene-set permutations and several gene set databases found in the 1.5. Molecular Signatures Database For microarray analyses, total RNA was isolated as previously described from BM CD45− CD31− Ter119− Nes-GFP+ cells obtained from Nes-gfp mice 10 weeks after transplantation with Mx1-cre;JAK2-V617F (n=3) or control cells (n=1). RNA was amplified using the NuGen Ovation system and hybridized to the Affymetrix MoGene 1.0 ST array. Data normalisation was performed using the Robust Multi-array Average (RMA) algorithm. To perform principal component analysis (PCA) comparison with previously published data, GEO data sets were downloaded and pre-processed using the GEOquery Bioconductor package35. Normalised data sets were adjusted to the same intensity range, and batch effect correction was performed using ComBat36.

1.6. Statistical Analyses

Statistical analyses and graphics were carried out with GraphPad Prism 5 software and Microsoft Excel. Unless specified, data sets were compared by unpaired two-tailed tests; p values less than 0.05 were considered statistically significant.

Figure 14:
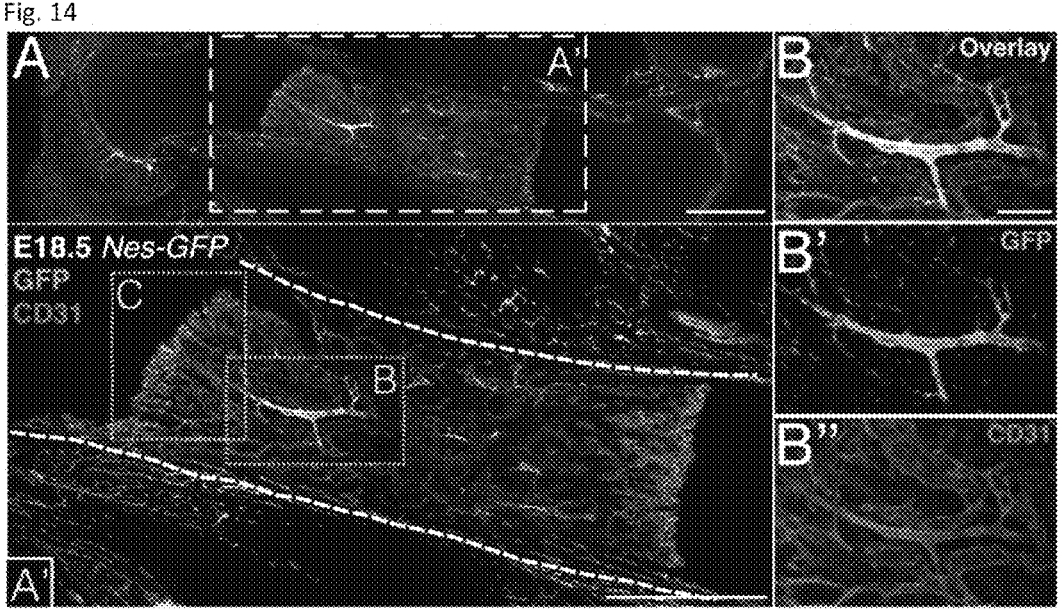
FIG. 14. Fetal BM nestin$^+$ cells proliferate slowly and are distinct from osteochondral cells. a-c, Nes-GFP$^+$ cells in fetal bones undergoing endochondral ossification. Whole-mount confocal projection of E18.5 Nes-Gfp femoral BM stained with CD31 (magenta) to mark endothelium. Note perivascular distribution of GFP$^+$ cells in arterioles (b) and small vessels invading the primary spongiosa (c). d-e, Nes-Gfp transgene is expressed by a subset of BM endothelial cells. FACS histograms show the frequency of CD45-Nes-GFP$^+$ cells expressing CD31. f, Endogenous Nestin mRNA expression measured by qPCR in stromal populations isolated from Nes-Gfp mice at indicated stages (mean±SD, n=3-5). g, Nes-Gfp BM section stained with smooth muscle actin antibodies (αSMA, asterisks) to reveal arterioles. h, Limb section of E17.5 Nes-Gfp;Col2.3-Cre;Kfp embryo showing Nes-GFP$^+$ and osteoblastic cells identified with antibodies against Katushka protein, driven by the 2.3-kb proximal fragment of the α1(I)-collagen promoter. Arrowheads, endosteal surface. i, Diaphysis of E17.5 Nes-Gfp embryo showing S100$^+$ chondrocytes. j, magnified detail. k, Representative cell cycle profiles of BM stromal Nes-GFP$^{+/-}$ cells at early postnatal stages. Frequencies of cells in G$_2$/S-M (%) are indicated. l, Number of stromal Nes-GFP$^{+/-}$ cells in postnatal BM (mean±SEM, n=3-4). Scale bars: 500 μm (A-A'), 200 μm (g-h), 100 μm (b-c, i-j). (g-h, j) Dashed line indicates bone contour. BM, bone marrow; C, cartilage; PS, primary spongiosa.
Figure 14:
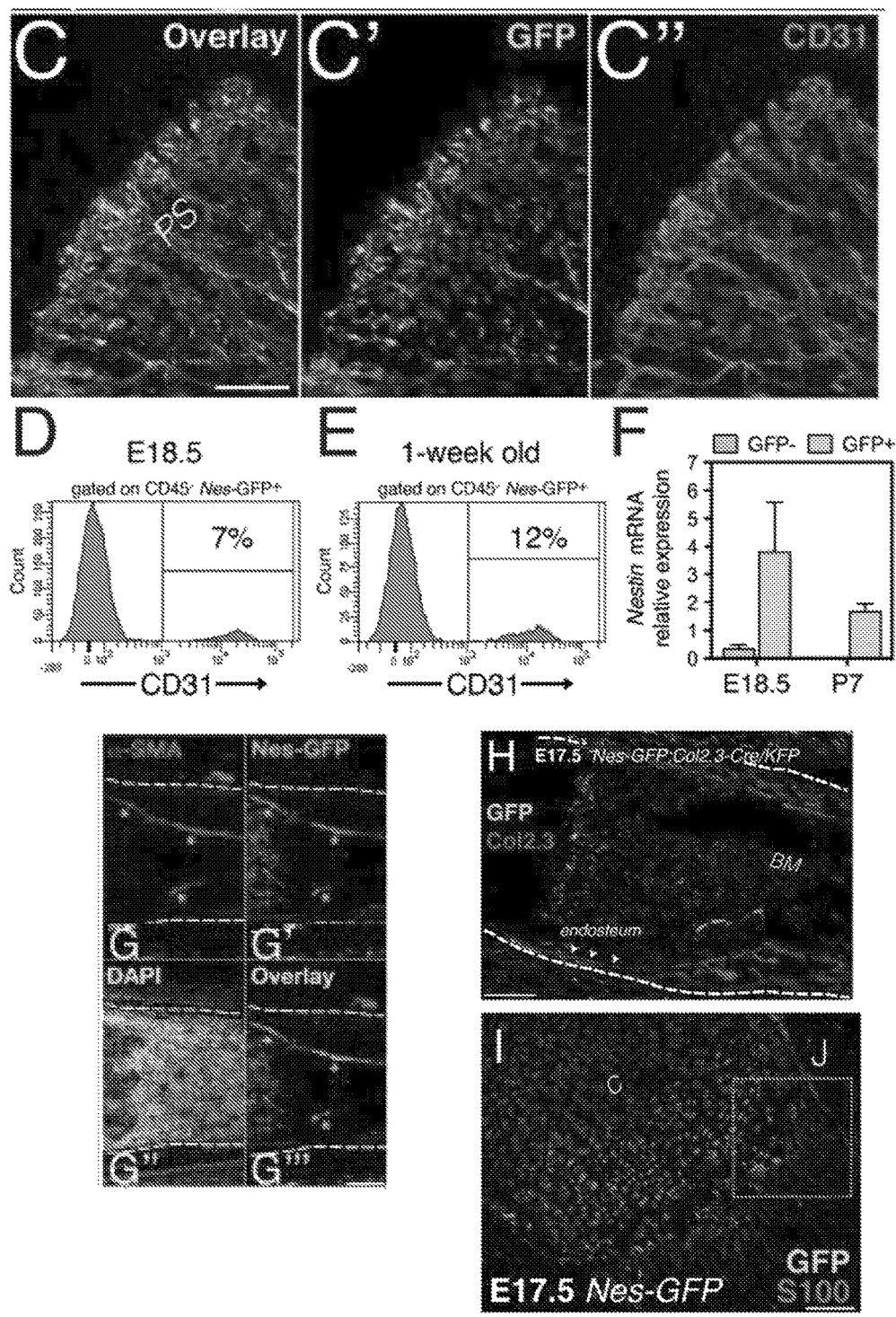
Figure 14:
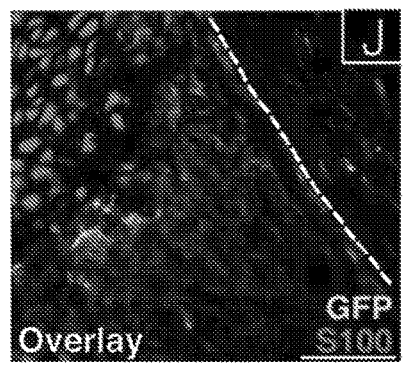
Figure 14:
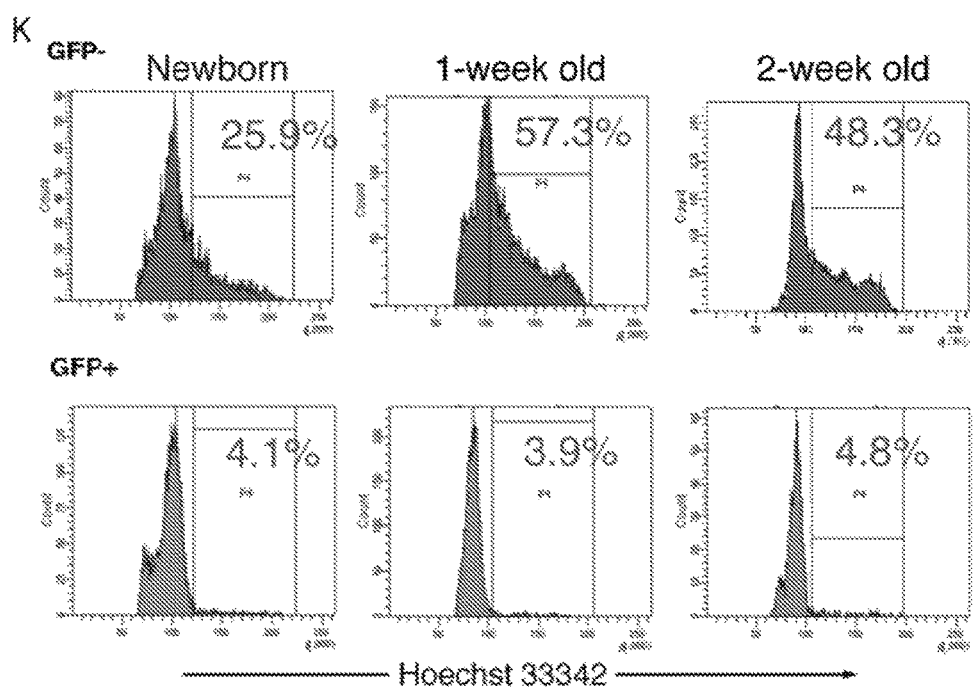
Figure 14:
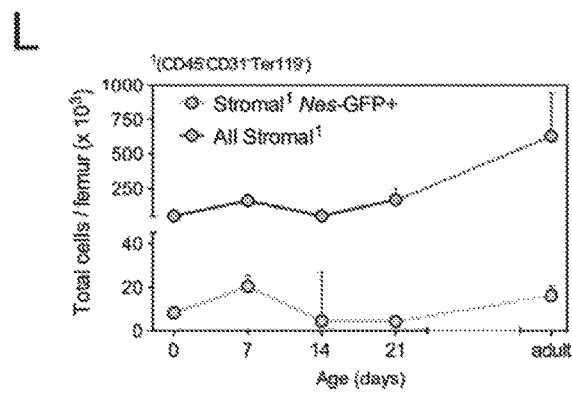

Example 2. Fetal BM Nestin+ Cells are Quiescent and Distinct from Osteochondral Cells We have shown previously that, in the adult murine BM, stromal cells expressing the green fluorescent protein (GFP)

under the regulatory elements of nestin promoter (Nes-GFP+) displayed both HSC– niche and MSC features (Mendez-Ferrer et al., 2010). We first characterized Nes-GFP+ cells during limb BM development. At E18.5 Nes-GFP+ cells were frequently associated with arterioles and sprouting endothelial cells within the osteochondral junction (FIG. 14a-c). Fetal BM Nes-GFP+ cells were heterogeneous and comprised not only a majority of BMSCs, but also a small subset of CD31+ putative endothelial cells that increased during the postnatal period (FIGS. 14d-e). Compared with Nes-GFP− BMSCs, the Nes-GFP+ cell population was enriched in endogenous Nestin mRNA expression (FIG. 14f). By fluorescent microscopy, arterioles appeared brighter for GFP because they contained several concentric GFP+ cells, including an outer layer that expressed smooth muscle actin and an inner layer of endothelial cells (FIG. 14g). Fetal BM Nes-GFP+ cells were distinct from chondrocytes expressing S100 and osteoblastic cells genetically labeled by the 2.3-kilobase proximal fragment of the α1(I)-collagen promoter (Dacquin et al., 2002) (FIG. 14H-J). Contrasting the marked proliferation of Nes-GFP− BMSCs in perinatal life, Nes-GFP+ cells remained mostly quiescent (FIG. 14k). As a result, Nes-GFP− BMSCs steadily expanded, while Nes-GFP+ BMSC number did not significantly change (FIG. 14l).

Example 3. BM Nestin+ Cells do not Contribute to Fetal Endochondrogenesis

Figure 15:
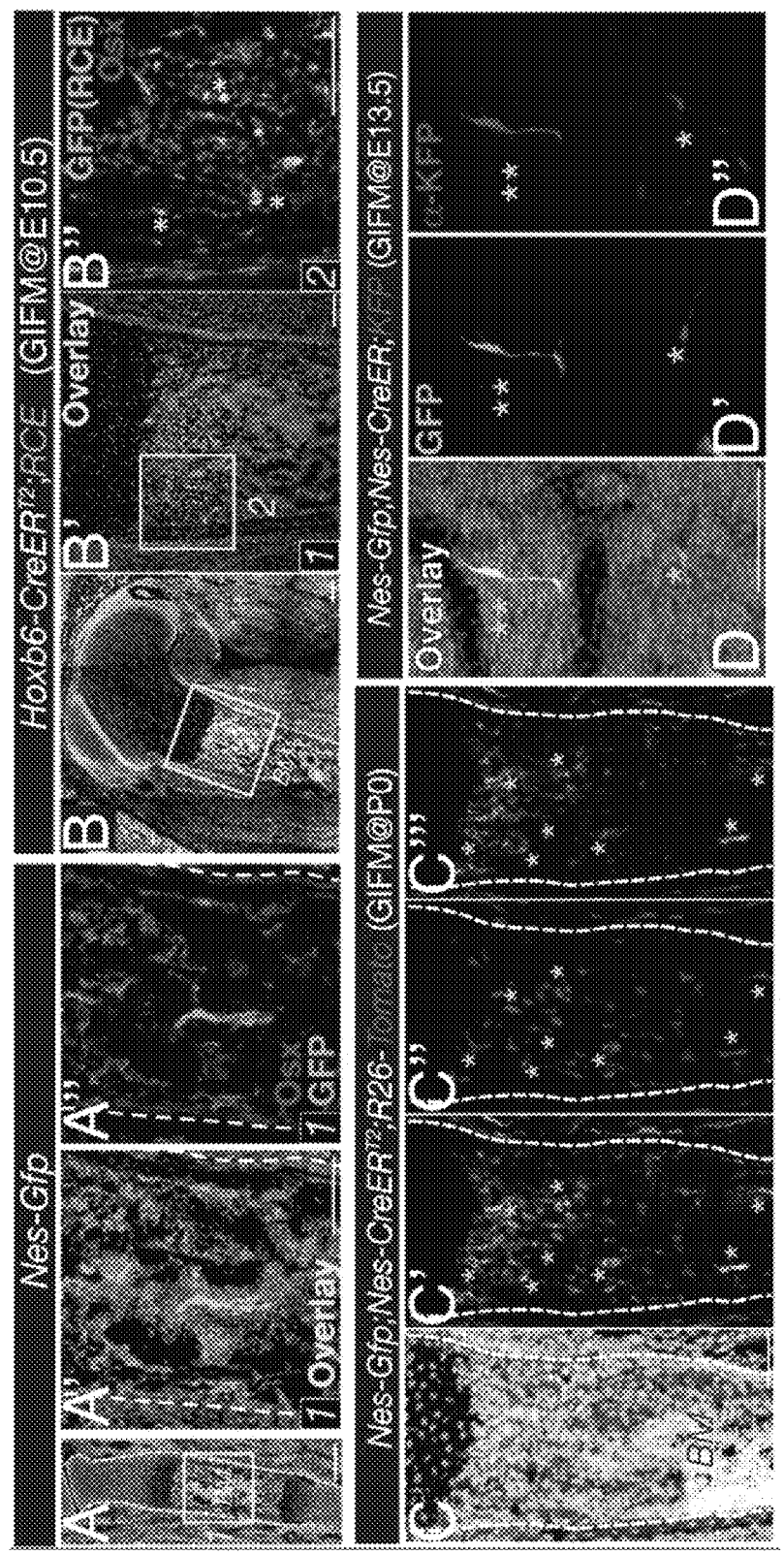
FIG. 15. BM nestin$^+$ cells are different from mesodermal osteo-chondroprogenitors. a-b, Femoral BM sections from P1 Nes-Gfp and E18.5 Hoxb6-CreER$^{T2}$;RCE (tamoxifen-induced at E10.5) immunostained with Osterix antibodies (Osx, red) to label osteoprogenitor cells. RCE$^+$ Osx$^+$ mesodermal osteoprogenitors are marked with asterisks. c, Perinatal recombination in Nes-CreER$^{T2}$ mice efficiently targets BM stromal Nes-GFP$^+$ cells. BM section of P7 Nes-Gfp; Nes-CreER$^{T2}$;R26-Tomato mouse that received tamoxifen at birth, showing Nes-GFP$^+$ cells (green), Nes-derived progeny and double-positive cells (asterisks). d, High magnification of BM section from P7 Nes-GFP;Nes-CreER$^{T2}$;KFP mouse treated with tamoxifen at E13.5. Nes-GFP$^+$ cells stained with anti-KFP antibody (red) are indicated (**). e-g, Fate mapping of the progeny of nestin$^+$ cells and limb mesoderm in E18.5/19.5 (e, g) Nes-Cre$^{ERT2}$;RCE and (f) Hoxb6-CreER;RCE femoral BM, respectively. e, GFP and nuclei counterstained with dapi in mice treated with tamoxifen at E13.5. Neither proliferating (*) nor hypertrophic (**) chondrocytes showed GFP fluorescence (inset 1). (e'-e") Nes-derived cells with a similar morphology and distribution to Nes-GFP$^+$ cells were detected near the cartilage-perichondrium interface (arrows) and within the chondro-osseous junction (arrowheads). (F-G) f-g, Femoral BM sections of (f) Hoxb6-CreER;RCE and (g) Nes-Cre$^{ERT2}$; RCE mice treated with tamoxifen at E10.5/8.5, respectively, stained with S100 antibodies to label chondrocytes. (f'-f") High magnification of cartilage (inset 1), showing abundant double-positive chondrocytes (arrowheads). g, Nes-traced cells were not chondrocytes (red, *) but infiltrated the chondro-osseous junction and trabecular bone (arrowheads). Scale bars: 200 μm (a-b, f), 100 μm (c-e, g). BM, bone marrow; C, cartilage; GIFM, genetic inducible fate mapping.
Figure 15:
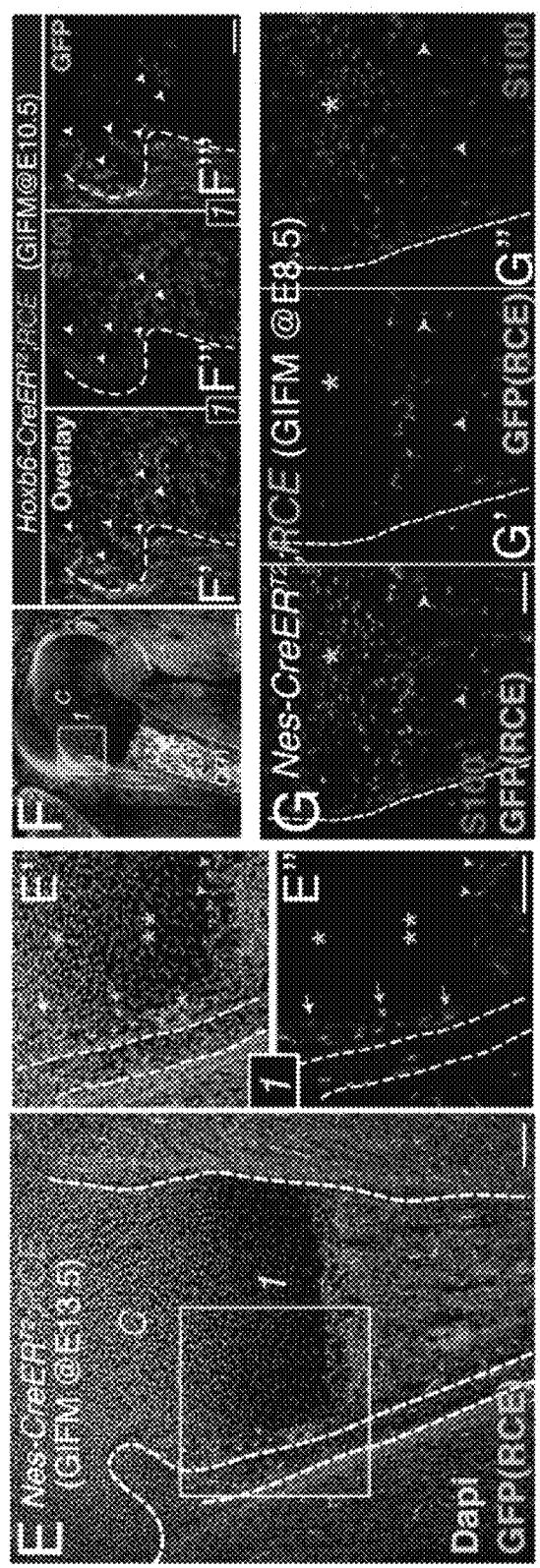

Axial and appendicular skeleton is thought to originate solely from mesoderm. During endochondral ossification, cartilage composed by chondrocytes is progressively replaced by osteoblast precursors that express the transcription factor osterix and infiltrate the perichondrium associated with invading blood vessels (Maes et al., 2010). We performed lineage-tracing studies by crossing RCE reporter mice (Sousa et al., 2009) with mice expressing inducible Cre recombinase under the regulatory elements of Hoxb6 gene, which is expressed in lateral plate mesoderm (Nguyen et al., 2009). The resulting double-transgenic mice were administered tamoxifen at E10.5 and embryos were analyzed for osterix expression at E18.5. Unlike cells derived from lateral plate mesoderm, fetal limb BM Nes-GFP+ cells did not express osterix protein (FIG. 15a-b) and thus could not be considered osteoblast precursors.

We next performed genetic inducible fate mapping using Nes-CreER$^{T2}$ mice (Balordi and Fishell, 2007), in which, upon tamoxifen administration, Nes-GFP+ cells and their progeny are labeled (FIG. 15c-d). Tamoxifen was administered at E13.5 (when primary ossification centers start forming) (Maes et al., 2010), and at E8.5, to mark earlier nestin+ embryonic precursors. Unlike Hoxb6-traced mesodermal derivatives, nestin+ cells did not contribute to the formation of cartilage during this period. In contrast, Nes-traced cells with similar morphology and distribution as Nes-GFP+ cells were observed in the chondro-osseous junction (FIG. 15e-g).

Figure 16:
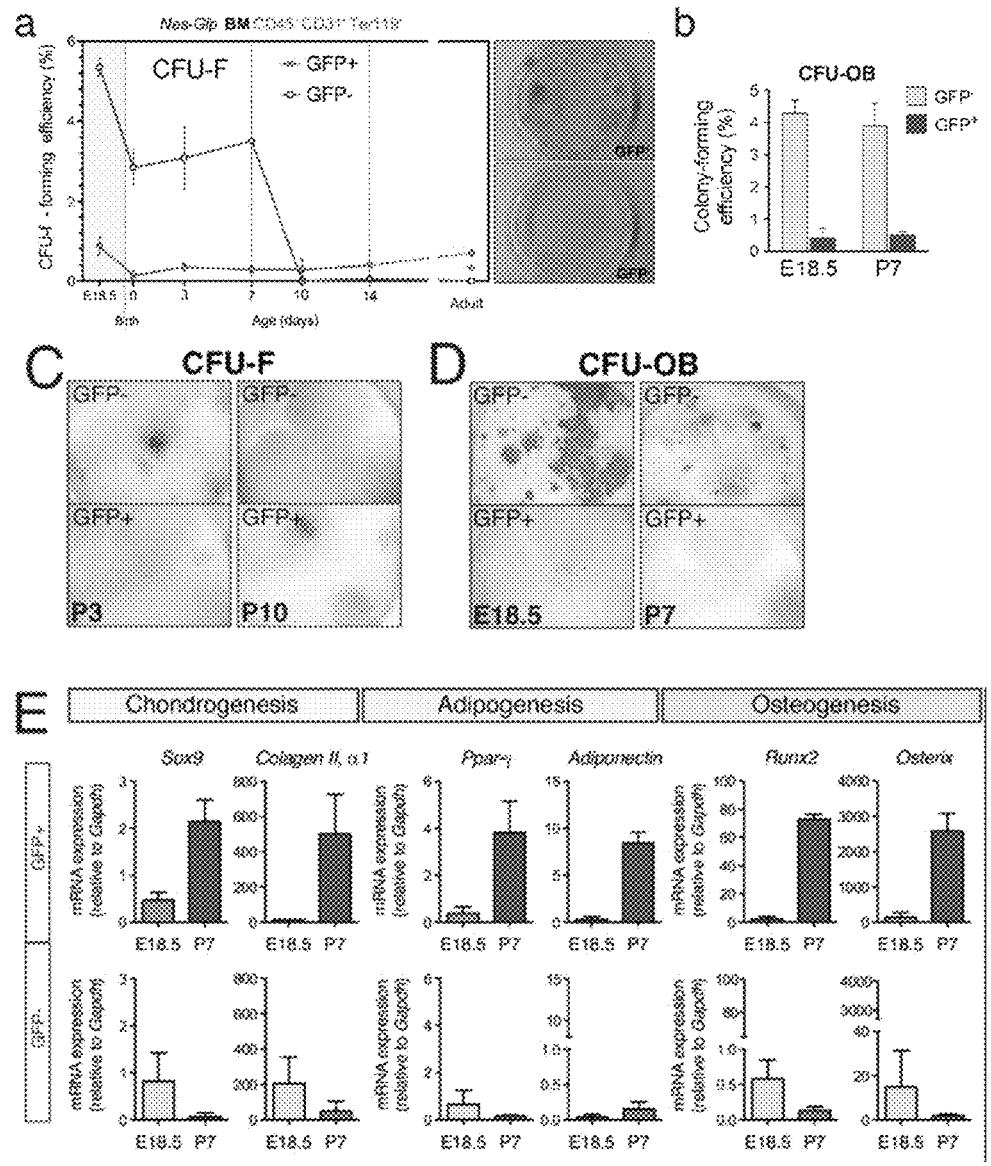
FIG. 16. Perinatal enrichment of MSC activity in BM nestin$^+$ cells. a, MSC activity is progressively restricted to BM Nes-GFP$^+$ cells. Frequency of fibroblastic colony-forming units (CFU-F) in stromal (CD45$^-$CD31$^-$Ter119$^-$) GFP$^{+/-}$ cells isolated from the BM of Nes-Gfp mice of indicated age. Representative CFU-F in cell populations from young mice (right panels). b, Frequency of osteoblastic colony-forming units (CFU-OB) in BM stromal GFP$^{+/-}$ cells at indicated age. c, Representative Giemsa-stained CFU-F from 3- and 10-day-old BM subpopulations. d, Stained CFU-OB from E18.5 (alkaline phosphatase staining, left panels) and 1-week-old (alizarin staining, right panels) BM subpopulations. e, QPCR analyses of mesenchymal genes in BM stromal populations isolated from fetal (E18.5) or 1-week-old (P7) Nes-Gfp mice, f-g, CFU-F and mesensphere-forming activities segregate in fetal BM Nes-GFP$^-$ and Nes-GFP$^+$ cells, respectively. CFU-F and mesensphere-forming efficiency, in E17.5 Nes-Gfp embryos. a-g, Mean±SD, n=3-6; *p<0.05, unpaired two-tailed t test. h-l, Representative spheres from both mesenchymal subpopulations. Note the presence of GFP$^+$ fibroblastic-like cells FIG. 17. Low contribution of adult nestin$^+$ MSCs to physiological skeletal turnover. a, Diagram illustrating two experimental paradigms to delete adult nestin$^+$ cells (TM, tamoxifen; DT, diphtheria toxin). a-c, Nes-CreER$^{T2}$;iDTR double transgenic mice (red bars) and iDTR control littermates were repeatedly injected with tamoxifen and diphtheria toxin to delete nestin$^+$ cells. b, Bone mineral density (BMD) of the spine was measured 1-10 months after initiating treatment. c, Fibroblastic colony-forming units (CFU-F). d, Frequency of osteoblastic colony-forming units (CFU-OB) positive for alizarin, alkaline phosphatase (ALP) and Von Kossa stainings. E-F, Tartrate-resistant acid phosphatase (TRAP) staining in femur of representative control (e) and experimental (f) mice. g, Number of TRAP$^+$ osteoclasts normalized per bone perimeter. (h-l) Bone histomorphometry analyses of (h) mineralizing surface, (l) mineral aposition and (j) bone formation rates. (k-l) Representative vertebral sections from control (k) and experimental (l) mice injected with calcein (green, 10 mg/kg, i.p.) and xylenol orange (orange, 90 mg/kg, i.p.) 6 and 3 days before sacrifice, respectively. Decreased distance between calcium deposition layers in experimental mice indicates reduced osteoblastic activity. (m-o) μCT of Nes-CreER$^{T2}$;iDTA double-transgenic mice and Nes-CreER$^{T2}$ control littermates injected with tamoxifen at adulthood and fed with tamoxifen diet for 6 months to delete nestin$^+$ cells. Note (n) Osteolytic lesions and (o) bilateral asymmetry in skull bones of experimental mice.
Figure 16:
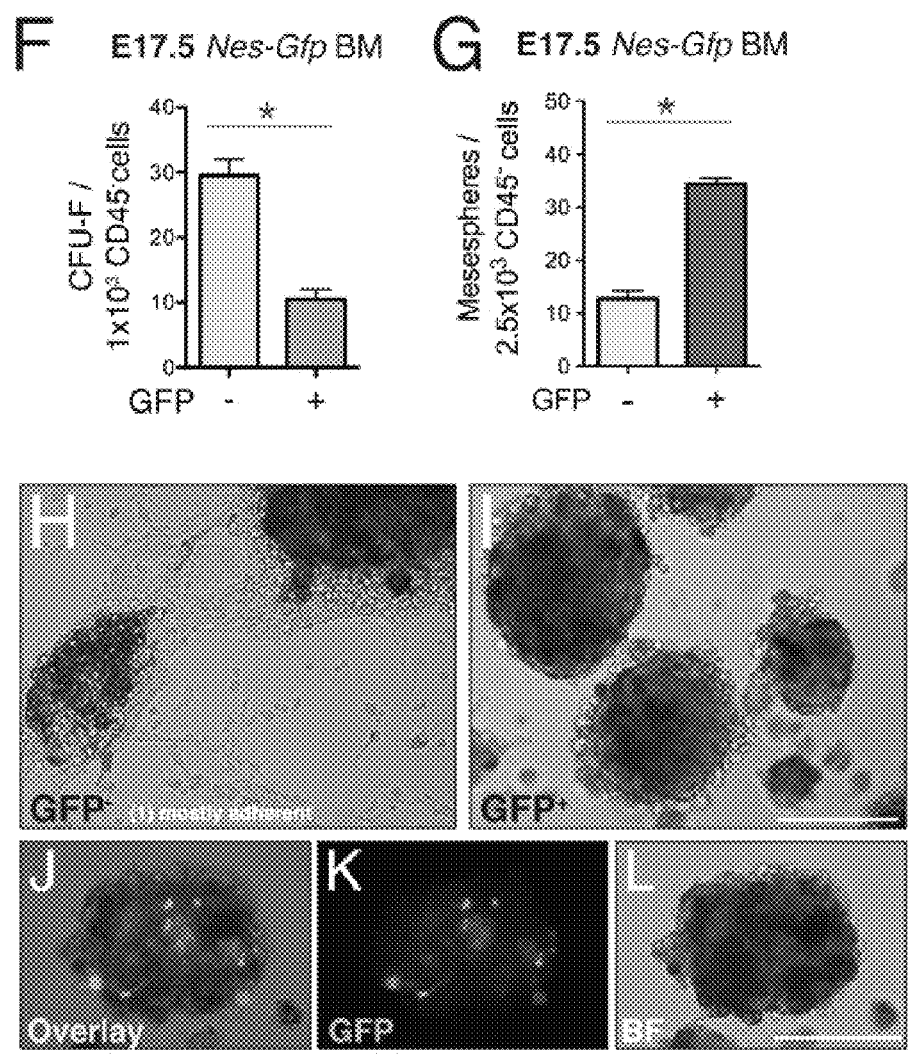

Example 4. BMSC Progenitor Activity is Progressively Restricted to Nestin+ Cells The lack of contribution of nestin+ cells to fetal endochondrogenesis raised questions regarding their MSC properties in fetal BM. We therefore measured mesenchymal progenitor activity in purified BM stromal subsets using the fibroblastic colony-forming unit (Cfu-f) (Friedenstein et al., 1970) and mesensphere-forming (Mendez-Ferrer et al., 2010) assays. BMSCs were isolated according to Nes-GFP expression. During late development and first postnatal week, Cfu-f frequency was 6-fold higher in the GFP− stromal population than in GFP+ cells (FIG. 16a). Strikingly, at later postnatal stages Cfu-f activity was progressively restricted to Nes-GFP+ cells due to its dramatic drop in GFP− BMSCs (>100-fold vs. 0.5-fold reduction during E18.5-P14, respectively). At P7, Cfu-f derived from Nes-GFP-cells mostly contained preosteoblasts (FIG. 16b-d). The expression of genes associated with chondrocyte development was higher in Nes-GFP− than in Nes-GFP+ BMSCs at E18.5; in contrast, the expression of master regulators of chondrogenesis, osteogenesis and adipogenesis was progressively enriched in postnatal Nes-GFP+ BMSCs, consistent with the increasing MSC enrichment (FIG. 16e). Together, these results suggest that most fetal BMSCs do not express nestin and quickly differentiate towards committed skeletal precursors, losing MSC activity by the second week after birth. In contrast, nestin+ cells show a conserved MSC activity throughout life.

Example 5. Fetal BM Nes-GFP+ Cells are Enriched in Mesensphere-Forming Cells

We have previously shown that, under similar culture conditions used to grow NC cells, adult murine BM Nes-GFP+ cells can form self-renewing and multipotent mesenchymal spheres capable of transferring hematopoietic activity to ectopic sites during serial transplantations (Mendez-Ferrer et al., 2010). In addition, we have shown that human BM-derived mesenspheres can expand human cord blood HSCs through secreted factors (Isern et al., 2013b). We measured mesenchymal progenitor activity in fetal BMSCs. Cfu-f efficiency was nearly three times higher in Nes-GFP− than in Nes-GFP+ cells at E17.5 (FIG. 3f). Conversely, non-adherent sphere formation was markedly enriched in GFP+ cells, while most spheres derived from GFP− cells rapidly attached to plastic and spontaneously differentiated (FIG. 16g-h). Spheres formed by BM Nes-GFP+ cells contained mesenchymal-like spindle-shaped GFP+ cells (FIG. 16i-l).

Example 6. Minimal Contribution of Nestin+ MSCs to Adult Skeletal Turnover

Figure 17:
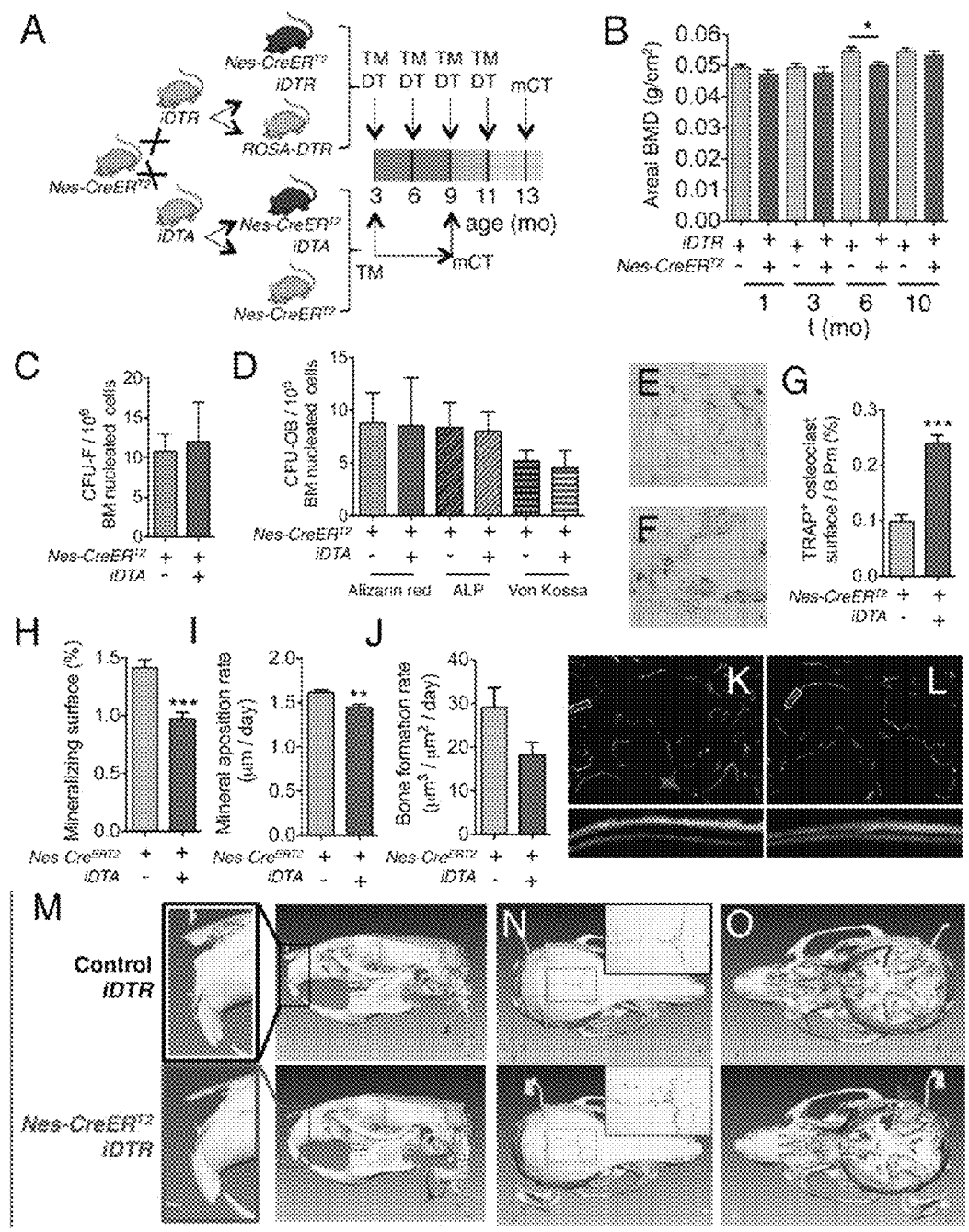

BMSCs expressing Mx1-cre driver participate in bone turnover (Park et al., 2012) but their overlap with nestin+ MSCs remains unclear. Our results show that MSC activity becomes progressively restricted to BM Nes-GFP+ cells, which highly expressed genes involved in osteogenesis at postnatal stages (FIG. 16e). In addition, our studies have suggested a low contribution of nestin+ cells to adult osteochondral lineages (Mendez-Ferrer et al., 2010). We studied skeletal remodeling after longitudinal bone growth using two independent loss-of-function models. Nes-CreER$^{T2}$ mice were intercrossed with the Cre-recombinase-inducible lines expressing either diphtheria toxin (iDTA) (Brockschnieder et al., 2006) or its receptor (iDTR). Double-transgenic and control littermate mice were chronically administered diphtheria toxin and/or tamoxifen at adulthood (FIG. 17a). Bone densitometry showed only a transient reduction in vertebral mineral density (BMD) at 6 months following depletion of nestin+ cells (FIG. 17b). Consistent with this, when sacrificed at term, the experimental mice showed no difference in mesenchymal or osteoblastic activity (FIG. 17c-d). In contrast, histomorphometry revealed an increased number of osteoclasts and decreased mineralizing activity (FIG. 17e-l). Although all vertebral (mesoderm-derived) skeletal parameters were normal (not shown), several abnormalities were noted in NC-derived bones. These defects included reduced ossification of nasal bone and premaxilla, osteolytic skull lesions and bilateral asymmetry (FIG. 17m-o). Together, these results demonstrate modest skeletal defects in adult mice where nestin$^+$ cells were eliminated genetically. Therefore, although MSC activity is largely confined within adult nestin$^+$ cells, they show a relatively minor contribution to physiological turnover of axial skeleton and thus behave in a distinct manner from Mx1-cre-traced mesenchymal derivatives (Park et al., 2012).

Example 7. The Trunk Neural Crest Contributes to BM Nestin$^+$ MSCs

Figure 18A:
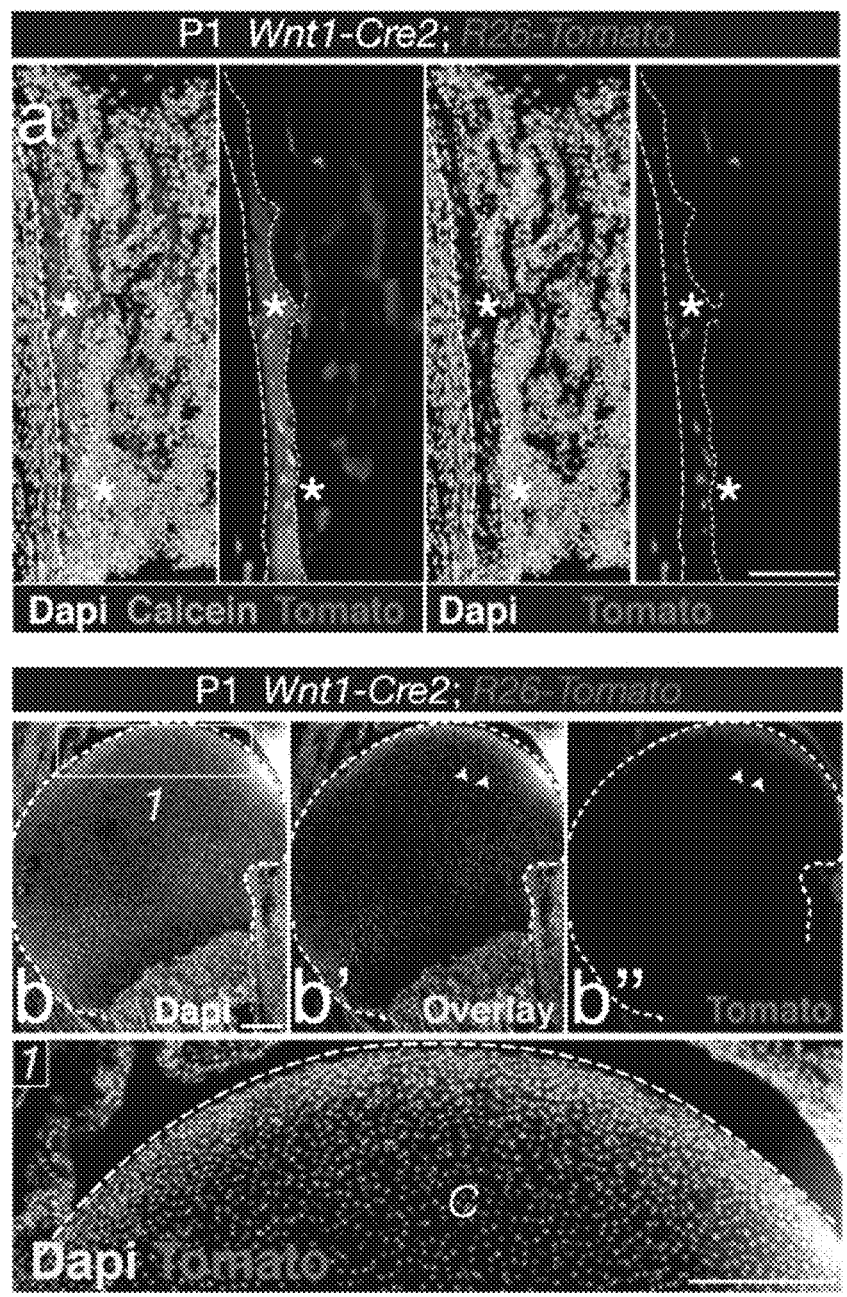
FIG. 18. Contribution of trunk neural crest cells to mesenchymal lineages in long bones. a-f, Fate mapping of NC derivatives in femoral BM of neonatal Wnt1-Cre2;R26-Tomato mice. a, BM section stained with calcein to mark calcium deposition showing Wnt1-Cre2-traced Tomato+ osteoblasts in calcifying areas (asterisks). Scale bar=100 μm). b, Section through femoral head showing cortical NC-derived chondrocytes (arrowheads). Scale bars=200 μm). Nuclei were counterstained with dapi. c-e, Diaphysis section stained with antibodies against glial fibrillary acidic protein (Gfap, cyan). NC-traced cells included Gfap Schwann cells (inset 1, arrowheads) and gfap⁻ putative BMSCs (inset 2, asterisks). f, Staining of basal lamina with Colagen IV antibodies showing close association of NC-derived cells with blood vessels. g, NC-derived osteoblastic cells near endosteal surfaces and within calcein-stained calcifying regions. h-k, NC contributes to PDGFRα⁺ BMSCs in long bones. Representative FACS of CD45⁻CD31⁻Ter119⁻ BM cells from neonatal (h) Nes-Gfp or (i) Wnt1-Cre2;R26-Tomato mice, and fetal (j) Nes-Gfp or (k) Nes-Gfp;Sox10-CreER$^{T2}$;R26-Tomato triple-transgenic mice stained with PDGFRα antibody. (l,k) Frequencies of NC-traced BMSCs are indicated. Scale bars: 200 μm (b,b1, c), 100 μm (a,f,g), 50 m, (d-e).
Figure 18B:
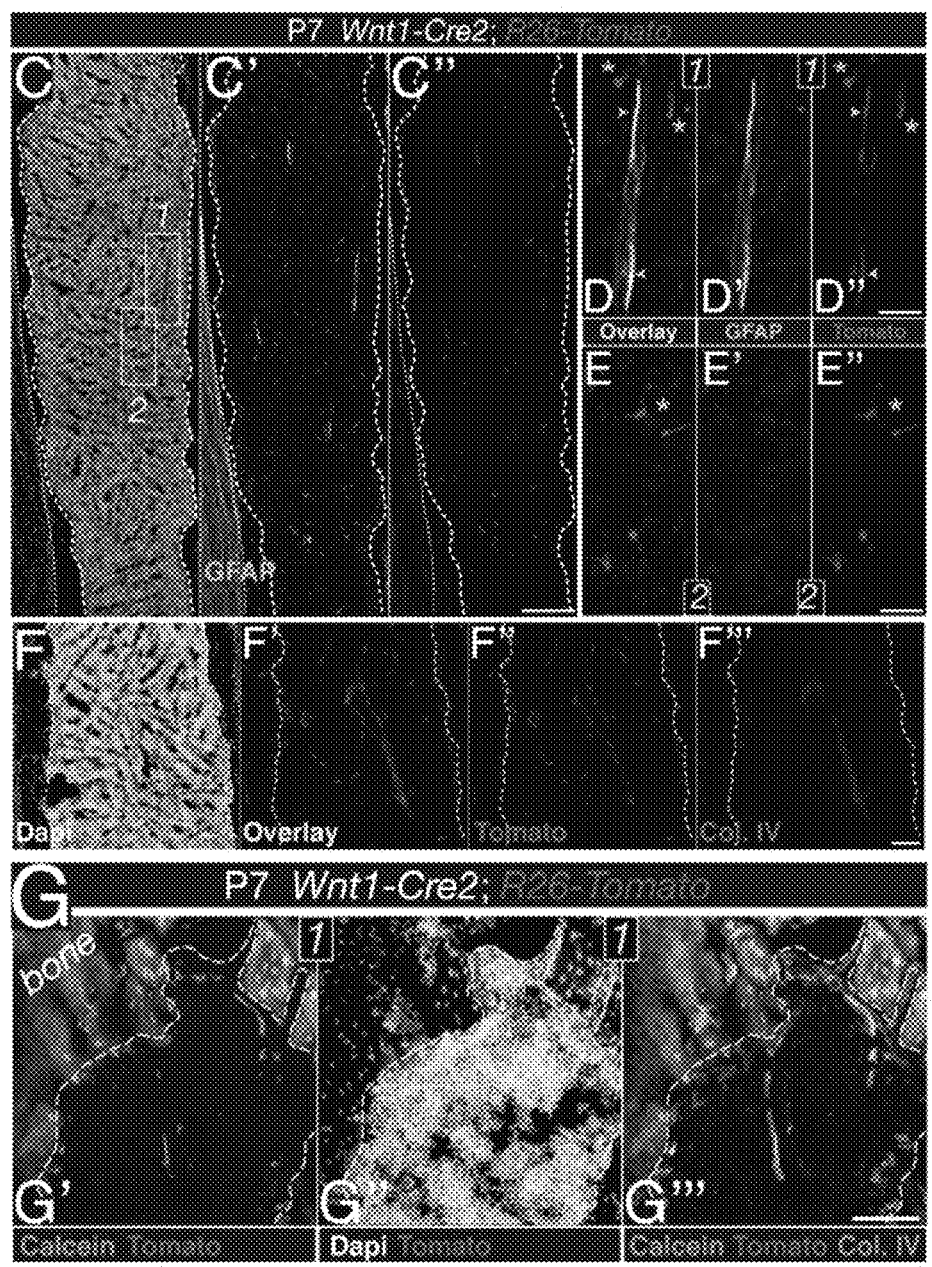
Figure 18C:
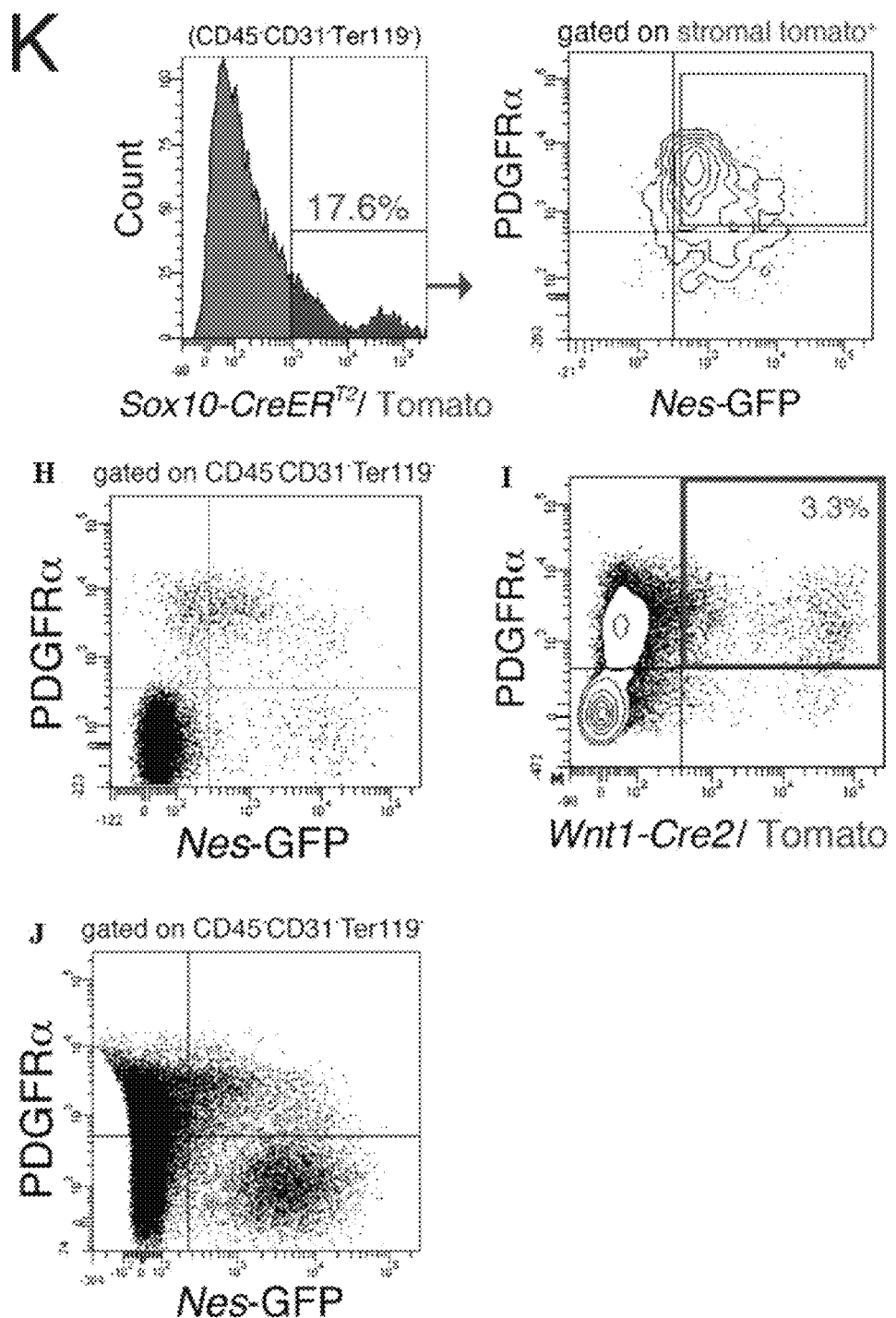

NC cells are characterized by nestin expression and sphere-forming ability. Although cells traced to NC origin have been previously reported in adult murine BM (Gleizer et al., 2011; Komada et al., 2012; Morikawa et al., 2009b; Naqoshi et al., 2008), their precise identity, developmental dynamics and function have remained elusive. Also, ectopic Wnt1 activation has been reported in Wnt1-Cre mice used in these studies (Lewis et al., 2013). We performed genetic fate-mapping studies with a recent Wnt1-Cre2 line that does not induce ectopic Wnt1 activity (Lewis et al., 2013). Unexpectedly, limb bones from neonatal Wnt1-Cre2;R26-Tomato double-transgenic mice showed NC-derived osteoblasts and osteocytes aligning the most recent layers of bone deposition, as well as chondrocytes that were distributed similarly in the outermost layers of femur head (FIG. 18a-b). As expected, NC-traced Schwann cells expressing the glial fibrillary acidic protein (GFAP) were also detected in one week-old BM (FIG. 18c-d). Intriguingly, GFAP$^-$ perivascular cells with similar morphology and distribution to Nes-GFP$^+$ cells were also derived from Wnt1$^+$ cells (FIG. 18e-f). The number of NC-traced osteochondral cells increased in the first postnatal week (FIG. 18g), suggesting that NC contributes to limb bones in late development. In confirmation, the widely used Wnt1-Cre line also showed persistence of NC-traced cells in adult BM. Of note, most adult NC fate-mapped cells expressed nestin and many were associated with sympathetic nerve fibers (data not shown); the latter represents another NC derivative, which we have previously implicated in the control of circadian HSC traffic (Mendez-Ferrer et al., 2008) through the regulation of nestin$^+$ MSCs (Mendez-Ferrer et al., 2010).

Murine PDGFRα$^+$ (BMSCs are highly enriched in CFU-F activity (Morikawa et al., 2009a; Takashima et al., 2007) and most adult murine BM nestin$^+$ cells are also PDGFRα (Pinho et al., 2013; Yamazaki et al., 2011). We found that fetal PDGFRα (BMSCs were also enriched in Cfu-f activity. Both neonatal stromal Nes-GFP$^+$ and Wnt1-Cre2-traced cells contained PDGFRα$^+$ and PDGFRα$^-$ cells (FIG. 18h-i), suggesting a considerable overlap between these cell populations. For confirmation, we intercrossed Nes-Gfp;R26-Tomato mice with a line expressing tamoxifen-inducible Cre recombinase under the regulatory elements of the NC transcription factor Sox10. Nes-Gfp;Sox10-CreER$^{T2}$;R26-Tomato mice were administered tamoxifen at E9.5 to label migratory NC. Similar to stage-matched Nes-Gfp mice, two E18.5 BM populations segregated according to PDGFRα expression in NC derivatives (FIG. 18j-k). These results thus demonstrate definitively that NC contributes to nestin$^+$ BMSCs.

Figure 19:
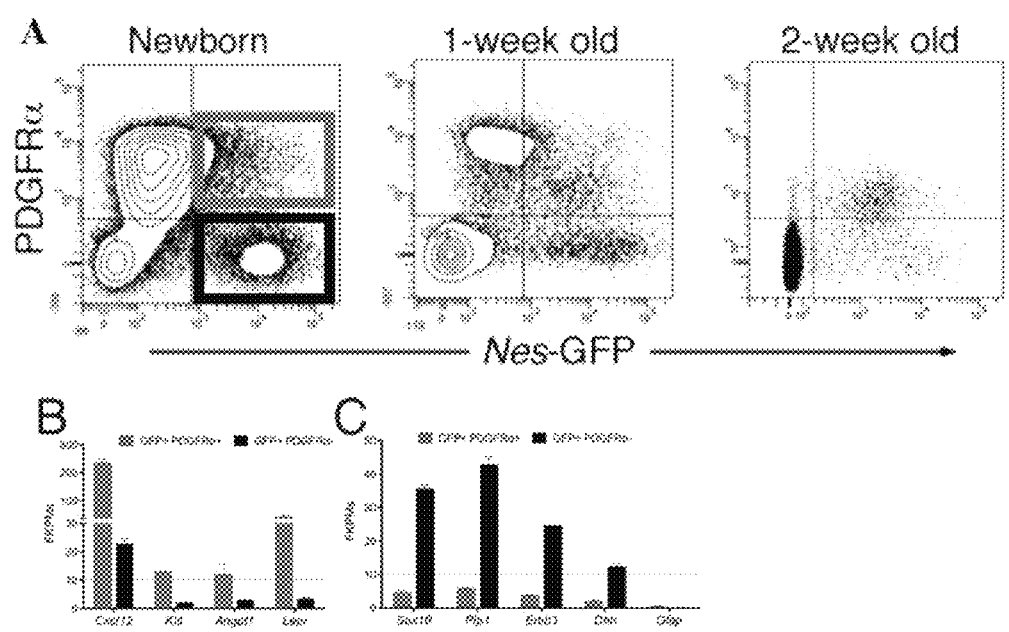
FIG. 19. BM Nestin-GFP⁺ cells contain PDGFR□⁺ MSCs and PDGFR□⁻ Schwann cell precursors a, Representative FACS profiles of Nes-GFP and PDGFRα expression in postnatal BMSCs. b, Selected transcript expression of isolated Nes-GFP$^{++/-}$ PDGFRα$^{+/+}$ BMSCs depicted in (a). b-c, Relative expression levels of (b) HSC niche-related and (c) Schwann cell progenitor genes by GFP⁺PDGFRα⁺ or GFP⁺ PDGFRα⁻ BMSCs. RNAseq data is expressed as fragments per kilobase of exon per million fragments mapped (FPKM; n=2 independent samples from pooled newborns). Note that neonatal GFP⁺ PDGRα⁻ subpopulation has Schwann cell progenitor signature (c) while GFP⁺ PDGRα⁺ cells are enriched in HSC maintenance genes. d, Principal component analyses of neonatal Nes-Gfp BM stromal subsets compared with representative NC-derived populations and primary adult murine BMSCs (detailed in Table S3). e-f, In vitro differentiation of neonatal subpopulations isolated as in (a) and cultured in mesenchymal (+PDGF) and Schwann cell (+Nrg-1) differentiation media. Adipocytes were stained with Oil Red O and counterstained with hematoxylin (left panels); Schwann cells were stained with antibodies against glial fibrillary acidic protein (Gfap) and overlaid with endogenous GFP fluorescence (right panels). PDGF, recombinant murine platelet-derived growth factor A-B; Nrg-1, recombinant murine Neuregulin-1. Scale bars: 200 μm (top right insets: 50 μm).
Figure 19:
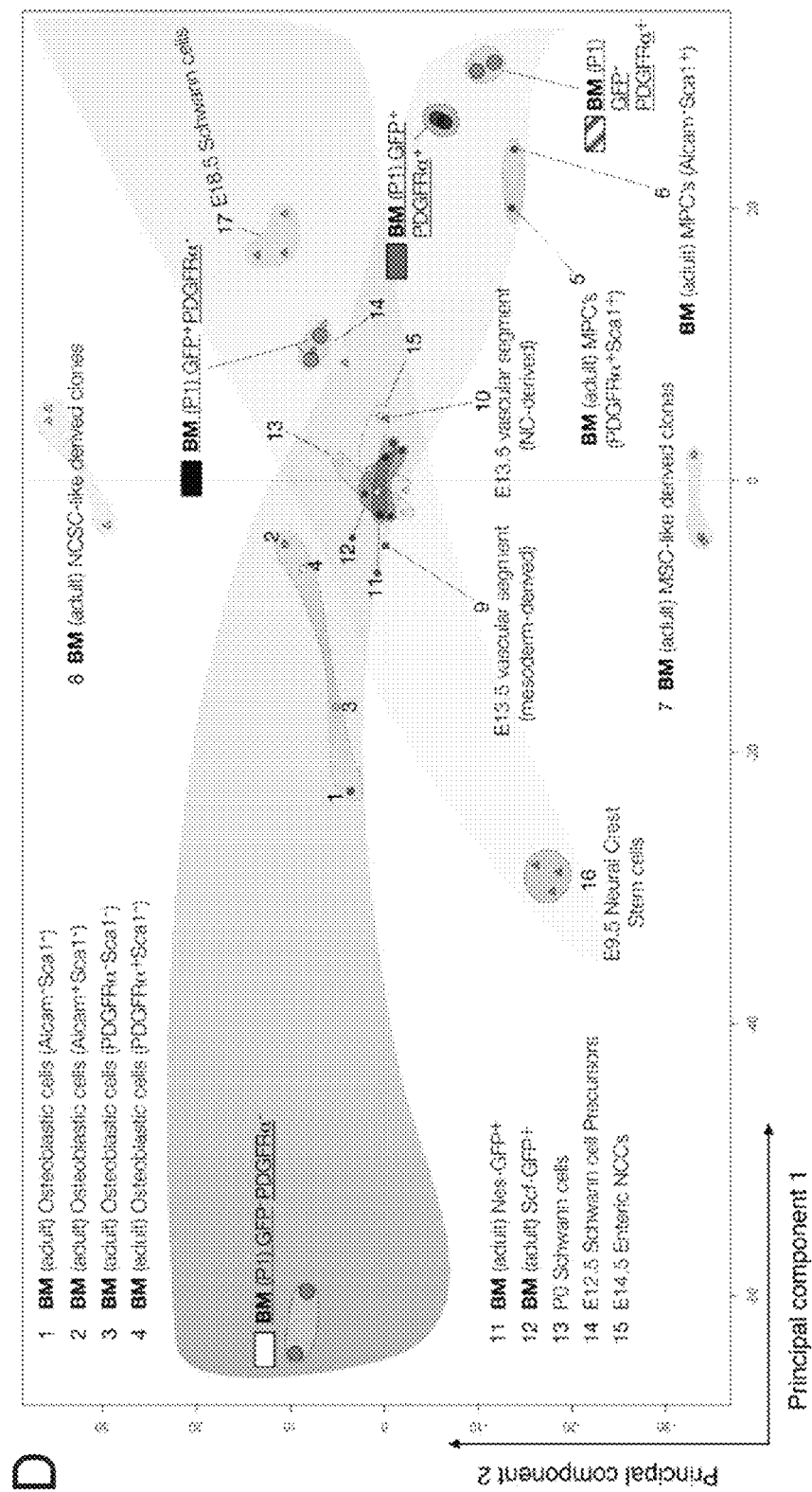
Figure 19:
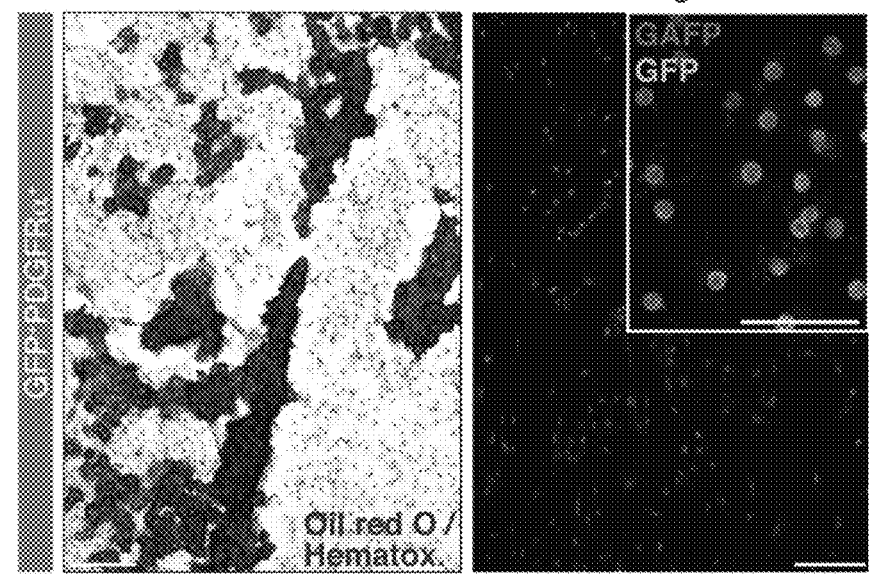
Figure 19:
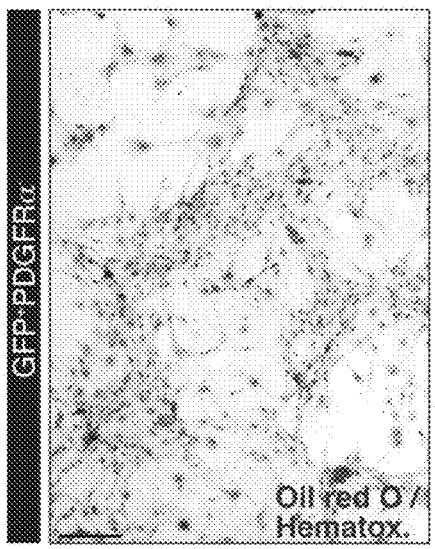
Figure 19:
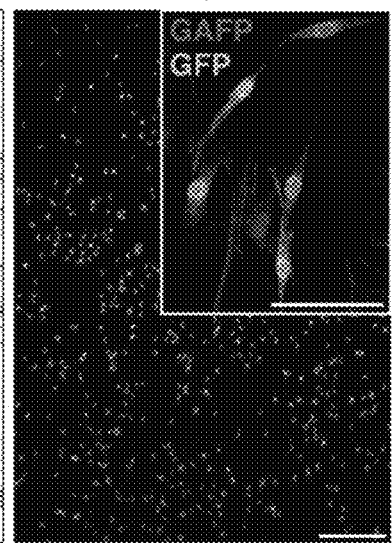

Example 8. BM Nes-GFP$^+$ Cells Comprise PDGFRα$^+$ MSCs and PDGFRα$^-$ Schwann Cell Precursors We studied the possible heterogeneity of fetal BM Nes-GFP$^+$ cells. It has been gleaned recently that most adult BM nestin$^+$ cells are PDGFRα, but also that nestin$^+$ PDGFRα$^-$ Schwann cells contribute to maintain HSCs (Yamazaki et al., 2011). We found that BM Nes-GFP$^+$ cells were closely associated with distinctive GFAP$^+$ Schwann cells (data not shown). We performed next-generation sequencing in neonatal GFP$^{/-}$ PDGFRα$^{/-}$ BMSCs (FIG. 19a). Endogenous Pdgfrα and Nes transcripts proved that isolation strategy worked. Interestingly, Ly6a/Sca1 expression was higher in GFP-PDGFR□$^+$ cells (not shown), but the expression of HSC maintenance genes (Cxcl12, Kitl, Angpt1) and Leptin receptor, which marks HSC niche-forming mesenchymal cells (Ding et al., 2012), was highly enriched in GFP$^+$ PDGFRα$^+$ cells (FIG. 19b). Other MSC genes were also abundantly expressed in this population (FIG. S5C). In contrast, Nes-GFP$^+$PDGFRα$^-$ cells expressed genes characteristic of Schwann cell precursors (SCPs; Sox10, Pip1, Erbb3, Dhh) but did not express mature Schwann cell genes, such as Gfap (FIG. 19C).

To further characterize nestin$^+$ subpopulations, the transcriptome wide profile of neonatal Nes-GFP$^{+/-}$PDGFRα$^{+/-}$ BMSCs was compared to publicly available microarray expression datasets from primary adult BMSCs or NC derivatives. Unbiased hierarchical clustering and principal component analyses revealed that Nes-GFP$^+$PDGFRα$^+$ cells were more similar to adult primitive BMSCs and distinct from more differentiated osteoblastic cells (Nakamura et al., 2010). PDGFRα$^+$Nes-GFP$^{+/-}$ cells clustered nearby, consistent with PDGFRα becoming mostly restricted to Nes-GFP$^+$ cells in postnatal BM (FIG. 19a). In addition, Nes-GFP$^+$ PDGFRα$^+$ cells clustered far from Nes-GFP$^+$PDGFRα$^-$ cells, whose genomic profile was closest to E12.5 SCPs. MSC-like and NC stem cell-like derived clones (Gleizer et al., 2011) were markedly different, probably because they were cultured cells.

Intriguingly, we noted a maturation hierarchy of Schwann and osteolineage cells, from undifferentiated cells (FIG. 19d, lower corners) to more mature lineages (FIG. 19d, contralateral upper corners). Adult BM CD45$^-$Nes-GFP$^+$ cells (Mendez-Ferrer et al., 2010) converged with BM HSC niche cells identified by the expression of stem cell factor (Ding et al., 2012) at the intersection of these differentiation waves (FIG. 19d). These results argued for two nestin$^+$ populations with non-overlapping MSC and SCP features. To test this hypothesis functionally, neonatal Nes-GFP$^{+/-}$PDGFRα$^{+/-}$ BMSCs were cultured in differentiation media. Remarkably, mesenchymal and glial differentiation segregated in PDGFRα$^{+/-}$ cells, respectively (FIGS. 19e-f). Together, these results show two Nes-GFP NC derivatives in postnatal BM, PDGFRα$^+$ MSCs enriched in HSC-supporting genes and PDGFRα$^-$ SCPs.

Figure 20:
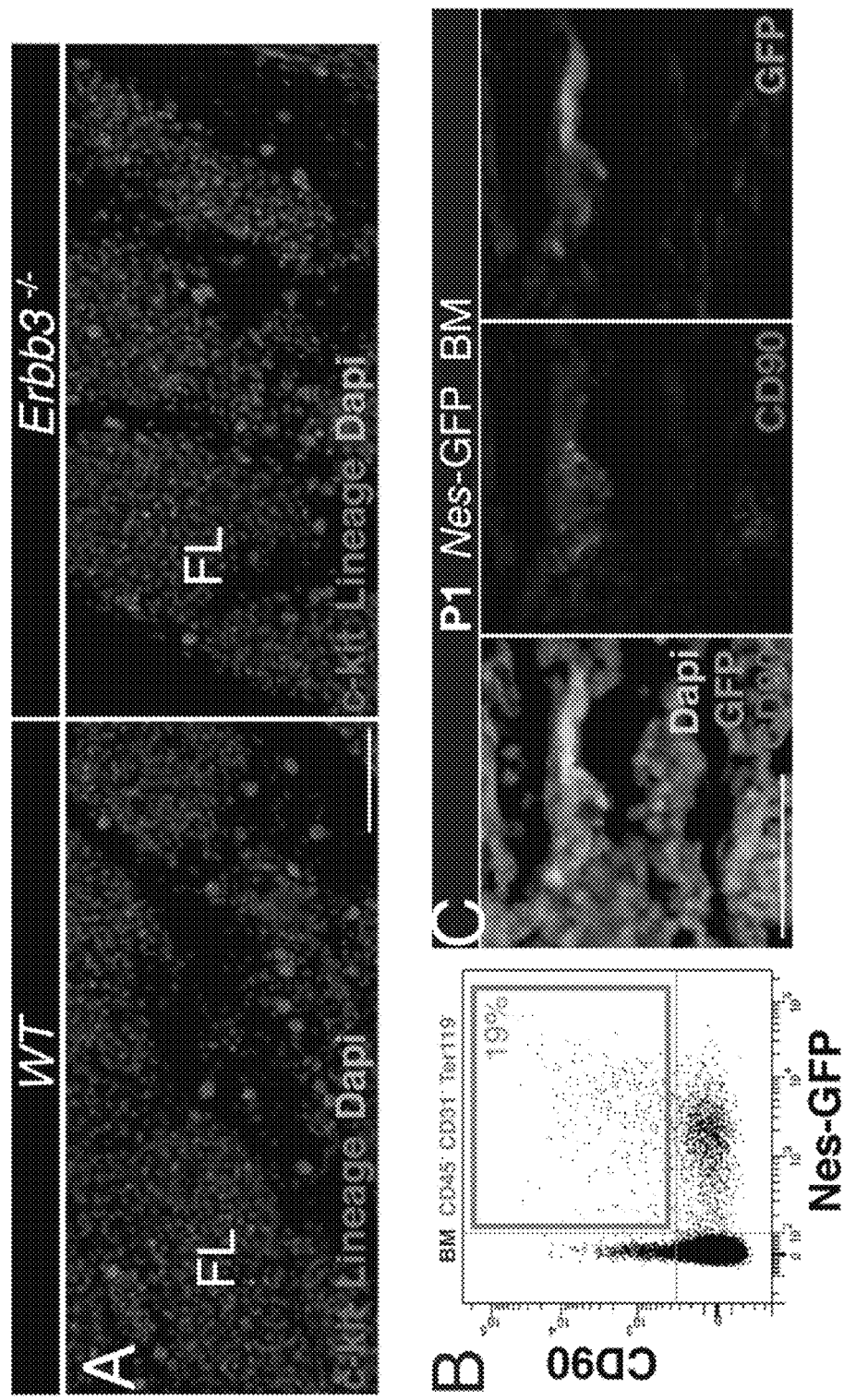
FIG. 20. Perineural migration of NC cells to long bones generates nestin⁺ MSCs with specialized HSC niche function. a, Fetal liver (FL) sections from wt and Erbb3-null embryos stained with mature hematopoietic lineage and c-kit antibodies. b, Representative FACS of CD45⁻CD31⁻Ter119⁻ BM cells from 2-week old Nes-Gfp mice stained with the mesenchymal marker CD90, showing the expression enrichment in Nes-GFP⁺ cells. c, Neonatal BM section stained with anti-CD90 antibodies that labeled Nes-GFP⁺ cells. Scale bar: 50 μm. d, Representative BM sections from Erbb3 wt and null E17.5/18.5 mice immunostained with anti-CD90. e, Quantification of CD90 immunostaining of samples in (d); n=3. f, Staining of BM sections from wt and Erbb3-null embryos with mature hematopoietic lineage and c-kit antibodies. g, Quantification of BM Lin⁻c-kit⁺ hematopoietic progenitors in E17.5/18.5 wt and Erbb3-null mice (n=3). (e,g) Mean±SEM, *p<0.05, unpaired two-tailed t test.
Figure 20:
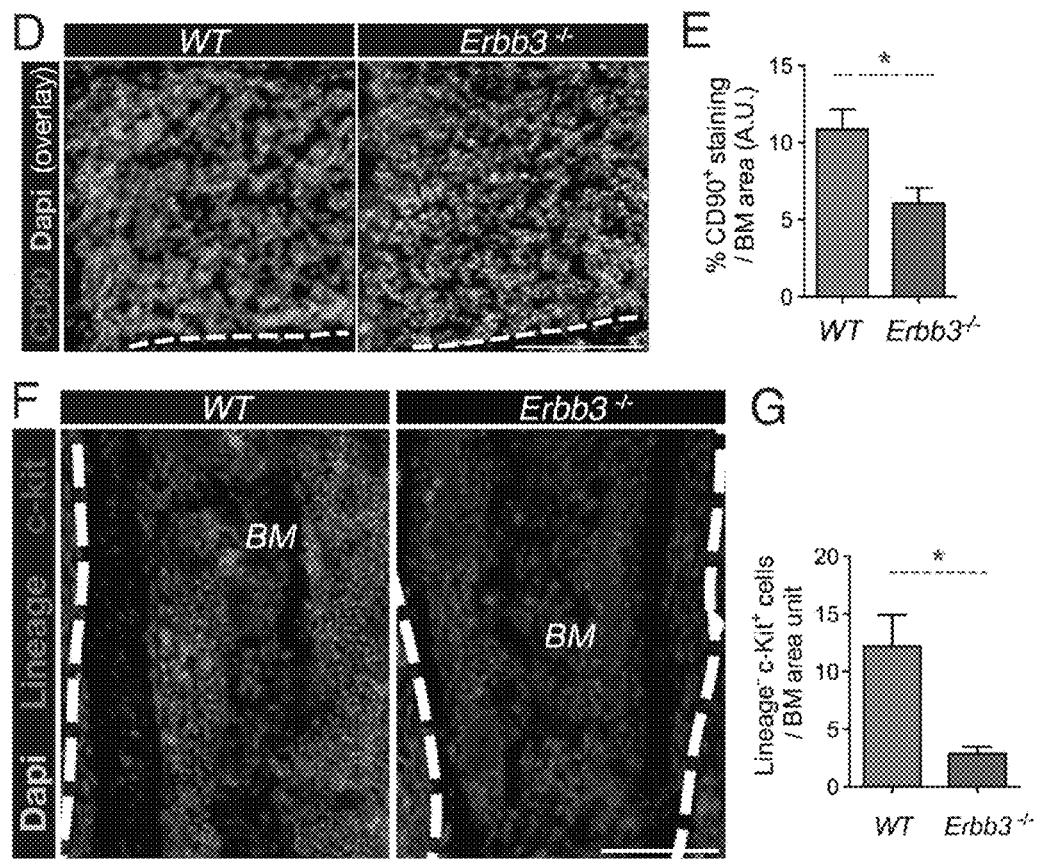

Example 9. Deficient Perineural NC Migration Reduces BMSCs and Compromises Developmental HSC BM Colonization Perineural SCP migration requires the interaction of receptor tyrosine-protein kinase ErbB3 with Neuregulin-1 ligand, produced by developing nerves (Jessen and Mirsky, 2005). We analyzed fetal liver and BM of Erbb3-deficient mice (Riethmacher et al., 1997). Fetal liver hematopoietic progenitors were unchanged (FIG. 20a). In contrast, expression of the MSC marker CD90, enriched in Nes-GFP$^+$ cells (FIG. 20b-c), was two-fold reduced in Erbb3$^{-/-}$ limb BM, associated with 5-fold decreased BM hematopoietic progenitors (FIG. 20d-g). To further dissect NC contribution to fetal hematopoiesis we performed similar analyses in mice lacking Erbb3 in Schwann-committed cells. R26-Tomato reporter mice intercrossed with a line expressing cre recombinase under the regulatory elements of desert hedgehog (Dhh) promoter (Jaegle et al., 2003) had labeled Schwann cells. Dhh-Cre mice were intercrossed with ErbB3 conditional deficient mice. Similarly to constitutive KO, Dhh-Cre;Erbb3$^{fl/fl}$ mice are virtually devoid of Schwann cells (Sheean et al., 2014). In contrast, Dhh-Cre;Erbb3$^{fl/fl}$ mice showed normal frequency of BM hematopoietic progenitors. These results suggest that NC cells not yet committed to Schwann cell lineage migrate along developing nerves to BM and contribute to HSC-niche forming MSCs.

Figure 21:
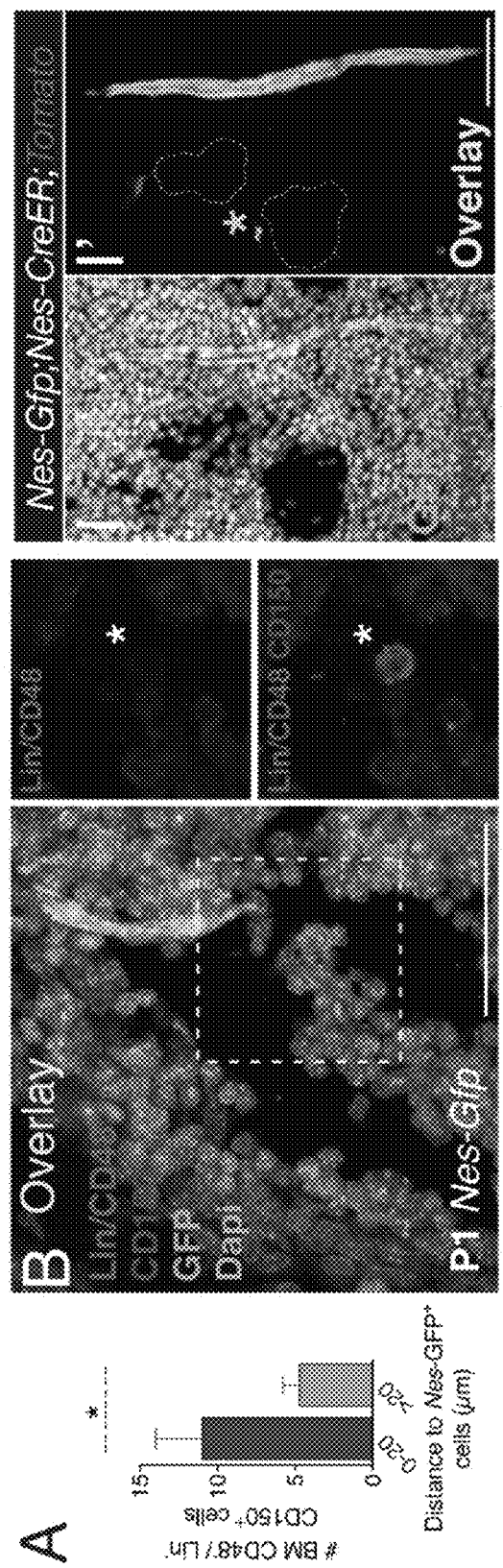
FIG. 21. CXCL12 produced by nestin⁺ MSCs contributes to establish the HSC niche in the BM. a-b, HSCs are localized near Nes-GFP⁺ cells in neonatal BM. Neonatal femoral sections from Nes-Gfp mice were immunostained with hematopoietic lineage, CD48 and CD150 antibodies. (A) Quantification of distance of Lin⁻CD48⁻CD150⁺ HSC-enriched cells to Nes-GFP⁺ cells (mean±SEM, n=41). b, Representative putative HSC (asterisk) near Nes-GFP⁺ cell. (C-F) Depletion of nestin⁺ cells compromises developmental HSC migration to BM. c-d, Long-term culture-initiating cell assay from E17.5 (c) liver and (d) BM cells from Nes-Cre$^{ERT2}$;iDTR (red dots) and control iDTR (black dots) mice treated with tamoxifen at E14.5 and diphtheria toxin at E15.5 (n=5-6). The percentage of culture dishes that failed to generate hematopoietic colony-forming units in culture (CFU-C) is plotted against five serial dilutions of (c) fetal liver Lin⁻ Sca1⁺ and (d) BM nucleated cells. HSC frequencies and p values are indicated. Pearson Chi-square test. e, Frequency of Lin⁻ Sca-1⁺ E17.5 liver cells in mice in (c). f, BM CFU-C content in 1-week old Nes-CreER;R26-DTA and control littermates treated with tamoxifen at birth (n=3-7). g, Expression of core HSC maintenance genes increases in perinatal Nes-GFP⁺ BMSCs. QPCR analyses of Cxcl12, stem cell factor/kit ligand (Kitl), angiopoietin-1 (Angpt1) and vascular cell adhesion molecule-1 (Vcam1) mRNA in CD45⁻CD31⁻Ter119⁻GFP$^{+/-}$ cells isolated from E18.5 and P7 Nes-Gfp BM. h, Relative Cxcl12 mRNA expression levels in endothelial cells and Nes-GFP$^{+/-}$ BMSCs isolated from 1 week-old mice (qPCR; n=2). i, Representative confocal picture of BM section of 1 week-old Nes-Gfp;Nes-CreER$^{T2}$;R26-Tomato mouse treated with tamoxifen at birth. Both arteriolar and sinusoidal (asterisk) GFP⁺ cells also express Nes-CreER$^{T2}$-derived Tomato reporter. j-k, Perinatal Cxcl12 excision efficiency by Nes-CreER$^{T2}$ driver in (j) stromal and (k) endothelial cells isolated from P7 BM. QPCR in CD45⁻Ter119⁻ CD31⁻ cells isolated from Cxcl12$^{f/f}$;Nes-CreER$^{T2}$ (e) and control (c) littermates treated with tamoxifen at birth (n=2-3). (l) BM CFU-C content in P7 Cxcl12$^{f/f}$;Nes-CreER$^{T2}$ and control littermates treated with tamoxifen at birth. (e,l) Each dot is a mouse. (f, h-j) Mean±SD. *p<0.05, unpaired two-tailed t test.
Figure 21:
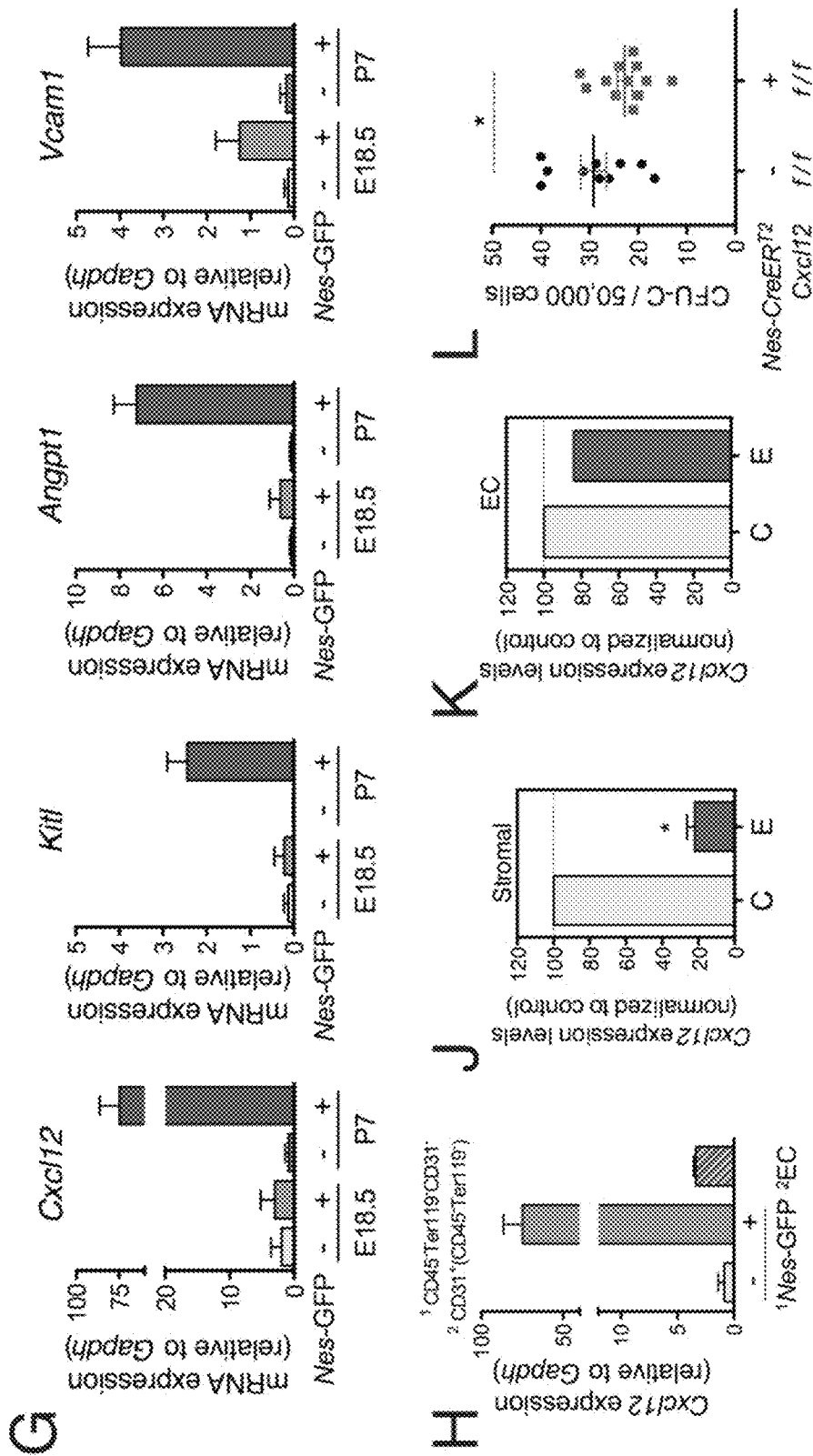

Example 10. NC-Derived Nestin$^+$ Cells Direct Developmental HSC Migration to BM Detailed immunofluorescence analyses showed significant proximity of HSCs to Nes-GFP$^+$ cells in neonatal BM (FIG. 21a-b). We studied the contribution of nestin$^+$ cells to HSC migration from fetal liver to BM using mice expressing the diphtheria toxin (iDTA) or its receptor (iDTR) in nestin$^+$ cells. Depletion of nestin$^+$ cells at E15.5 in Nes-CreER$^{T2}$; iDTR mice caused within 48 h ~4-fold reduction in fetal BM HSC activity, inversely correlated with ~8-fold increase in fetal liver HSC activity (FIG. 21c-d). While cell cycle profile or apoptosis of hematopoietic progenitors were unchanged (FIG. S7A), their numbers increased by 40% in fetal liver (FIG. 21e). Similar results were obtained by depleting nestin$^+$ cells during the first postnatal week in Nes-CreER$^{T2}$; iDTA mice, which otherwise showed normal BM histology (FIG. 21f). Developmental HSC migration to BM proceeds until the second week after birth (Dzierzak and Speck, 2008), suggesting that the BM environment might still mature during this time period to accommodate HSCs. Therefore GFP$^{+/-}$ BMSCs were isolated from E18.5 and P7 Nes-Gfp BM. The expression of HSC-supporting genes was markedly higher and progressively upregulated in GFP$^+$ cells (FIG. 21g), suggesting that nestin$^+$ MSCs might contribute to form the HSC niche in the BM.

Example 11. Nestin$^+$ MSC-Derived CXCL12 Contributes to Establish the HSC Niche in the BM HSC migration to fetal BM is enhanced by Cxcl12 and stem cell factor (Christensen et al., 2004), which are highly expressed and progressively upregulated in BM nestin$^+$ cells at perinatal stage. Cxcl12 is produced by different stromal cells and is required for developmental BM colonization by HSCs (Ara et al., 2003). It has been argued that Cxcl12 produced by endothelial cells and nestin$^-$ mesenchymal progenitors—but not by nestin$^+$ cells—is necessary for adult HSC maintenance (Ding and Morrison, 2013; Greenbaum et al., 2013). We found that, one week after birth, Cxcl12 mRNA levels were >20-80-fold higher in Nes-GFP$^+$ BMSCs than in BM endothelial and Nes-GFP$^-$ BMSCs, respectively (FIG. 21h). We conditionally deleted Cxcl12 in nestin$^+$ cells in first postnatal week using Cxcl12$^{fl}$ mice (Tzeng et al., 2010) intercrossed with Nes-CreER$^{T2}$ mice, that mostly label Nes-GFP$^+$ cells during this period (FIG. 21i). Tamoxifen administration did not significantly changed Cxcl12 mRNA levels in BM endothelial cells and instead decreased these levels by 5-fold in BMSCs (FIG. 21j-k). This was associated with ~30% reduction of BM hematopoietic progenitors (FIG. 21l). These results demonstrate that nestin$^+$ MSCs contribute to HSC niche formation in developing BM through Cxcl12 production.

Example 12. Materials and Methods for FIGS. 14-21 and Examples 1-11

12.1. Animals

Mouse lines used in this study included Nes-Gfp (Mignone et al., 2004), Nes-CreER$^{T2}$ (Balordi and Fishell, 2007), Sox10-CreER$^{T2}$ (Matsuoka et al., 2005), Col2.3-Cre (Dacquin et al., 2002), Dhh-Cre (Jaegle et al., 2003), RCE-loxP (Sousa et al., 2009), LSL-KFP (Dieguez-Hurtado et al., 2011), R26-DTA (Brockschnieder et al., 2006), Cxcl12$^{floxed}$ (Tzeng et al., 2010), Erbb3$^{floxed}$ (Sheean et al., 2014), Erbb3-null (Riethmacher et al., 1997), Tg(Wnt1-cre/ERT) 1Alj/J, 129S4.Cg-Tg(Wnt1-cre)2Sor/J, C57BL/6-Gt (ROSA)26Sor$^{tm1(HBEGF)Awai}$/j, B6.Cg-Gt(ROSA) 26Sor$^{tm14(CAG-tdTomato)Hze}$/J, CD1 and C57BL/6J mice (Jackson Laboratories). Experimental procedures were approved by the Animal Care and Use Committees of the Spanish National Center for Cardiovascular Research, Icahn School of Medicine at New York and the Karolinska Institute.

12.2. Embryo Analysis and Genetic Inducible Fate Mapping

Embryos were dissected as previously described (Isern et al., 2008). Briefly, selected intercrosses between mice carrying the alleles of interest were set and the morning of detection of the vaginal plug was considered as day 0.5 of gestation. We preferentially used paternal transgene transmission, by mating compound or simple transgenic males with females of wild type background (C57BL/6 or CD1). Inducible lineage tracing studies were done as following, tamoxifen (Sigma, T-5648) was dissolved in corn oil at a final concentration of 20 mg/mL and given to pregnant dams by oral gavage (100-150 mg/Kg) the morning of the indicated stages. For neonatal induction, mothers of newborn pups were given tamoxifen (by oral gavage, 4 mg) at days 1 and 3, post-delivery.

12.3. Histology and Cytology

Dissected tissues for histology were fixed in paraformaldehyde 2% at 4° C., cryopreserved by consecutive equilibration in 15% and 30% sucrose, and snap frozen embedded in OCT compound (Tissue-Tek). In some cases, fixed frozen limbs or sterna were trimmed sequentially from both sides until exposing the central medullar cavity and processed further for whole mount fluorescence staining. Cryostat sections at 15 □m thickness were prepared and processed for immunostaining or regular hematoxylin-eosin stain. Oil red O staining was performed as described (Isern et al., 2013a).

12.4. Immunohistochemistry

Staining of cryostat sections was performed by standard procedures. Briefly, tissues were permeabilized for 5-10 min at room temperature (RT) with 0.1% Triton X-100 and blocked with TNB buffer (0.1M Tris-HCl, pH 7.5, 0.15M NaCl, 0.5% blocking reagent, Perkin Elmer) for 1 h at RT. Primary antibodies were either incubated for 1-2 h at RT or overnight (o/n) at 4° C., secondary antibodies incubated for 1 h at RT. Repetitive washes were performed with PBS+ 0.05% Tween-20. Stained tissue sections were counterstained for 5 min with 5 □M DAPI and rinsed with PBS. Slides were mounted using Vectashield hardset mounting medium (Vector Labs) and sealed with nail polish.

For whole mount staining of thick-sectioned tissue pieces), all the incubations, including permeabilization and blocking were performed o/n at 4° C. with gently agitation, and washing steps extended. Mounting of the specimens was done onto glass bottom dishes (Mat-Tek). For adult specimen studies, 2-month old Wnt1-Cre;Rosa26-Tomato double-transgenic mice were perfused with 4% paraformaldehyde. The bone marrow was extruded by subsequently cleaning the femur from attached soft tissue, cutting both cleaned ends and passing fixative solution through the bone marrow using a 5 ml syringe and 25 G hypodermic needle.

Embryos were taken out from pregnant females and subsequently immersed overnight in cold 4% paraformaldehyde and then placed in 10-20% sucrose in PBS. Tissue was OCT embedded and sectioned (14 µm thickness). Immunohistochemical procedures were previously described (Aquino et al., 2006).

12.5. Immunofluorescence

Staining of fetal BM and fetal liver sections were performed following standard procedures. Antibodies used are indicated in table (see below). SLAM staining was performed in bone marrow sections from neonate mice. Slides were first blocked in 20% goat serum in PBS for 45 min. Endogenous avidin and biotin were blocked with Avidin/Biotin Blocking Kit (Vector Laboratories) for 30 min with each reagent, washing 3 times with PBS in between. Slides were then incubated in rat anti-mouse CD150 antibody (Biolegend) at 1:50 dilution in goat blocking buffer for 2 h. Goat anti-rat IgG conjugated to Alexa555 (Molecular Probes) was added at 1:200 dilution in 20% goat serum in PBS for 1 h. Slides were then blocked in 20% rat serum in PBS for 10 min. Then they were incubated in hamster anti-mouse biotin-conjugated CD48 (Abcam) and in Biotin Mouse Lineage Panel (BD Pharmingen) including rat anti-mouse B220, rat anti-mouse CD3, rat anti-mouse Gr1, rat anti-mouse Mac-1 and rat anti-mouse Ter119 antibodies, each at 1:200 dilution in rat blocking buffer for 1 h. Cy5-conjugated streptavidin (Molecular Probes) was added at 1:200 in rat blocking buffer for 30 min. Finally, slides were incubated with DAPI (1:1000 dilution of 5 mg/ml stock) for 10 min at room temperature and mounted using Vectashield Mounting Medium (Vector).

Antibodies Used for Immunohistochemistry:

| Name | Type | Company |
| --- | --- | --- |
| TH | Rabbit pAb | Millipore |
| GFAP | Rabbit pAb | Dako |
| CD31 | Rat mAb | BD Pharmingen |
| S100 | Rabbit pAb | Dako |
| Collagen type IV | Rabbit pAb | Millipore |
| Ki67 | Rabbit pAb | Abcam |
| Anti-KFP | Rabbit pAb | Evrogen |
| CD150 | Rat mAb | Biolegend |
| CD48 | ArHm mAb | Abcam |
| Lineage-biotin | Rat mAb | BD Biosciences |
| Tuj1 | Mouse mAb | Promega |
| Anti-GFP | Rabbit pAb | Abcam |
| c-kit | goat pAb | R&D |
| Nestin | Rabbit pAb? | Abcam |
| □-SMA | Mouse mAb | Sigma |

12.6. Imaging

Confocal images from fluorescent staining were acquired with either a laser scanning confocal (Zeiss LSM 700, 10×/0.45, 25×/0.85) or a multi-photon Zeiss LSM 780 microscope (20×/1.0). Optical z-stack projections were generated with Zen2011 software package (Zeiss) using maximal intensity algorithm. Wide-field images of whole mount specimens were imaged on a Leica MZFLIII stereomicroscope equipped with an Olympus DP71 color camera. Images were post-processed and quantified using ImageJ (Schneider et al., 2012) and Photoshop (Adobe) software.

12.7. Preparation of Fetal and Infantile BM Cell Suspensions

Fetal skeletal elements were sub-dissected from fetuses, homogenized by cutting, and digested in 0.25% collagenase (StemCell Technologies, Cat. #07902) for 15-30 min at 37° C. with shaking. Postnatal bone specimens were cleaned from surrounding tissue, crushed in a mortar with a pestle and collagenase-digested for 45-60 min at 37° C., with constant agitation. After enzymatic treatment, skeletal preparations were filtered through a 40 □m-cell strainer and undigested bone material discarded. The resulting bone marrow-enriched cell suspensions were pelleted, washed twice and resuspended in FACS staining buffer (2% FCS in PBS) for further analyses.

12.8. Flow Cytometry

Dispersed bone marrow cell preparations were stained in FACS buffer for 15-30 min on ice with selected multicolor antibody cocktails (Please see below), washed and resuspended with Streptavidin conjugates when necessary. Stained cells were pelleted and resuspended in buffer containing DAPI to exclude dead cells. Cell cycle analysis by FACS was performed by isolating first defined stromal populations by FACS sorting, and then acquiring the cell cycle profile after staining the sorted populations with Hoescht 33342. FACS analysis and sorting were done in either FACS Cantoll or LSRFortessa machines (BD Biosciences) equipped with Diva Software (BD Biosciences), or in a FACS Ariall cell sorter (BD Biosciences). Data were analyzed using Diva and FlowJo (Tree Star, Inc).

Antibodies Used for Cytometry:

| Name | Clone | Company |
| --- | --- | --- |
| CD45-APC/Cy7 | 104 | BD Biosciences |
| CD45-APC | 104 | BD Biosciences |
| CD31-APC | MEC 13.3 | BD Biosciences |
| Ter119-APC | Ter119 | BD Biosciences |
| CD140a-biotin | APA5 | eBioscience |
| CD140a-APC | APA5 | Biolegend |
| CD90.2-APC | 53-2.1 | eBioscience |
| Ly6a-PE | E13-161.7 | BD Biosciences |
| Vcam1-PE | 429 (MVCAM.A) | Biolegend |
| Streptavidin-PE | — | BD Biosciences |
| Lineage cocktail- | | BD Biosciences |

12.9. CFU-F and CFU-OB Assays

For CFU-F assays, BM cell suspensions were FACS sorted directly into 6-well plates at a cell density of 100-500 cells/cm$^2$, and cultured in maintenance medium (α-MEM/ 15% FCS with antibiotics). After 10-12 days in culture, adherent cells were fixed with 100% methanol and stained with Giemsa stain (Sigma) to reveal fibroblastic clusters. Colonies with more than 50 cells scored as CFU-F. For CFU-OB assays, plated cells were cultured in maintenance medium in the presence of 1 mM L-ascorbate-2-phosphate. All cultures were maintained with 5% $CO_2$ in a water-jacketed incubator at 37° C., and medium changes was performed weekly. After 25 days in culture, cells were fixed and stained with alizarin red or alkaline phosphatase, as previously described (Isern et al., 2013a).

12.10. Hematopoietic Progenitor Assays

Single cell suspensions were prepared from BM and mixed with methylcellulose-containing medium with cytokines (Casanova-Acebes et al., 2013). Cells ($5$-$7.5 \times 10^4$) were plated in duplicates in 35 mm dishes (Falcon, BD), and incubated under 20% $O_2$ and 5% $CO_2$ in a water-jacketed incubator. Hematopoietic colonies (CFU-Cs) were scored after 6-7 days in culture.

12.11. Long-Term Culture-Initiating Cell Assay

Long-term culture-initiating cell assay was performed as described (Woehrer et al., 2013). Briefly, the feeder fetal stromal cell line AFT024 (kindly provided by Dr. K. Moore) was maintained as previously described (Nolta et al., 2002). One week before use, the feeders were irradiated (15 Gy) with a 137Cs irradiator and seeded in 96-well plates at confluency. After 7-10 days, five serial dilutions (each one with 16 replicates) of sorted fetal liver $Lin^-$ $Sca1^+$ cells and BM nucleated cells were seeded on the irradiated feeders and cultured with Myelocult M5300 supplemented with $10^{-6}$ M hydrocortisone (StemCell Technologies) and 1% penicillin-streptomycin (Invitrogen). Cultures were maintained for four weeks at 33° C. under 20% $O_2$ and 5% $CO_2$ in a water-jacketed incubator. Half-medium changes were performed weekly. Each well was then trypsinized for 10 minutes, washed with PBS and plated in the hematopoietic progenitor assay. Twelve days after plating, the percentage of culture dishes in each experimental group that failed to generate CFU-C was plotted against the number of test cells. The frequencies of long-term culture-initiating cells were calculated using L-Calc™ software (StemCell Technologies) by Newton-Raphson method of maximum likelihood and Poisson statistics as the reciprocal of the number of test wells that yielded a 37% negative response.

12.12. Adult Skeletal Phenotype Analysis

ELISA.

The tartrate-resistant acid phosphatase (TRAP) activity was measured in plasma and samples of BM extracellular fluid using the Mouse TRAP SB-TR103 kit (Immuno Diagnostics Systems), following the manufacturer's recommendations. The deoxypyridinoline (DPD) cross-link urine test to measure bone re-absorption rates was performed using the MicroVueDPD 8007 kit (Quidel Corporation), as recommended by the provider. The alkaline phosphatase levels were determined in plasma and BM extracellular fluids using ALP-Alkaline Phosphatase Flex Reagent (Siemens) in a Dimension RxL Max analyzer, following the manufacturer's instructions.

Cell Culture and In Vitro Differentiation.

Primary BM cells were obtained from dissected bones using a mortar. All cultures were maintained at 37° C. with 20% $O_2$, 5% $CO_2$ in a water-jacketed incubator.

To obtain fibroblastic (CFU-F) and osteoblastic colony-forming units (CFU-OB), $0.5 \times 10^6$ BM nucleated cells were seeded in each well of a 12-well plate with α-MEM medium supplemented with 1% penicillin-streptomycin, 15% FBS (Invitrogen) and 1 mM L-ascorbic acid 2-phosphate (Sigma). Half medium was replaced every 5 days. The numbers of CFU-F and CFU-OB were scored after 10 and 28 days in culture, respectively.

CFU-F cultures were fixed using methanol during 10 min. at room temperature. Staining was performed with GIEMSA diluted 1:10 in phosphate buffer pH 6.8 for 10 min. at 37° C. CFU-F colonies (those with more than 50 cells) were counted the day after.

CFU-OB cultures were fixed with 4% paraformaldehyde (PFA) for 5 min. at room temperature. Von Kossa staining was performed adding 5% $AgNO_3$ to the culture and plates were exposed to UV radiation for 20 min. After that cells were incubated with 5% $(NH_4)_2S_2O_3$ in distilled water during 5 min. Cells were counterstained with 2% eosin. For Alizarin Red staining, cells were incubated with 2% alizarin red reagent (Sigma) in distilled $H_2O$ for 15 min. For alkaline phosphatase staining, Sigma Fast BCIP/NBT substrate (Sigma) was added to cell cultures and incubated in darkness for 15 min.

In vitro differentiated osteoclasts were derived from BM nucleated cells seeded for 2 days in 1 well of a six-well plate with α-MEM medium supplemented with 10% FBS, 1% P/S (Invitrogen) and 5 ng/ml hM-CSF (Peprotech). After 2 days, stromal plastic-adherent cells were discarded and 0.5 million non-adherent cells were seeded in each well of a 12-well plate with α-MEM supplemented with 10% FBS (Invitrogen), 30 ng/ml hM-CSF and 60 ng/ml shRANK (Peprotech). The medium was changed every two days. Cultures were stopped after 6-8 days, depending on the cell differentiation status. The cells were fixed in 37% formaldehyde supplemented with citrate and acetone for 1 min. To stain osteoclasts, TRAP staining kit (Biocat) was used following manufacturer's recommendations.

Histology.

Femurs were embedded in OCT and 10 μm sections were obtained. Sections were stained with Acid Phosphatase, Leukocyte (TRAP) kit (Sigma), following manufacturer's instructions.

Nucleic Acid Purification and qPCR.

RNA from CFU-F and osteoblasts cultures was extracted using Trizol reagent (Sigma-Aldrich) according to the manufacturer's instructions and was purified with RNeasy mini columns (Qiagen). An on-column DNase digest (Qiagen) was performed before the clean-up step to eliminate residual genomic DNA. In case of osteoclasts cultures, mRNA was extracted using Dynabeads mRNA Direct kit (Invitrogen). In both cases, finally cDNA was generated using Hight Capacity cDNA Reverse Transcription reagents (Applied Biosystems). qPCR was performed in triplicate with SYBRgreen Universal PCR Master Mix (Applied Biosystems). Primers optimized for each target gene were used. Relative quantification for each transcript was obtained by normalizing against Gapdh transcript abundance, using the standard curve method. Bone histomorphometric studies were performed as previously described (Sun et al., 2013).

12.13. Primary Sphere-Forming Cultures

For sphere formation, cells were plated at clonal density (<1,000 cells/$cm^2$) in ultra-low adherent 35 mm dishes (StemCell Technologies). The growth medium contained 15% chicken embryo extract, prepared as described (Pajtler et al., 2010; Stemple and Anderson, 1992); 0.1 mM β-mercaptoethanol; 1% non-essential aminoacids (Sigma); 1% N2 and 2% B27 supplements (Invitrogen); recombinant human fibroblast growth factor (FGF)-basic, recombinant human epidermal growth factor (EGF), recombinant human platelet-derived growth factor (PDGF-AB), recombinant human oncostatin M (227 a.a. OSM) (20 ng/ml) and recombinant human insulin-like growth factor-1 (IGF-1; 40 ng/ml) (Peprotech) in DMEM/F12 (1:1)/human endothelial (1:2) serum-free medium (Invitrogen). The cultures were kept at 37° C. with 5% $CO_2$, 20% $O_2$ in a water-jacketed incubator and left untouched for one week to prevent cell aggregation in low density cultures. One-half medium changes were performed weekly. Mesenspheres were scored at day 10-14.

12.14. In Vitro Differentiation of Schwann Cells from BM Precursors

We have adapted the original method by Biernaskie et al. Isolation of skin-derived precursors (SKPs) and differentiation and enrichment of their Schwann cell progeny. Nat Protoc (2006) vol. 1 (6) pp. 2803-12, with some modifications. Defined stromal populations were isolated based on GFP and PDGFR☐ expression from collagenase-treated BM of Nes-Gfp neonates. Sorted cells were plated onto laminin/polylysine coated chamberslide dishes (Labtek) and allowed to attach and expand in SKP medium I. After 3 days, cells were changed to SKP medium II (containing Neuregulin-1 at 50 ng/mL) and allowed to further differentiate for >10 days. In vitro generated schwann cells were defined by morphology as thin and elongated cells. After differentiation cells were fixed with PFA 4%, gently permeabilized with Triton X-100, and stained for immunofluorescence with anti-glial fibrillary acidic protein (GFAP) antibody (Dako).

12.15. In Vitro Differentiation of BM Mesenchymal Cells

Defined stromal populations were isolated based on GFP and PDGFR☐ expression from collagenase-treated BM of Nes-Gfp neonates and plated directly into plastic dishes to allow attachment of fibroblastic cells. Adherent cells were cultured in regular a-MEM medium supplemented with 15% FBS, for 7-14 days. In some cases recombinant PDGF was added at a concentration of 20 ng/mL. After culture period, cells were fixed and further stained with Oil red O, to reveal adipocytic cells, and counterstained with hematoxylin.

12.16. RNA Isolation and Quantitative Real-Time RT-PCR

RNA isolation was performed using the Dynabeads® mRNA DIRECT™ Micro Kit (Invitrogen). Reverse transcription was performed using the Reverse Transcription System (Promega), following the manufacturer's recommendations. Quantitative real-time RT-PCR was performed as previously described (Mendez-Ferrer et al., 2008). The expression level of each gene was determined by using the relative standard curve method. Briefly, a standard curve was performed by doing serial dilutions of a human reference total RNA (Clontech). The expression level of each gene was calculated by interpolation from the standard curve. All values were normalized with GAPDH as endogenous control. The sequences of oligonucleotides for qPCR are detailed below.

| Target gene | Symbol | Forward | Reverse |
|---|---|---|---|
| Alkal.Phosphaas | Alpl | CACAATATCAAGGATATCGACGTGA | ACATCAGTTCTGTTCTTCGGGTACA |
| Osterix | Sp7 | ATGGCGTCCTCTCTGCTTGA | GAAGGGTGGGTAGTCATTTG |
| Runx2 | Runx2 | TTACCTACACCCCGCCAGTC | TGCTGGTCTGGAAGGGTCC |
| Rank Ligand | Rankl | CAGCATCGCTCTGTTCCTGTA | CTGCGTTTTCATGGAGTCTCA |
| Gpnmb | Gpnmb | CCCCAAGCACAGACTTTTGAG | GCTTTCTGCATCTCCAGCCT |
| Osteocalcin | Bglap | GGGCAATAAGGTAGTGAACAG | GCAGCACAGGTCCTAAATAGT |
| Osteoglycin | Ogn | ACCATAACGACCTGGAATCTGT | AACGAGTGTCATTAGCCTTGC |
| Rank | Rank | TGCAGCTCAACAAGGATACG | GAGCTGCAGACCACATCTGA |
| TRAP | Acp5 | CAGCAGCCAAGGAGGACTAC | ACATAGCCCACACCGTTCTC |
| Cathepsin k | Ctsk | GGCCTCTCTTGGCCATA | CCTTCCCACTCTGGGTAG |
| Mmp-9 | Mmp9 | CGTCGTGATCCCCACTTACT | AACACACAGGGTTTGCCTTC |
| Ppar gamma | Pparg | ACCACTCGCATTCCTTTGAC | TGGGTCAGCTCTTGTGAATG |
| Adiponectin | Adipoq | TGTTCCTCTTAATCCTGCCCA | CCAACCTGCACAAGTTCCCTT |
| Adipsin | Cfd | TGCATCAACTCAGAGTGTCAATCA | TGCGCAGATTGCAGGTTGT |
| Sox9 | Sox9 | GAACAGACTCACATCTCT | GTGGCAAGTATTGGTCAA |
| Col2a1 | Col2a1 | GTGGAGCAGCAAGAGCAAGGA | CTTGCCCCACTTACCAGTGTG |
| Aggrecan | Acan | CACGCTACACCCTGGACTTTG | CCATCTCCTCAGCGAAGCAGT |
| Cxcl12 | Cxcl12 | CGCCAAGGTCGTCGCCG | TTGGCTCTGGCGATGTGGC |
| Kit Ligand | Kitl | CCCTGAAGACTCGGGCCTA | CAATTACAAGCGAAATGAGAGCC |
| Anoiopoietin 1 | Angpt1 | CTCGTCAGACATTCATCATCCAG | CACCTTCTTTAGTGCAAAGGCT |

12.17. RNA-Seq

For next-generation sequencing, total RNA was isolated using the Arcturus Picopure RNA isolation kit (Life Technologies) from small numbers of FACS sorted cells (15,000-80,000), obtained from neonatal Nes-Gfp bone marrow preparations (2 biological replicates). Each independent set of samples was obtained from pooled skeletal elements (long bones and sterna) form multiple littermates.

RNA-Seq Library Production.

The RNA sequencing library was prepared with the TruSeq RNA Sample Preparation v2 Kit (Illumina, San Diego, Calif.) to construct index-tagged cDNA. The quality, quantity and the size distribution of the Illumina libraries were determined using the DNA-1000 Kit (Agilent Bioanalyzer). Libraries were sequenced on the Genome Analyzer IIx (Illumina) following the standard RNA sequencing protocol with the TruSeq SBS Kit v5. Fastq files containing reads for each library were extracted and demultiplexed using Casava v1.8.2 pipeline.

RNA-Seq Analysis.

Sequencing adaptor contaminations were removed from reads using cutadapt software tool (MIT) and the resulting reads were mapped and quantified on the transcriptome (NCBIM37 Ensembl gene-build 65) using RSEM v1.17 (Li and Dewey, 2011). Only genes with >two counts per million in ≥two samples were considered for statistical analysis. Data were then normalized and differential expression assessed using the bioconductor package EdgeR (Robinson et al., 2010). Batch correction was achieved using ComBat (Johnson et al., 2007) on the log 2-normalized GEO data sets together with the log 2 normalized counts from each RNA-Seq experiment. We considered as differentially expressed those genes with a Benjamini-Hochberg adjusted p-value ≤0.05.

Principal Component Analysis (PCA) Comparison with Previously Published Data.

Normalized RNA-Seq data were compared via principal components analysis (PCA) to previously published array expression data (see Table S3). GEO data sets were downloaded and pre-processed using the GEOquery Bioconductor package (Davis and Meltzer, 2007). Normalized data sets were adjusted to the same intensity range, as previously described (Heider and Alt, 2013). Batch effect correction was performed using ComBat (Johnson et al., 2007).

12.18. References

Ara, T., Tokoyoda, K., Sugiyama, T., Egawa, T., Kawabata, K., and Nagasawa, T. (2003). Long-term hematopoietic stem cells require stromal cell-derived factor-1 for colonizing bone marrow during ontogeny. Immunity 19, 257-267.

Arai, F., Hirao, A., Ohmura, M., Sato, H., Matsuoka, S., Takubo, K., Ito, K., Koh, G. Y., and Suda, T. (2004). Tie2/angiopoietin-1 signaling regulates hematopoietic stem cell quiescence in the bone marrow niche. Cell 118, 149-161.

Avecilla, S. T., Hattori, K., Heissig, B., Tejada, R., Liao, F., Shido, K., Jin, D. K., Dias, S., Zhang, F., Hartman, T. E., et al. (2004). Chemokine-mediated interaction of hematopoietic progenitors with the bone marrow vascular niche is required for thrombopoiesis. Nat Med 10, 64-71.

Balordi, F., and Fishell, G. (2007). Mosaic removal of hedgehog signaling in the adult SVZ reveals that the residual wild-type stem cells have a limited capacity for self-renewal. J Neurosci 27, 14248-14259.

Brockschnieder, D., Pechmann, Y., Sonnenberg-Riethmacher, E., and Riethmacher, D. (2006). An improved mouse line for Cre-induced cell ablation due to diphtheria toxin A, expressed from the Rosa26 locus. Genesis 44, 322-327.

Calvi, L. M., Adams, G. B., Weibrecht, K. W., Weber, J. M., Olson, D. P., Knight, M. C., Martin, R. P., Schipani, E., Divieti, P., Bringhurst, F. R., et al. (2003). Osteoblastic cells regulate the haematopoietic stem cell niche. Nature 425, 841-846.

Caplan, A. I. (1991). Mesenchymal stem cells. Journal of orthopaedic research: official publication of the Orthopaedic Research Society 9, 641-650.

Chan, C. K., Chen, C. C., Luppen, C. A., Kim, J. B., Deboer, A. T., Wei, K., Helms, J. A., Kuo, C. J., Kraft, D. L., and Weissman, I. L. (2008). Endochondral ossification is required for haematopoietic stem-cell niche formation. Nature.

Chan, C. K., Lindau, P., Jiang, W., Chen, J. Y., Zhang, L. F., Chen, C. C., Seita, J., Sahoo, D., Kim, J. B., Lee, A., et al. (2013). Clonal precursor of bone, cartilage, and hematopoietic niche stromal cells. Proc Natl Acad Sci USA 110, 12643-12648.

Christensen, J. L., Wright, D. E., Wagers, A. J., and Weissman, I. L. (2004). Circulation and chemotaxis of fetal hematopoietic stem cells. PLoS Biol 2, E75.

Crisan, M., Yap, S., Casteilla, L., Chen, C. W., Corselli, M., Park, T. S., Andriolo, G., Sun, B., Zheng, B., Zhang, L., et al. (2008). A perivascular origin for mesenchymal stem cells in multiple human organs. Cell stem cell 3, 301-313.

Dacquin, R., Starbuck, M., Schinke, T., and Karsenty, G. (2002). Mouse alpha1(I)-collagen promoter is the best known promoter to drive efficient Cre recombinase expression in osteoblast. Dev Dyn 224, 245-251.

Dieguez-Hurtado, R., Martin, J., Martinez-Corral, I., Martinez, M. D., Megias, D., Olmeda, D., and Ortega, S. (2011). A Cre-reporter transgenic mouse expressing the far-red fluorescent protein Katushka. Genesis 49, 36-45.

Ding, L., and Morrison, S. J. (2013). Haematopoietic stem cells and early lymphoid progenitors occupy distinct bone marrow niches. Nature 495, 231-235.

Ding, L., Saunders, T. L., Enikolopov, G., and Morrison, S. J. (2012). Endothelial and perivascular cells maintain haematopoietic stem cells. Nature 481, 457-462.

Dzierzak, E., and Speck, N. A. (2008). Of lineage and legacy: the development of mammalian hematopoietic stem cells. Nat Immunol 9, 129-136.

Friedenstein, A. J., Chailakhjan, R. K., and Lalykina, K. S. (1970). The development of fibroblast colonies in monolayer cultures of guinea-pig bone marrow and spleen cells. Cell Tissue Kinet 3, 393-403.

Glejzer, A., Laudet, E., Leprince, P., Hennuy, B., Poulet, C., Shakhova, O., Sommer, L., Rogister, B., and Wislet-Gendebien, S. (2011). Wnt1 and BMP2: two factors recruiting multipotent neural crest progenitors isolated from adult bone marrow. Cell Mol Life Sci 68, 2101-2114.

Greenbaum, A., Hsu, Y. M., Day, R. B., Schuettpelz, L. G., Christopher, M. J., Borgerding, J. N., Nagasawa, T., and Link, D. C. (2013). CXCL12 in early mesenchymal progenitors is required for haematopoietic stem-cell maintenance. Nature 495, 227-230.

Isern, J., Martin-Antonio, B., Ghazanfari, R., Martin, A. M., Lopez, J. A., del Toro, R., Sanchez-Aguilera, A., Arranz, L., Martin-Perez, D., Suarez-Lledo, M., et al. (2013).

Self-renewing human bone marrow mesenspheres promote hematopoietic stem cell expansion. Cell Rep 3, 1714-1724.

Jaegle, M., Ghazvini, M., Mandemakers, W., Piirsoo, M., Driegen, S., Levavasseur, F., Raghoenath, S., Grosveld, F., and Meijer, D. (2003). The POU proteins Brn-2 and Oct-6 share important functions in Schwann cell development. Genes Dev 17, 1380-1391.

Jessen, K. R., and Mirsky, R. (2005). The origin and development of glial cells in peripheral nerves. Nat Rev Neurosci 6, 671-682.

John, N., Cinelli, P., Wegner, M., and Sommer, L. (2011). Transforming growth factor beta-mediated Sox10 suppression controls mesenchymal progenitor generation in neural crest stem cells. Stem Cells 29, 689-699.

Katayama, Y., Battista, M., Kao, W. M., Hidalgo, A., Peired, A. J., Thomas, S. A., and Frenette, P. S. (2006). Signals from the sympathetic nervous system regulate hematopoietic stem cell egress from bone marrow. Cell 124, 407-421.

Kiel, M. J., Yilmaz, O. H., Iwashita, T., Terhorst, C., and Morrison, S. J. (2005). SLAM family receptors distinguish hematopoietic stem and progenitor cells and reveal endothelial niches for stem cells. Cell 121, 1109-1121.

Komada, Y., Yamane, T., Kadota, D., Isono, K., Takakura, N., Hayashi, S., and Yamazaki, H. (2012). Origins and properties of dental, thymic, and bone marrow mesenchymal cells and their stem cells. PloS one 7, e46436.

Kunisaki, Y., Bruns, I., Scheiermann, C., Ahmed, J., Pinho, S., Zhang, D., Mizoguchi, T., Wei, Q., Lucas, D., Ito, K., et al. (2013). Arteriolar niches maintain haematopoietic stem cell quiescence. Nature 502, 637-643.

Lewis, A. E., Vasudevan, H. N., O'Neill, A. K., Soriano, P., and Bush, J. O. (2013). The widely used Wnt1-Cre transgene causes developmental phenotypes by ectopic activation of Wnt signaling. Dev Biol 379, 229-234.

Liu, Y., Strecker, S., Wang, L., Kronenberg, M. S., Wang, W., Rowe, D. W., and Maye, P. (2013). Osterix-cre labeled progenitor cells contribute to the formation and maintenance of the bone marrow stroma. PloS one 8, e71318.

Maes, C., Kobayashi, T., Selig, M. K., Torrekens, S., Roth, S. I., Mackem, S., Carmeliet, G., and Kronenberg, H. M. (2010). Osteoblast precursors, but not mature osteoblasts, move into developing and fractured bones along with invading blood vessels. Dev Cell 19, 329-344.

Matsuoka, T., Ahlberg, P. E., Kessaris, N., Iannarelli, P., Dennehy, U., Richardson, W. D., McMahon, A. P., and Koentges, G. (2005). Neural crest origins of the neck and shoulder. Nature 436, 347-355.

Mendez-Ferrer, S., Lucas, D., Battista, M., and Frenette, P. S. (2008). Haematopoietic stem cell release is regulated by circadian oscillations. Nature 452, 442-447.

Mendez-Ferrer, S., Michurina, T. V., Ferraro, F., Mazloom, A. R., Macarthur, B. D., Lira, S. A., Scadden, D. T., Ma'ayan, A., Enikolopov, G. N., and Frenette, P. S. (2010). Mesenchymal and haematopoietic stem cells form a unique bone marrow niche. Nature 466, 829-834.

Mignone, J. L., Kukekov, V., Chiang, A. S., Steindler, D., and Enikolopov, G. (2004). Neural stem and progenitor cells in nestin-GFP transgenic mice. The Journal of comparative neurology 469, 311-324.

Morikawa, S., Mabuchi, Y., Kubota, Y., Nagai, Y., Niibe, K., Hiratsu, E., Suzuki, S., Miyauchi-Hara, C., Nagoshi, N., Sunabori, T., et al. (2009a). Prospective identification, isolation, and systemic transplantation of multipotent mesenchymal stem cells in murine bone marrow. J Exp Med 206, 2483-2496.

Morikawa, S., Mabuchi, Y., Niibe, K., Suzuki, S., Nagoshi, N., Sunabori, T., Shimmura, S., Nagai, Y., Nakagawa, T., Okano, H., et al. (2009b). Development of mesenchymal stem cells partially originate from the neural crest. Biochem Biophys Res Commun 379, 1114-1119.

Nagoshi, N., Shibata, S., Kubota, Y., Nakamura, M., Nagai, Y., Satoh, E., Morikawa, S., Okada, Y., Mabuchi, Y., Katoh, H., et al. (2008). Ontogeny and multipotency of neural crest-derived stem cells in mouse bone marrow, dorsal root ganglia, and whisker pad. Cell stem cell 2, 392-403.

Nakamura, Y., Arai, F., Iwasaki, H., Hosokawa, K., Kobayashi, I., Gomei, Y., Matsumoto, Y., Yoshihara, H., and Suda, T. (2010). Isolation and characterization of endosteal niche cell populations that regulate hematopoietic stem cells. Blood 116, 1422-1432.

Naveiras, O., Nardi, V., Wenzel, P. L., Hauschka, P. V., Fahey, F., and Daley, G. Q. (2009). Bone-marrow adipocytes as negative regulators of the haematopoietic microenvironment. Nature 460, 259-263.

Nguyen, M. T., Zhu, J., Nakamura, E., Bao, X., and Mackem, S. (2009). Tamoxifen-dependent, inducible Hoxb6CreERT recombinase function in lateral plate and limb mesoderm, CNS isthmic organizer, posterior trunk neural crest, hindgut, and tailbud. Dev Dyn 238, 467-474.

Olsen, B. R., Reginato, A. M., and Wang, W. (2000). Bone development. Annu Rev Cell Dev Biol 16, 191-220.

Omatsu, Y., Sugiyama, T., Kohara, H., Kondoh, G., Fujii, N., Kohno, K., and Nagasawa, T. (2010). The essential functions of adipo-osteogenic progenitors as the hematopoietic stem and progenitor cell niche. Immunity 33, 387-399.

Park, D., Spencer, J. A., Koh, B. I., Kobayashi, T., Fujisaki, J., Clemens, T. L., Lin, C. P., Kronenberg, H. M., and Scadden, D. T. (2012). Endogenous bone marrow MSCs are dynamic, fate-restricted participants in bone maintenance and regeneration. Cell stem cell 10, 259-272.

Pinho, S., Lacombe, J., Hanoun, M., Mizoguchi, T., Bruns, I., Kunisaki, Y., and Frenette, P. S. (2013). PDGFRalpha and CD51 mark human Nestin+ sphere-forming mesenchymal stem cells capable of hematopoietic progenitor cell expansion. J Exp Med 210, 1351-1367.

Raaijmakers, M. H., Mukherjee, S., Guo, S., Zhang, S., Kobayashi, T., Schoonmaker, J. A., Ebert, B. L., Al-Shahrour, F., Hasserjian, R. P., Scadden, E. O., et al. (2010). Bone progenitor dysfunction induces myelodysplasia and secondary leukaemia. Nature 464, 852-857.

Riethmacher, D., Sonnenberg-Riethmacher, E., Brinkmann, V., Yamaai, T., Lewin, G. R., and Birchmeier, C. (1997). Severe neuropathies in mice with targeted mutations in the ErbB3 receptor. Nature 389, 725-730.

Sacchetti, B., Funari, A., Michienzi, S., Di Cesare, S., Piersanti, S., Saggio, I., Tagliafico, E., Ferrari, S., Robey, P. G., Riminucci, M., et al. (2007). Self-renewing osteoprogenitors in bone marrow sinusoids can organize a hematopoietic microenvironment. Cell 131, 324-336.

Schatteman, G. C., Morrison-Graham, K., van Koppen, A., Weston, J. A., and Bowen-Pope, D. F. (1992). Regulation and role of PDGF receptor alpha-subunit expression during embryogenesis. Development 115, 123-131.

Sheean, M. E., McShane, E., Cheret, C., Walcher, J., Muller, T., Wulf-Goldenberg, A., Hoelper, S., Garratt, A. N., Kruger, M., Rajewsky, K., et al. (2014). Activation of MAPK overrides the termination of myelin growth and replaces Nrg1/ErbB3 signals during Schwann cell development and myelination. Genes Dev 28, 290-303.

Soriano, P. (1997). The PDGF alpha receptor is required for neural crest cell development and for normal patterning of the somites. Development 124, 2691-2700.

Sousa, V. H., Miyoshi, G., Hjerling-Leffler, J., Karayannis, T., and Fishell, G. (2009). Characterization of Nkx6-2-derived neocortical interneuron lineages. Cereb Cortex 19 Suppl 1, i1-10.

Spiegel, A., Shivtiel, S., Kalinkovich, A., Ludin, A., Netzer, N., Goichberg, P., Azaria, Y., Resnick, I., Hardan, I., Ben-Hur, H., et al. (2007). Catecholaminergic neurotransmitters regulate migration and repopulation of immature human CD34+ cells through Wnt signaling. Nat Immunol 8, 1123-1131.

Takashima, Y., Era, T., Nakao, K., Kondo, S., Kasuga, M., Smith, A. G., and Nishikawa, S. (2007). Neuroepithelial cells supply an initial transient wave of MSC differentiation. Cell 129, 1377-1388.

Tzeng, Y. S., Li, H., Kang, Y. L., Chen, W. C., Cheng, W. C., and Lai, D. M. (2010). Loss of Cxcl12/Sdf-1 in adult mice decreases the quiescent state of hematopoietic stem/progenitor cells and alters the pattern of hematopoietic regeneration after myelosuppression. Blood 117, 429-439.

Yamazaki, S., Ema, H., Karlsson, G., Yamaguchi, T., Miyoshi, H., Shioda, S., Taketo, M. M., Karlsson, S., Iwama, A., and Nakauchi, H. (2011). Nonmyelinating Schwann cells maintain hematopoietic stem cell hibernation in the bone marrow niche. Cell 147, 1146-1158.

Yang, W., Wang, J., Moore, D. C., Liang, H., Dooner, M., Wu, Q., Terek, R., Chen, Q., Ehrlich, M. G., Quesenberry, P. J., et al. (2013). Ptpn11 deletion in a novel progenitor causes metachondromatosis by inducing hedgehog signalling. Nature 499, 491-495.

Zaidi, M., and Mendez-Ferrer, S. (2013). Cell biology: tumour stem cells in bone. Nature 499, 414-416.

Zhang, J., Niu, C., Ye, L., Huang, H., He, X., Tong, W. G., Ross, J., Haug, J., Johnson, T., Feng, J. Q., et al. (2003). Identification of the haematopoietic stem cell niche and control of the niche size. Nature 425, 836-841.

Aquino, J. B., Hjerling-Leffler, J., Koltzenburg, M., Edlund, T., Villar, M. J., and Ernfors, P. (2006). In vitro and in vivo differentiation of boundary cap neural crest stem cells into mature Schwann cells. Exp Neurol 198, 438-449.

Casanova-Acebes, M., Pitaval, C., Weiss, L. A., Nombela-Arrieta, C., Chevre, R., N, A. G., Kunisaki, Y., Zhang, D., van Rooijen, N., Silberstein, L. E., et al. (2013). Rhythmic Modulation of the Hematopoietic Niche through Neutrophil Clearance. Cell 153, 1025-1035.

Davis, S., and Meltzer, P. S. (2007). GEOquery: a bridge between the Gene Expression Omnibus (GEO) and BioConductor. Bioinformatics 23, 1846-1847.

Heider, A., and Alt, R. (2013). virtualArray: a R/bioconductor package to merge raw data from different microarray platforms. BMC bioinformatics 14, 75.

Isern, J., Fraser, S. T., He, Z., and Baron, M. H. (2008). The fetal liver is a niche for maturation of primitive erythroid cells. Proc Natl Acad Sci USA 105, 6662-6667.

Johnson, W. E., Li, C., and Rabinovic, A. (2007). Adjusting batch effects in microarray expression data using empirical Bayes methods. Biostatistics 8, 118-127.

Mignone, J. L., Kukekov, V., Chiang, A. S., Steindler, D., and Enikolopov, G. (2004). Neural stem and progenitor cells in nestin-GFP transgenic mice. The Journal of comparative neurology 469, 311-324.

Example 13. Contribution of Bone Marrow Niche Mesenchymal Stem Cells to MPN Pathogenesis We previously reported that mouse BM nestin$^+$ MSCs are required to maintain HSCs$^5$ and that human BM nestin$^+$ cells can expand HSCs$^{18}$. Here we found that, despite elevated BM blood-vessel density in MPN patients, nestin$^+$ cell number and NESTIN mRNA expression were markedly reduced (FIG. 1a-b). This was reproduced in Mx1-cre; JAK2$^{V617F}$ mice that developed MPN upon plpC treatment$^{19,20}$ (FIG. 1c). MPN mice were intercrossed with a Nes-gfp line to label MSCs$^5$. Both compound mutant mice and Nes-gfp animals transplanted with mutant BM cells developed MPN and had less BM MSCs defined by GFP, surface marker expression and functional assays (FIG. 1d-g and FIG. 5a-f). Since MSC loss was concomitant with incipient BM fibrosis, we conducted long-term in vivo lineage-tracing studies to determine whether nestin$^+$ MSCs differentiate into fibroblasts or osteoblasts in MPN, thereby contributing to the stromal changes in these mice$^{19,20}$ (FIG. 5g-j). Unexpectedly, the vascular patterns of GFP$^+$ cells were similar to those in unaffected Nes-gfp mice (FIG. 1h-i). Thus, like recently reported in BCR-ABL$^+$ MPN$^{21}$, Nes-GFP$^-$ cells might generate excessive fibroblasts and osteoblasts. Nestin$^+$ MSC reduction was instead explained by 3-fold increased apoptotic rate in mutant mice (FIG. 1j), not prevented by the JAK inhibitor ruxolitinib (FIG. 6).

To determine whether nestin$^+$ MSC death could in turn stimulate MPN progression, we selectively depleted nestin$^+$ cells in vivo. This depletion did not affect mature BM Schwann cells, reported to express nestin$^{22}$, but reduced MSCs, associated with increased white and red blood cells (FIG. 1k and FIG. 7a-e). BM sections revealed excessive fibroblasts and bone formation, not yet detectable in control mice (FIG. 1l), consistent with nestin$^+$ cells not generating fibroblasts or bone cells in MPN. Disease acceleration following nestin$^+$ cell depletion also manifested as severe spleen infiltration, still absent in control mice (FIG. 1m).

At early disease stage, most primitive HSCs showed highest expansion, leading to increased haematopoietic progenitors in BM, peripheral blood and spleen. The chemokine Cxcl12 regulates HSC migration and quiescence$^{23,24}$ and is highly expressed by nestin$^+$ MSCs$^5$. Early HSC mobilisation correlated with decreased BM Cxcl12, consistent with MSC reduction. In addition, Cxcl12 expression dropped 70-fold in MPN BM Nes-GFP$^+$ cells (FIG. 7f-k). Deletion of Cxcl12$^{REF24}$ in nestin$^+$ cells in vivo increased BM haematopoietic progenitors and circulating platelets (FIG. 1n and FIG. 7l). MSC-derived Cxcl12 can thus negatively regulate JAK2$^{V617F+}$ HSC expansion.

Example 14. Alterations on Sympathetic Innervation of the Bone Marrow Niche in MPN are Associated to the Changes in Stromal MSCs To better understand BM nestin$^+$ cell alterations, genome-wide expression was profiled by next-generation sequencing. Expression of MSC and HSC-related genes was lower in MPN Nes-GFP$^+$ cells, which instead showed enrichment in Schwann cell genes and neural-related functional categories (FIG. 8a-d and Supplementary Data). Principal component analyses of independent biological samples compared with publically available data showed that control Nes-GFP$^+$ cells were closest to mesenchymal progenitors, whereas MPN Nes-GFP$^+$ clustered away from them and close to Schwann cells (FIG. 2a). These changes, confirmed by qPCR (FIG. 2b), suggested an altered HSC-niche neural component in MPN.

Sympathetic nerve fibres and ensheathing Schwann cells, adjacent to distinctive Nes-GFP$^+$ cells, and GFAP mRNA expression were markedly reduced in BM of MPN patients and mice (FIG. 2c-g and FIG. 8g-i). Time course analysis showed that BM neural damage precedes Nes-GFP$^+$ cell apoptosis (FIG. 2g), suggesting that sympathetic neuropathy could sensitise nestin+ cells to cell death triggered by mutant cells. Multiplex ELISA detected early increased interleukin-1β in MPN BM (FIG. 9a); this cytokine and its activating enzyme caspase-1 were expressed by monocytes, as previously reported[25], but also by haematopoietic progenitors (FIG. 9b-d). Compared with BM Nes-GFP− stromal cells, mRNA levels of interleukin-1 receptor and its antagonist were 10- and 1000-fold higher, respectively, and specifically upregulated in Nes-GFP+ cells in MPN (FIG. 9e-f). Therefore we chronically treated mice with an antagonist of interleukin-1 receptor. This treatment reduced platelet counts and increased BM MSC frequency, associated with reduced caspase-1 mRNA expression in haematopoietic progenitors (FIG. 2h and FIG. 9g-j). We studied whether $JAK2^{V617F+}$ HSCs might directly cause BM Schwann cell death. Unlike MSCs, BM-derived Schwann cells co-cultured with $JAK2V^{617F+}$ haematopoietic progenitors showed 3-fold higher apoptotic rate, which was blocked by interleukin-1 receptor antagonist (FIG. 2i). Together, these data suggest that HSC-derived interleukin-1β contributes to neuroglial damage, which compromises MSC survival. We therefore investigated whether sympathetic neuropathy might underlie HSC niche alterations and thus represent a therapeutic target in MPN.

Example 15. Efficient Therapeutic Strategy Against MPN Targeting the Alterations on the Bone Marrow Niche Sympathetic Innervation Through Rescue or Compensation We treated symptomatic MPN mice with the neuroprotective agent 4-methylcatechol, which can protect BM sympathetic nerve fibres during chemotherapy[26]. Schwann cells were preserved in 4-methylcatechol-treated mice, associated with prevented neutrophilia (FIG. 3a-b). Sympathetic nerve fibres regulate BM HSC traffic via $β_3$-adrenergic receptor activation in nestin+ MSCs[5,6]. This receptor is not expressed in normal or $JAK2^{V617F+}$ haematopoietic cells (FIG. 10a). Disease development was accelerated in mice lacking $β_3$-adrenergic receptor (FIG. 3c-d), uncovering a protective role of this receptor in MPN. Symptomatic mice were chronically treated with a selective $β_3$-adrenergic agonist (BRL37344) to compensate for deficient sympathetic stimulation of nestin+ MSCs. Strikingly, BRL37344 treatment prevented MPN-associated neutrophilia and thrombocytosis, delayed red blood cell reduction but did not affect blood counts in wild-type mice (FIG. 3b, e and FIG. 10b-d).

Contrasting the severe fibrosis in vehicle-injected mice, BM of BRL37344-treated animals was virtually devoid of excessive bone and fibroblastic tissue (FIG. 3f). These effects were HSC niche-dependent, since neither 4-methylcatechol nor BRL37344 affected the growth of cultured haematopoietic progenitors and leukocytosis was not rescued by BRL37344 in mice depleted in nestin+ cells (FIG. 3g and FIG. 11a). Similarly, several MPN markers were improved by treatment with the clinically-approved $β_3$-adrenergic agonist Mirabegron (FIG. 11b), albeit to lower extent probably due to its poor solubility and relatively low affinity for the murine receptor.

Example 16. Sympathetic Rescue or Compensation is Efficient when Administered at Advanced Thrombocytotic MPN Stage, and has No Deleterious Effect on Normal Haematopoiesis To investigate the potential therapeutic benefit when administered at more advanced stages, thrombocytotic and control mice were treated with BRL37344. This treatment reduced neutrophilia, erythrocytosis, thrombocytosis, BM interleukin-1β, fibrosis and osteosclerosis, rescued BM Schwann cells (FIG. 4a-d) and blocked Schwann cell program activation in BM nestin+ cells (FIG. 11c). MPN progression can thus be blocked by protection or rescue of BM neuroglia and by compensation of deficient sympathetic stimulation of nestin+ MSCs by $β_3$-adrenergic agonists.

We next asked whether MPN blockade could be mediated by preservation of MSCs and their HSC regulatory function. BRL37344 reduced IL-1β, restored Nes-GFP+ cell number and increased Cxcl12 levels in BM (FIG. 4e-g). Early BRL37344 or 4-methylcatechol treatments prevented mutant haematopoietic progenitor expansion (FIG. 4h and FIG. 12). Long-term BRL37344 treatment did not compromise normal HSCs but efficiently decreased mutant haematopoietic progenitors (FIG. 4i-j and FIG. 13), even when administered at thrombocytotic stage (FIG. 4k). Moreover, BRL37344-treated MPN mice showed 4.5-fold reduction in leukemic stem cells (FIG. 4l).

Our findings point to mutant HSCs as the cause of BM neuroglial damage that compromises MSC survival and function, critically contributing to MPN pathogenesis (FIG. 4m). The study shows that the niche damage triggered by the mutant HSC is essential for the development of a haematopoietic malignancy previously considered to be caused by the HSC alone. Targeting HSC niche-forming MSCs and their neural regulation may pave the way to more efficient therapeutic strategies in MPN.

The invention claimed is:

1. A method of treating and/or preventing MPN (myeloprofilerative neoplasms) in a patient, comprising administering to said patient a therapeutically effective amount of a compound of Formula 1:

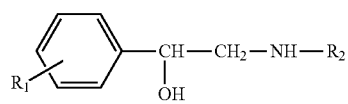

wherein R1 is selected from hydrogen and halogen; and wherein R2 is an aralkyl, being able to be substituted in the aryl part and/or in the alkyl part, or a radical selected from:

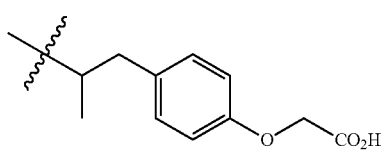

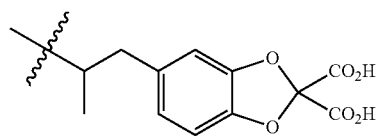

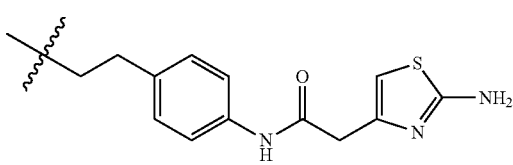

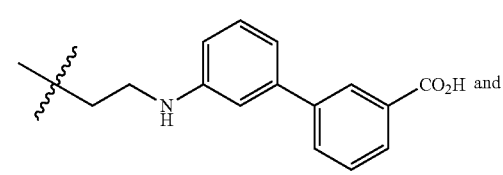

-continued

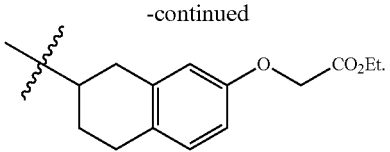

2. The method according to claim 1, wherein the MPN are selected from the group consisting of chronic myeloid leukaemia (CML), Chronic myelomonocytic leukaemia (CMML), polycythaemia vera, essential thrombocythaemia, primary myelofibrosis, Idiopathic myelofibrosis, agnogenic myeloid metaplasia, chronic neutrophilic leukaemia, chronic eosinophilic leukaemia and mastocytosis.

3. The method according to claim 1, wherein the compound is a selective beta-3 adrenergic receptor agonist.

4. The method according to claim 3, wherein said selective agonist is a phenylethanolamine.

5. The method according to claim 1, wherein the compound of formula I is selected from the group consisting of:

a.

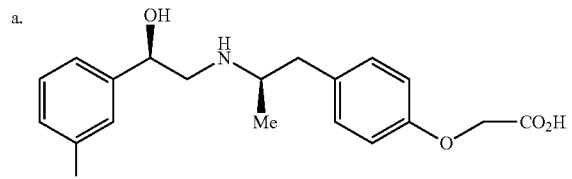

b.

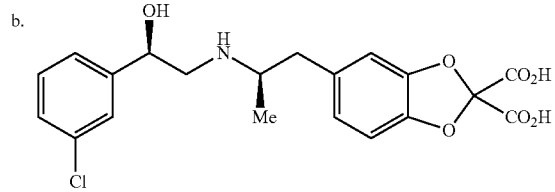

c.

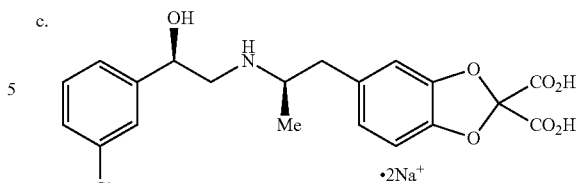

d.

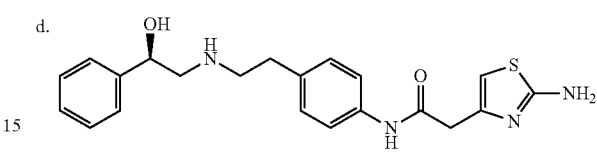

e.

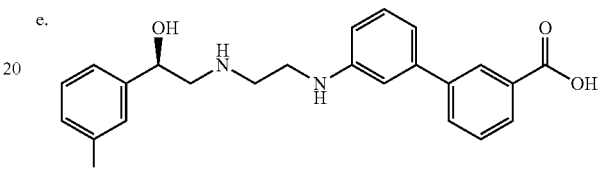

f.

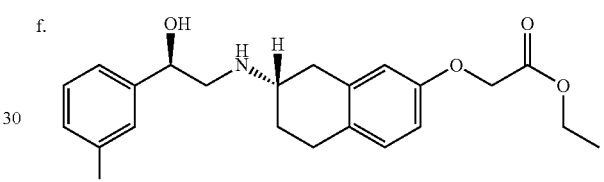

and their pharmaceutically acceptable salts.

* * * * *

SEQUENCE LISTING

<160> NUMBER OF SEQ ID NOS: 84

<210> SEQ ID NO 1
<211> LENGTH: 19
<212> TYPE: DNA
<213> ORGANISM: Artificial Sequence
<220> FEATURE:
<223> OTHER INFORMATION: Primer GFAP Forward

<400> SEQUENCE: 1
ccgacagcag gtccatgtg                                                  19

<210> SEQ ID NO 2
<211> LENGTH: 18
<212> TYPE: DNA
<213> ORGANISM: Artificial Sequence
<220> FEATURE:
<223> OTHER INFORMATION: Primer GFAP Reverse

<400> SEQUENCE: 2
gttgctggac gccattgc                                                 18

<210> SEQ ID NO 3
<211> LENGTH: 19
<212> TYPE: DNA
<213> ORGANISM: Artificial Sequence
<220> FEATURE:
<223> OTHER INFORMATION: Primer NESTIN Forward

<400> SEQUENCE: 3
caacagcgac ggaggtctc                                                19

<210> SEQ ID NO 4
<211> LENGTH: 20
<212> TYPE: DNA
<213> ORGANISM: Artificial Sequence
<220> FEATURE:
<223> OTHER INFORMATION: Primer NESTIN Reverse

<400> SEQUENCE: 4
gcctctacgc tcttctttga                                               20

<210> SEQ ID NO 5
<211> LENGTH: 18
<212> TYPE: DNA
<213> ORGANISM: Artificial Sequence
<220> FEATURE:
<223> OTHER INFORMATION: Primer GAPDH Forward

<400> SEQUENCE: 5
gcatggcctt ccgtgttc                                                 18

<210> SEQ ID NO 6
<211> LENGTH: 22
<212> TYPE: DNA
<213> ORGANISM: Artificial Sequence
<220> FEATURE:
<223> OTHER INFORMATION: Primer GAPDH Reverse

<400> SEQUENCE: 6
cctgcttcac caccttcttg at                                            22

<210> SEQ ID NO 7
<211> LENGTH: 20
<212> TYPE: DNA
<213> ORGANISM: Artificial Sequence
<220> FEATURE:
<223> OTHER INFORMATION: Primer Adrb2 Forward

<400> SEQUENCE: 7
agcaatagca acggcagaac                                               20

<210> SEQ ID NO 8
<211> LENGTH: 20
<212> TYPE: DNA
<213> ORGANISM: Artificial Sequence
<220> FEATURE:
<223> OTHER INFORMATION: Primer Adrb2 Reverse

<400> SEQUENCE: 8
ttcacaaagc cttccatgcc                                               20

```
<210> SEQ ID NO 9
<211> LENGTH: 20
<212> TYPE: DNA
<213> ORGANISM: Artificial Sequence
<220> FEATURE:
<223> OTHER INFORMATION: Primer Adrb3 Forward

<400> SEQUENCE: 9
aaactggttg cgaactgtgg                                              20

<210> SEQ ID NO 10
<211> LENGTH: 20
<212> TYPE: DNA
<213> ORGANISM: Artificial Sequence
<220> FEATURE:
<223> OTHER INFORMATION: Primer Adrb3 Reverse

<400> SEQUENCE: 10
taacgcaaag ggttggtgac                                              20

<210> SEQ ID NO 11
<211> LENGTH: 23
<212> TYPE: DNA
<213> ORGANISM: Artificial Sequence
<220> FEATURE:
<223> OTHER INFORMATION: Primer Angpt1 forward

<400> SEQUENCE: 11
ctcgtcagac attcatcatc cag                                          23

<210> SEQ ID NO 12
<211> LENGTH: 22
<212> TYPE: DNA
<213> ORGANISM: Artificial Sequence
<220> FEATURE:
<223> OTHER INFORMATION: Primer Angpt1 reverse

<400> SEQUENCE: 12
caccttcttt agtgcaaagg ct                                           22

<210> SEQ ID NO 13
<211> LENGTH: 22
<212> TYPE: DNA
<213> ORGANISM: Artificial Sequence
<220> FEATURE:
<223> OTHER INFORMATION: Primer Casp1 Forward

<400> SEQUENCE: 13
ttggagctca agttgacctc ag                                           22

<210> SEQ ID NO 14
<211> LENGTH: 22
<212> TYPE: DNA
<213> ORGANISM: Artificial Sequence
<220> FEATURE:
<223> OTHER INFORMATION: Primer Casp1 Reverse

<400> SEQUENCE: 14
tgtcagaagt cttgtgctct gg                                           22

<210> SEQ ID NO 15
<211> LENGTH: 21
<212> TYPE: DNA
<213> ORGANISM: Artificial Sequence
<220> FEATURE:
<223> OTHER INFORMATION: Primer Cxcl 12 Forward mouse
```

<400> SEQUENCE: 15
tgcatcagtg acggtaaacc a                                              21

<210> SEQ ID NO 16
<211> LENGTH: 21
<212> TYPE: DNA
<213> ORGANISM: Artificial Sequence
<220> FEATURE:
<223> OTHER INFORMATION: Primer Cxcl 12 Reverse mouse

<400> SEQUENCE: 16
ttcttcagcc gtgcaacaat c                                              21

<210> SEQ ID NO 17
<211> LENGTH: 19
<212> TYPE: DNA
<213> ORGANISM: Artificial Sequence
<220> FEATURE:
<223> OTHER INFORMATION: Primer Gfap Forward mouse

<400> SEQUENCE: 17
cggagacgca tcacctctg                                                 19

<210> SEQ ID NO 18
<211> LENGTH: 21
<212> TYPE: DNA
<213> ORGANISM: Artificial Sequence
<220> FEATURE:
<223> OTHER INFORMATION: Primer Gfap Reverse mouse

<400> SEQUENCE: 18
agggagtgga ggagtcattc g                                              21

<210> SEQ ID NO 19
<211> LENGTH: 22
<212> TYPE: DNA
<213> ORGANISM: Artificial Sequence
<220> FEATURE:
<223> OTHER INFORMATION: Primer Il1b Forward

<400> SEQUENCE: 19
gaaatgccac cttttgacag tg                                             22

<210> SEQ ID NO 20
<211> LENGTH: 21
<212> TYPE: DNA
<213> ORGANISM: Artificial Sequence
<220> FEATURE:
<223> OTHER INFORMATION: Primer Il1b Reverse

<400> SEQUENCE: 20
tggatgctct catcaggaca g                                              21

<210> SEQ ID NO 21
<211> LENGTH: 21
<212> TYPE: DNA
<213> ORGANISM: Artificial Sequence
<220> FEATURE:
<223> OTHER INFORMATION: Primer Il1r Forward

<400> SEQUENCE: 21
gtgctactgg ggctcatttg t                                              21

```
<210> SEQ ID NO 22
<211> LENGTH: 23
<212> TYPE: DNA
<213> ORGANISM: Artificial Sequence
<220> FEATURE:
<223> OTHER INFORMATION: Primer Il1r Reverse

<400> SEQUENCE: 22
ggagtaagag gacacttgcg aat                                              23

<210> SEQ ID NO 23
<211> LENGTH: 21
<212> TYPE: DNA
<213> ORGANISM: Artificial Sequence
<220> FEATURE:
<223> OTHER INFORMATION: Primer Il1rn Forward

<400> SEQUENCE: 23
gagaaacaac cagctcattg c                                                21

<210> SEQ ID NO 24
<211> LENGTH: 22
<212> TYPE: DNA
<213> ORGANISM: Artificial Sequence
<220> FEATURE:
<223> OTHER INFORMATION: Primer Il1rn Reverse

<400> SEQUENCE: 24
ggatgcccaa gaacacacta tg                                               22

<210> SEQ ID NO 25
<211> LENGTH: 19
<212> TYPE: DNA
<213> ORGANISM: Artificial Sequence
<220> FEATURE:
<223> OTHER INFORMATION: Primer Kitl Forward

<400> SEQUENCE: 25
ccctgaagac tcgggccta                                                   19

<210> SEQ ID NO 26
<211> LENGTH: 23
<212> TYPE: DNA
<213> ORGANISM: Artificial Sequence
<220> FEATURE:
<223> OTHER INFORMATION: Primer Kitl Reverse

<400> SEQUENCE: 26
caattacaag cgaaatgaga gcc                                              23

<210> SEQ ID NO 27
<211> LENGTH: 21
<212> TYPE: DNA
<213> ORGANISM: Artificial Sequence
<220> FEATURE:
<223> OTHER INFORMATION: Primer Lifr Forward

<400> SEQUENCE: 27
tacgtcggca gactcgatat t                                                21

<210> SEQ ID NO 28
<211> LENGTH: 21
<212> TYPE: DNA
<213> ORGANISM: Artificial Sequence
<220> FEATURE:
<223> OTHER INFORMATION: Primer Lifr Reverse
```

<400> SEQUENCE: 28
tgggcgtatc tctctctcct t					21

<210> SEQ ID NO 29
<211> LENGTH: 21
<212> TYPE: DNA
<213> ORGANISM: Artificial Sequence
<220> FEATURE:
<223> OTHER INFORMATION: Primer Mbp Forward

<400> SEQUENCE: 29
aatcggctca caagggattc a					21

<210> SEQ ID NO 30
<211> LENGTH: 23
<212> TYPE: DNA
<213> ORGANISM: Artificial Sequence
<220> FEATURE:
<223> OTHER INFORMATION: Primer Mbp Reverse

<400> SEQUENCE: 30
tcctcccagc ttaaagattt tgg				23

<210> SEQ ID NO 31
<211> LENGTH: 20
<212> TYPE: DNA
<213> ORGANISM: Artificial Sequence
<220> FEATURE:
<223> OTHER INFORMATION: Primer Mobp Forward

<400> SEQUENCE: 31
ccaggctctc caagaaccag					20

<210> SEQ ID NO 32
<211> LENGTH: 19
<212> TYPE: DNA
<213> ORGANISM: Artificial Sequence
<220> FEATURE:
<223> OTHER INFORMATION: Primer Mobp Reverse

<400> SEQUENCE: 32
ggtccacgat ctcacgctt					19

<210> SEQ ID NO 33
<211> LENGTH: 19
<212> TYPE: DNA
<213> ORGANISM: Artificial Sequence
<220> FEATURE:
<223> OTHER INFORMATION: Primer Nestin Forward mouse

<400> SEQUENCE: 33
ccctgaagtc gaggagctg					19

<210> SEQ ID NO 34
<211> LENGTH: 19
<212> TYPE: DNA
<213> ORGANISM: Artificial Sequence
<220> FEATURE:
<223> OTHER INFORMATION: Primer Nestin Reverse mouse

<400> SEQUENCE: 34
ctgctgcacc tctaagcga					19

```
<210> SEQ ID NO 35
<211> LENGTH: 20
<212> TYPE: DNA
<213> ORGANISM: Artificial Sequence
<220> FEATURE:
<223> OTHER INFORMATION: Primer Pkp4 Forward

<400> SEQUENCE: 35
gaacctgtca taccggctgg                                                   20

<210> SEQ ID NO 36
<211> LENGTH: 21
<212> TYPE: DNA
<213> ORGANISM: Artificial Sequence
<220> FEATURE:
<223> OTHER INFORMATION: Primer Pkp4 Reverse

<400> SEQUENCE: 36
ttccgagtct ttgctgggag a                                                 21

<210> SEQ ID NO 37
<211> LENGTH: 20
<212> TYPE: DNA
<213> ORGANISM: Artificial Sequence
<220> FEATURE:
<223> OTHER INFORMATION: Primer Plekhb1 Forward

<400> SEQUENCE: 37
ctggaagcgg aattggttcg                                                   20

<210> SEQ ID NO 38
<211> LENGTH: 21
<212> TYPE: DNA
<213> ORGANISM: Artificial Sequence
<220> FEATURE:
<223> OTHER INFORMATION: Primer Plekhb1 Reverse

<400> SEQUENCE: 38
tgccgtctcg tcatggtagt a                                                 21

<210> SEQ ID NO 39
<211> LENGTH: 19
<212> TYPE: DNA
<213> ORGANISM: Artificial Sequence
<220> FEATURE:
<223> OTHER INFORMATION: Primer Plp1 Forward

<400> SEQUENCE: 39
tgagcgcaac ggtaacagg                                                    19

<210> SEQ ID NO 40
<211> LENGTH: 21
<212> TYPE: DNA
<213> ORGANISM: Artificial Sequence
<220> FEATURE:
<223> OTHER INFORMATION: Primer Plp1 Reverse

<400> SEQUENCE: 40
ttcccaaaca atgacacacc c                                                 21

<210> SEQ ID NO 41
<211> LENGTH: 21
<212> TYPE: DNA
<213> ORGANISM: Artificial Sequence
<220> FEATURE:
<223> OTHER INFORMATION: Primer S100b Forward
```

<400> SEQUENCE: 41
tggttgccct cattgatgtc t                                              21

<210> SEQ ID NO 42
<211> LENGTH: 19
<212> TYPE: DNA
<213> ORGANISM: Artificial Sequence
<220> FEATURE:
<223> OTHER INFORMATION: Primer S100b Reverse

<400> SEQUENCE: 42
cccatcccca tcttcgtcc                                                 19

<210> SEQ ID NO 43
<211> LENGTH: 23
<212> TYPE: DNA
<213> ORGANISM: Artificial Sequence
<220> FEATURE:
<223> OTHER INFORMATION: Primer Slit2 Forward

<400> SEQUENCE: 43
ccatgtaaaa atgatggcac ctg                                            23

<210> SEQ ID NO 44
<211> LENGTH: 21
<212> TYPE: DNA
<213> ORGANISM: Artificial Sequence
<220> FEATURE:
<223> OTHER INFORMATION: Primer Slit2 Reverse

<400> SEQUENCE: 44
atcacagtcc tgacccttga a                                              21

<210> SEQ ID NO 45
<211> LENGTH: 25
<212> TYPE: DNA
<213> ORGANISM: Artificial Sequence
<220> FEATURE:
<223> OTHER INFORMATION: Primer Alpl Forward

<400> SEQUENCE: 45
cacaatatca aggatatcga cgtga                                          25

<210> SEQ ID NO 46
<211> LENGTH: 25
<212> TYPE: DNA
<213> ORGANISM: Artificial sequence
<220> FEATURE:
<223> OTHER INFORMATION: Primer Alpl Reverse

<400> SEQUENCE: 46
acatcagttc tgttcttcgg gtaca                                          25

<210> SEQ ID NO 47
<211> LENGTH: 20
<212> TYPE: DNA
<213> ORGANISM: Artificial Sequence
<220> FEATURE:
<223> OTHER INFORMATION: Primer Sp7Forward

<400> SEQUENCE: 47
atggcgtcct ctctgcttga                                                20

<210> SEQ ID NO 48
<211> LENGTH: 20
<212> TYPE: DNA
<213> ORGANISM: Artificial Sequence
<220> FEATURE:
<223> OTHER INFORMATION: Primer Sp7 Reverse

<400> SEQUENCE: 48
gaagggtggg tagtcatttg                                          20

<210> SEQ ID NO 49
<211> LENGTH: 20
<212> TYPE: DNA
<213> ORGANISM: Artificial Sequence
<220> FEATURE:
<223> OTHER INFORMATION: Primer Runx2 Forward

<400> SEQUENCE: 49
ttacctacac cccgccagtc                                          20

<210> SEQ ID NO 50
<211> LENGTH: 19
<212> TYPE: DNA
<213> ORGANISM: Artificial Sequence
<220> FEATURE:
<223> OTHER INFORMATION: Primer Runx2 Reverse

<400> SEQUENCE: 50
tgctggtctg gaagggtcc                                           19

<210> SEQ ID NO 51
<211> LENGTH: 21
<212> TYPE: DNA
<213> ORGANISM: Artificial Sequence
<220> FEATURE:
<223> OTHER INFORMATION: Primer Rankl Forward

<400> SEQUENCE: 51
cagcatcgct ctgttcctgt a                                        21

<210> SEQ ID NO 52
<211> LENGTH: 21
<212> TYPE: DNA
<213> ORGANISM: Artificial Sequence
<220> FEATURE:
<223> OTHER INFORMATION: Primer Rankl Reverse

<400> SEQUENCE: 52
ctgcgttttc atggagtctc a                                        21

<210> SEQ ID NO 53
<211> LENGTH: 21
<212> TYPE: DNA
<213> ORGANISM: Artificial Sequence
<220> FEATURE:
<223> OTHER INFORMATION: Primer Gpnm Forward

<400> SEQUENCE: 53
ccccaagcac agactttga g                                         21

<210> SEQ ID NO 54
<211> LENGTH: 20
<212> TYPE: DNA
<213> ORGANISM: Artificial Sequence
<220> FEATURE:
<223> OTHER INFORMATION: Primer Gpnm Reverse

```
<400> SEQUENCE: 54
gctttctgca tctccagcct                                              20

<210> SEQ ID NO 55
<211> LENGTH: 21
<212> TYPE: DNA
<213> ORGANISM: Artificial Sequence
<220> FEATURE:
<223> OTHER INFORMATION: Primer Bglap Forward

<400> SEQUENCE: 55
gggcaataag gtagtgaaca g                                            21

<210> SEQ ID NO 56
<211> LENGTH: 21
<212> TYPE: DNA
<213> ORGANISM: Artificial Sequence
<220> FEATURE:
<223> OTHER INFORMATION: Primer Bglap Reverse

<400> SEQUENCE: 56
gcagcacagg tcctaaatag t                                            21

<210> SEQ ID NO 57
<211> LENGTH: 22
<212> TYPE: DNA
<213> ORGANISM: Artificial Sequence
<220> FEATURE:
<223> OTHER INFORMATION: Primer Ogn Forward

<400> SEQUENCE: 57
accataacga cctggaatct gt                                           22

<210> SEQ ID NO 58
<211> LENGTH: 21
<212> TYPE: DNA
<213> ORGANISM: Artificial Sequence
<220> FEATURE:
<223> OTHER INFORMATION: Primer Ogn Reverse

<400> SEQUENCE: 58
aacgagtgtc attagccttg c                                            21

<210> SEQ ID NO 59
<211> LENGTH: 20
<212> TYPE: DNA
<213> ORGANISM: Artificial Sequence
<220> FEATURE:
<223> OTHER INFORMATION: Primer Rank Forward

<400> SEQUENCE: 59
tgcagctcaa caaggatacg                                              20

<210> SEQ ID NO 60
<211> LENGTH: 20
<212> TYPE: DNA
<213> ORGANISM: Artificial Sequence
<220> FEATURE:
<223> OTHER INFORMATION: Primer Rank Reverse

<400> SEQUENCE: 60
gagctgcaga ccacatctga                                              20
```

```
<210> SEQ ID NO 61
<211> LENGTH: 20
<212> TYPE: DNA
<213> ORGANISM: Artificial Sequence
<220> FEATURE:
<223> OTHER INFORMATION: Primer Acp5 Forward

<400> SEQUENCE: 61
cagcagccaa ggaggactac                                               20

<210> SEQ ID NO 62
<211> LENGTH: 20
<212> TYPE: DNA
<213> ORGANISM: Artificial Sequence
<220> FEATURE:
<223> OTHER INFORMATION: Primer Acp5 Reverse

<400> SEQUENCE: 62
acatagccca caccgttctc                                               20

<210> SEQ ID NO 63
<211> LENGTH: 17
<212> TYPE: DNA
<213> ORGANISM: Artificial Sequence
<220> FEATURE:
<223> OTHER INFORMATION: Primer Ctsk Forward

<400> SEQUENCE: 63
ggcctctctt ggccata                                                  17

<210> SEQ ID NO 64
<211> LENGTH: 18
<212> TYPE: DNA
<213> ORGANISM: Artificial Sequence
<220> FEATURE:
<223> OTHER INFORMATION: Primer Ctsk Reverse

<400> SEQUENCE: 64
ccttcccact ctgggtag                                                 18

<210> SEQ ID NO 65
<211> LENGTH: 20
<212> TYPE: DNA
<213> ORGANISM: Artificial Sequence
<220> FEATURE:
<223> OTHER INFORMATION: Primer Mmp9 Forward

<400> SEQUENCE: 65
cgtcgtgatc cccacttact                                               20

<210> SEQ ID NO 66
<211> LENGTH: 20
<212> TYPE: DNA
<213> ORGANISM: Artificial Sequence
<220> FEATURE:
<223> OTHER INFORMATION: Primer Mmp9 Reverse

<400> SEQUENCE: 66
aacacacagg gtttgccttc                                               20

<210> SEQ ID NO 67
<211> LENGTH: 20
<212> TYPE: DNA
<213> ORGANISM: Artificial Sequence
<220> FEATURE:
<223> OTHER INFORMATION: Primer Pparg Forward
```

<400> SEQUENCE: 67
accactcgca ttcctttgac                                                           20

<210> SEQ ID NO 68
<211> LENGTH: 20
<212> TYPE: DNA
<213> ORGANISM: Artificial Sequence
<220> FEATURE:
<223> OTHER INFORMATION: Primer Pparg Reverse

<400> SEQUENCE: 68
tgggtcagct cttgtgaatg                                                           20

<210> SEQ ID NO 69
<211> LENGTH: 21
<212> TYPE: DNA
<213> ORGANISM: Artificial Sequence
<220> FEATURE:
<223> OTHER INFORMATION: Primer Adipoq Forward

<400> SEQUENCE: 69
tgttcctctt aatcctgccc a                                                         21

<210> SEQ ID NO 70
<211> LENGTH: 21
<212> TYPE: DNA
<213> ORGANISM: Artificial Sequence
<220> FEATURE:
<223> OTHER INFORMATION: Primer Adipoq Reverse

<400> SEQUENCE: 70
ccaacctgca caagttccct t                                                         21

<210> SEQ ID NO 71
<211> LENGTH: 24
<212> TYPE: DNA
<213> ORGANISM: Artificial Sequence
<220> FEATURE:
<223> OTHER INFORMATION: Primer Cfd Forward

<400> SEQUENCE: 71
tgcatcaact cagagtgtca atca                                                      24

<210> SEQ ID NO 72
<211> LENGTH: 19
<212> TYPE: DNA
<213> ORGANISM: Artificial Sequence
<220> FEATURE:
<223> OTHER INFORMATION: Primer Cfd Reverse

<400> SEQUENCE: 72
tgcgcagatt gcaggttgt                                                            19

<210> SEQ ID NO 73
<211> LENGTH: 18
<212> TYPE: DNA
<213> ORGANISM: Artificial Sequence
<220> FEATURE:
<223> OTHER INFORMATION: Primer Sox9 Forward

<400> SEQUENCE: 73
gaacagactc acatctct                                                             18

<210> SEQ ID NO 74
<211> LENGTH: 18
<212> TYPE: DNA
<213> ORGANISM: Artificial Sequence
<220> FEATURE:
<223> OTHER INFORMATION: Primer Sox9 Reverse

<400> SEQUENCE: 74
gtggcaagta ttggtcaa                                              18

<210> SEQ ID NO 75
<211> LENGTH: 21
<212> TYPE: DNA
<213> ORGANISM: Artificial Sequence
<220> FEATURE:
<223> OTHER INFORMATION: Primer Col2a1 Forward

<400> SEQUENCE: 75
gtggagcagc aagagcaagg a                                          21

<210> SEQ ID NO 76
<211> LENGTH: 21
<212> TYPE: DNA
<213> ORGANISM: Artificial Sequence
<220> FEATURE:
<223> OTHER INFORMATION: Primer Col2a1 Reverse

<400> SEQUENCE: 76
cttgccccac ttaccagtgt g                                          21

<210> SEQ ID NO 77
<211> LENGTH: 21
<212> TYPE: DNA
<213> ORGANISM: Artificial Sequence
<220> FEATURE:
<223> OTHER INFORMATION: Primer Acan Forward

<400> SEQUENCE: 77
cacgctacac cctggacttt g                                          21

<210> SEQ ID NO 78
<211> LENGTH: 21
<212> TYPE: DNA
<213> ORGANISM: Artificial Sequence
<220> FEATURE:
<223> OTHER INFORMATION: Primer Acan Reverse

<400> SEQUENCE: 78
ccatctcctc agcgaagcag t                                          21

<210> SEQ ID NO 79
<211> LENGTH: 17
<212> TYPE: DNA
<213> ORGANISM: Artificial Sequence
<220> FEATURE:
<223> OTHER INFORMATION: Primer Cxcl12 Forward

<400> SEQUENCE: 79
cgccaaggtc gtcgccg                                               17

<210> SEQ ID NO 80
<211> LENGTH: 19
<212> TYPE: DNA
<213> ORGANISM: Artificial Sequence
<220> FEATURE:
<223> OTHER INFORMATION: Primer Cxcl12 Reverse

```
<400> SEQUENCE: 80
ttggctctgg cgatgtggc                                          19

<210> SEQ ID NO 81
<211> LENGTH: 19
<212> TYPE: DNA
<213> ORGANISM: Artificial Sequence
<220> FEATURE:
<223> OTHER INFORMATION: Primer Kitl Forward

<400> SEQUENCE: 81
ccctgaagac tcgggccta                                          19

<210> SEQ ID NO 82
<211> LENGTH: 23
<212> TYPE: DNA
<213> ORGANISM: Artificial Sequence
<220> FEATURE:
<223> OTHER INFORMATION: Primer Kitl Reverse

<400> SEQUENCE: 82
caattacaag cgaaatgaga gcc                                     23

<210> SEQ ID NO 83
<211> LENGTH: 23
<212> TYPE: DNA
<213> ORGANISM: Artificial Sequence
<220> FEATURE:
<223> OTHER INFORMATION: Primer Angpt1 Forward

<400> SEQUENCE: 83
ctcgtcagac attcatcatc cag                                     23

<210> SEQ ID NO 84
<211> LENGTH: 22
<212> TYPE: DNA
<213> ORGANISM: Artificial Sequence
<220> FEATURE:
<223> OTHER INFORMATION: Primer Angpt1 Reverse

<400> SEQUENCE: 84
caccttcttt agtgcaaagg ct                                      22
```